(12) United States Patent
Lal et al.

(10) Patent No.: US 12,194,067 B2
(45) Date of Patent: *Jan. 14, 2025

(54) INHALED RESPIRATORY PROBIOTICS FOR LUNG DISEASES OF INFANCY, CHILDHOOD AND ADULTHOOD

(71) Applicant: The UAB Research Foundation, Birmingham, AL (US)

(72) Inventors: Charitharth Vivek Lal, Birmingham, AL (US); Namasivayam Ambalavanan, Birmingham, AL (US); Amit Gaggar, Birmingham, AL (US); Casey Morrow, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/362,172

(22) Filed: Jul. 31, 2023

(65) Prior Publication Data

US 2023/0372418 A1 Nov. 23, 2023

Related U.S. Application Data

(63) Continuation of application No. 17/384,272, filed on Jul. 23, 2021, now Pat. No. 11,844,817, which is a continuation of application No. 16/604,408, filed as application No. PCT/US2018/025989 on Apr. 4, 2018, now Pat. No. 11,141,443.

(60) Provisional application No. 62/484,448, filed on Apr. 12, 2017.

(51) Int. Cl.
*A61K 35/747* (2015.01)
*A61K 9/00* (2006.01)

(52) U.S. Cl.
CPC .......... *A61K 35/747* (2013.01); *A61K 9/0043* (2013.01); *A61K 9/0078* (2013.01)

(58) Field of Classification Search
CPC .................................................. A61K 35/747
See application file for complete search history.

(56) References Cited

U.S. PATENT DOCUMENTS

| 11,141,443 | B2 | 10/2021 | Lal et al. | |
| 11,844,817 | B2* | 12/2023 | Lal | A61K 9/0043 |
| 2004/0208863 | A1 | 10/2004 | Versalovic et al. | |
| 2005/0281795 | A1 | 12/2005 | Jolly | |
| 2009/0257993 | A1 | 10/2009 | M'Rabet et al. | |
| 2010/0069860 | A1* | 3/2010 | Forsgren Brusk | A61P 31/04 |
| | | | | 435/252.9 |
| 2017/0027999 | A1 | 2/2017 | Heck et al. | |
| 2017/0333494 | A1 | 11/2017 | Willfret et al. | |

OTHER PUBLICATIONS

Harata, G., et al., "Intranasal administration of Lactobacillus rhamnosus GG protects mice from H1N1 influenza virus infection by regulating respiratory immune responses," Letters in Applied Microbiology, vol. 50, No. 6 (2010), pp. 597-602.

Lal, Charitarth Vivek, et al., "The Airway Microbiome at Birth," Scientific Reports (2016) (13 pages).

Office Action, issued by European Patent Office, EP Patent Application No. 18784388.3, Feb. 9, 2023 (6 pages).

International Search Report and Written Opinion of ISA for International Application No. PCT/US2018/025989 mailed Jul. 13, 2018.

Resta-Lenart et al., "Priobiotics and Commensals Reverse TNF-alpha- and IFN-gamma-Induced Dysfunction in Human Intestinal Epithelial Cells," Gatroenterology, vol. 130, No. 3 (2006), pp. 731-746.

Extended European Search Report for related EP Patent Application No. 18784388.3 mailed Dec. 8, 2020.

* cited by examiner

*Primary Examiner* — Albert M Navarro
(74) *Attorney, Agent, or Firm* — Thomas|Horstemeyer, LLP

(57) ABSTRACT

The respiratory microbiomes of neonates and those with bronchopulmonary disease have been characterized. Provided are probiotic compositions, which can include at least one living bacterial strain and at least one killed bacterial strain, that can comprise a combination of *Lactobacilli* species, that when delivered to the bronchi or lungs of a patient can provide a reduction in the symptoms of a bronchopulmonary disease.

8 Claims, 36 Drawing Sheets

Ac PGP (Serum)

Neutrophil Elastase - mice BALF

INHALED RESPIRATORY PROBIOTICS FOR LUNG DISEASES OF INFANCY, CHILDHOOD AND ADULTHOOD

CROSS REFERENCE TO RELATED APPLICATIONS

This application is a continuation of U.S. patent application Ser. No. 17/384,272 filed Jul. 23, 2021, which is a continuation of U.S. patent application Ser. No. 16/604,408 filed on Oct. 10, 2019, which was a 371 US National Stage Application claiming priority benefit to PCT/US2018/025989 filed on Apr. 4, 2018, which claims benefit of U.S. Provisional Patent Application Ser. No. 62/484,448 filed on Apr. 12, 2017, which is incorporated herein by reference in its entirety.

STATEMENT REGARDING FEDERALLY SPONSORED RESEARCH OR DEVELOPMENT

This invention was made with Government support under contract NIH R01 HL 129907 awarded by the National Institutes of Health. The Government has certain rights in the invention.

TECHNICAL FIELD

The present disclosure is generally related to probiotic compositions for the treatment of bronchopulmonary dysplasia, cystic fibrosis lung disease, and chronic obstructive pulmonary disease.

BACKGROUND

Microbiome analysis based on sequencing of 16S ribosomal RNA genes characterizes bacterial species present both in terms of their identities and relative abundance in contrast to traditional microbiological approaches that are restricted to analyzing species that are readily cultured (Rogers et al. (2014) *Thorax* 70:74-81; Segata et al. (2012) *Genome Biol.* 13: R42). The study of the human lung microbiome in the context of pulmonary health and disease is an area of emerging research (Mu et al. (2013) *PLOS One* 8: e58622) but it is unknown as to when the respiratory microbiome is established, and whether the airways harbor a microbiome soon after birth. Evidence of pathogenic roles for specific alterations in airway microbiota is strongest in lung diseases such as cystic fibrosis, chronic obstructive pulmonary disease (COPD), and asthma but it is not clear how the airway microbiome is initially established in newborn infants (Mu et al. (2013) *PLOS One* 8: e58622; Arrieta et al. (2015) *Sci. Transl. Med.* 7: 307ra152). Extremely premature infants are born with developmentally immature lungs that are susceptible to multiple injuries, which interfere with pulmonary alveolar and vascular development leading to bronchopulmonary dysplasia (BPD). It has been speculated that development of BPD is mediated at least in part by inflammation secondary to airway infections, and multiple studies have shown associations between lung inflammatory markers and BPD pathogenesis (D'Angio et al. (2002) *Biol. Neonate* 82:145-149; Ramsay et al. (2001) *AJRCC* 164:155-161; Watterberg et al. (1996) *Pediatrics* 97:210-215; Viscardi et al. (2004) *Ped. Res.* 55:1009-1017). Yet the direction of causality between airway injury during development and respiratory colonization with microorganisms remains unsettled. Similarly, the importance of respiratory microbiome is being explored in CF lung disease and COPD, but no microbiome therapeutics currently exist. Should a disordered airway microbiome prove to be involved in the pathogenesis of disease, it will be of immediate interest to attempt to develop novel therapeutic interventions.

SUMMARY

Briefly described, one aspect of the disclosure encompasses embodiments of a pharmaceutical composition comprising a bacterial population comprising at least one *Lactobacillus* species.

In some embodiments of this aspect of the disclosure, the bacterial population may comprise at least one *Lactobacillus* species selected from the group consisting of *Lactobacillus plantarum*, *Lactobacillus paracasei*, *Lactobacillus acidophilus* and *Lactobacillus rhamnosus*.

In some embodiments of this aspect of the disclosure, the bacterial population can consist of *Lactobacillus plantarum*, *Lactobacillus acidophilus* and *Lactobacillus rhamnosus*.

In some embodiments of this aspect of the disclosure, at least one of the *Lactobacillus* species is not capable of proliferating in the recipient patient.

In some embodiments of this aspect of the disclosure, at least one of the *Lactobacillus* species is heat-killed.

In some embodiments of this aspect of the disclosure, least one of the *Lactobacillus* species is viable and capable of proliferating in the recipient patient.

In some embodiments of this aspect of the disclosure, the bacterial population is freeze-dried.

In some embodiments of this aspect of the disclosure, the pharmaceutical composition can further comprise at least one therapeutic agent, wherein said agent or agents can reduce at least one symptom or pathological effect of a bronchopulmonary disease.

In some embodiments of this aspect of the disclosure, the therapeutic agent can be selected from the group consisting of: an anti-inflammatory agent or an anti-oxidant.

In some embodiments of this aspect of the disclosure, the bacterial population can be suspended in a pharmaceutically acceptable carrier.

In some embodiments of this aspect of the disclosure, the pharmaceutical composition is formulated for administration to the respiratory tract of a patient by nasal spray delivery.

In some embodiments of this aspect of the disclosure, the pharmaceutical composition can be formulated for administration to the respiratory tract of a patient by a nebulizer.

Another aspect of the disclosure encompasses embodiments of a method of reducing a lung disease of a patient, the method comprising the step of administering to the patient in need thereof a pharmaceutical composition comprising a bacterial population comprising at least one *Lactobacillus* species.

Still another aspect of the disclosure encompasses embodiments of a device for delivery of a pharmaceutical composition to the respiratory tract of a patient in need thereof, wherein the device comprises a nebulizer containing a pharmaceutical composition comprising a bacterial population comprising at least one *Lactobacillus* species.

Still another aspect of the disclosure encompasses embodiments of a kit comprising: at least one container and a pharmaceutical composition therein, said pharmaceutical composition comprising a bacterial population comprising at least one *Lactobacillus* species and instructions for delivery of an effective amount of the composition to a patient in need thereof.

In some embodiments of this aspect of the disclosure, the therapeutic agent can be admixed with the pharmaceutically acceptable carrier.

In some embodiments of this aspect of the disclosure, the kit can further comprise a nebulizer.

BRIEF DESCRIPTION OF THE DRAWINGS

Further aspects of the present disclosure will be more readily appreciated upon review of the detailed description of its various embodiments, described below, when taken in conjunction with the accompanying drawings.

(FIG. 1A) Bar graph depicting the relative abundance of most commonly encountered bacterial phyla between FT, ELBW and BPD infants. (FIG. 1B) Compared to newborn postmenstrual age matched FT infants and ELBW infants, infants with BPD have increased Proteobacteria and decreased Firmicutes and Fusobacteria. (FIG. 1C) Principal coordinates analysis 'PCoA' plot (beta diversity) demonstrating unweighted UniFrac distance between samples with sample points colored for ELBW, FT or BPD infants. Samples that are clustered closely together are considered to share a larger proportion of the phylogenetic tree in comparison to samples that are more separated. ELBW and FT infants have similar beta diversity, which is very different from the beta diversity of BPD infants. (FIG. 1D) Shannon diversity index depicting less microbial alpha diversity in infants with BPD compared to FT and ELBW infants.

(FIG. 4A) Heat map showing the relative abundance of genera across day 1 samples from ELBW infants who go on to develop BPD (BPD-Predisposed) versus those who do not (BPD-Resistant). Abundance of genus Lactobacillus (###) is reduced in BPD-Predisposed group (p=0.05). (FIG. 4B) Phylum level distribution of lung microbiome shows no major differences between groups. (FIG. 4C) Shannon diversity index alpha diversity is not statistically different between groups (p=0.18). (FIG. 4D) Bar graph depicting lower abundance of genus Lactobacillus in infants born to mothers with chorioamnionitis.

(FIG. 5A) Heat map showing the relative abundance of genera across day 1 samples from ELBW infants who go on to develop BPD (BPD Predisposed) versus those who do not (BPD Resistant). Abundance of genus Lactobacillus (***) is reduced in BPD Predisposed group (p=0.04). (FIG. 5B) Phylum level distribution of lung microbiome shows no major differences between groups. (FIG. 5C) Shannon diversity index shows no difference in alpha diversity between groups (p>0.1).

Inflammatory cytokines were measured in supernatants of Cystic Fibrosis Airway Epithelial Cells treated with *Pseudomonas* vs *Lactobacillus* combination. The *Lactobacillus* combination decreased almost all inflammatory cytokines.

Figure 16:
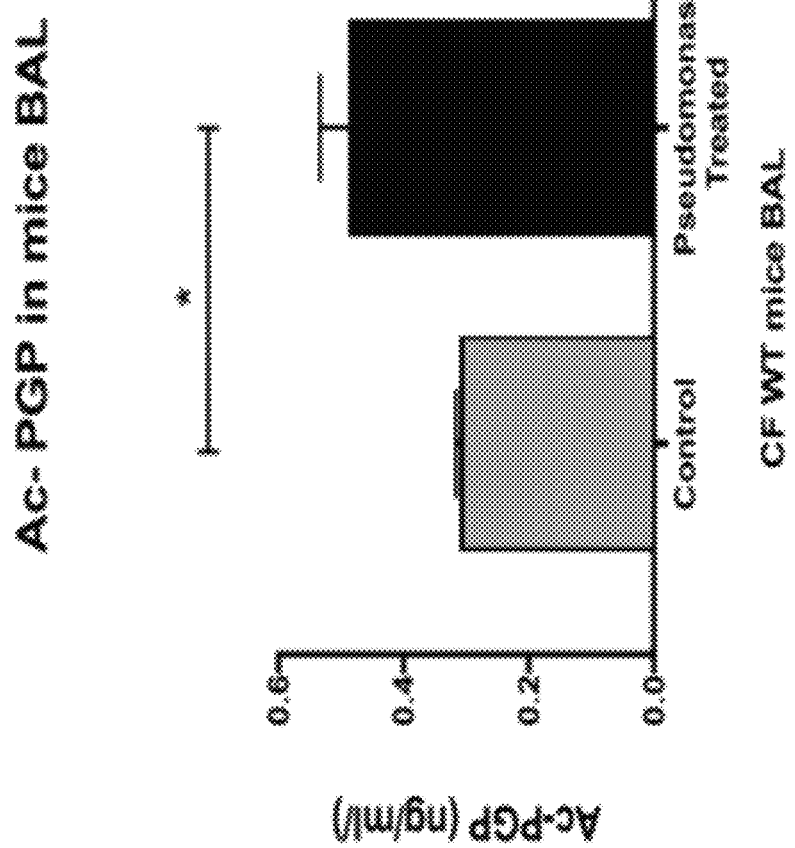

FIG. 16 is a graph illustrating the increase in Ac-PGP in wild-type mouse BAL fluid from exposure to a (*Pseudomonas*).

Figure 17:
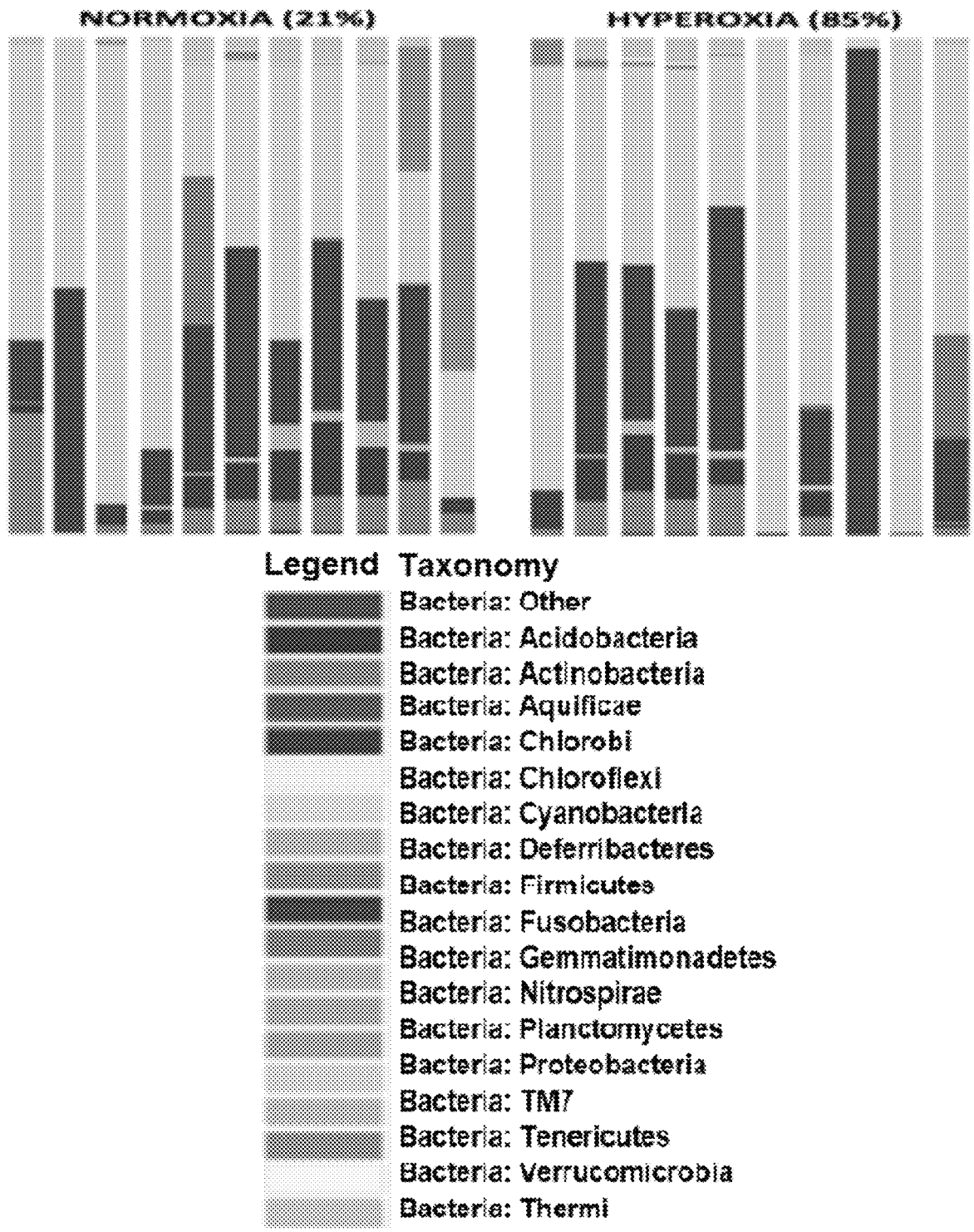

FIG. 17 illustrates that the baseline in vivo lung microbiome is not affected by hyperoxia exposure.

Figure 18:
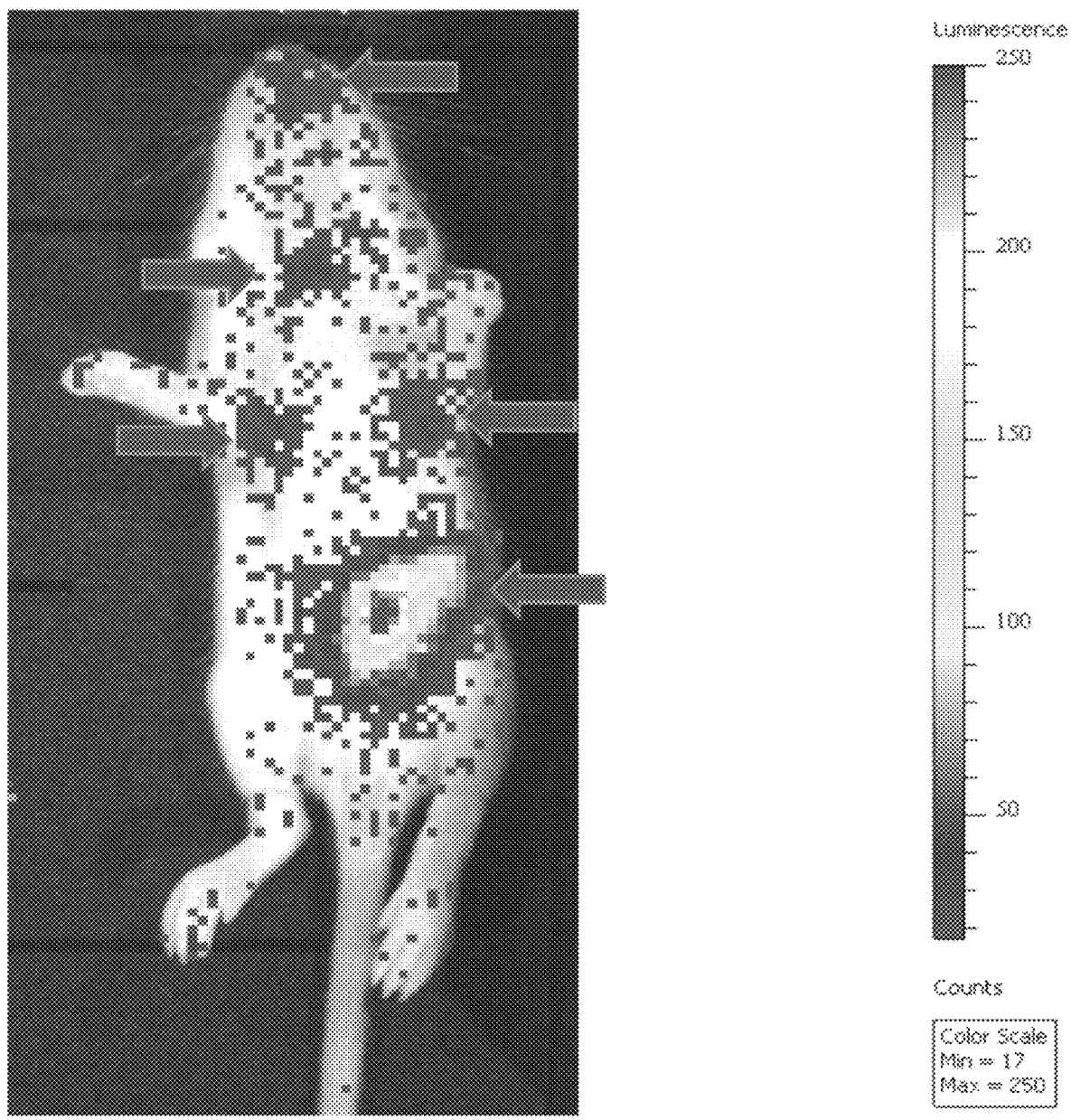

FIG. 18 illustrates bioluminescent imaging demonstrating deposition of nebulized bacteria in the mouth, trachea, lungs and stomach of the mice. This provides the proof of concept of the bacteria nebulization technique that we have developed.

Figure 19:
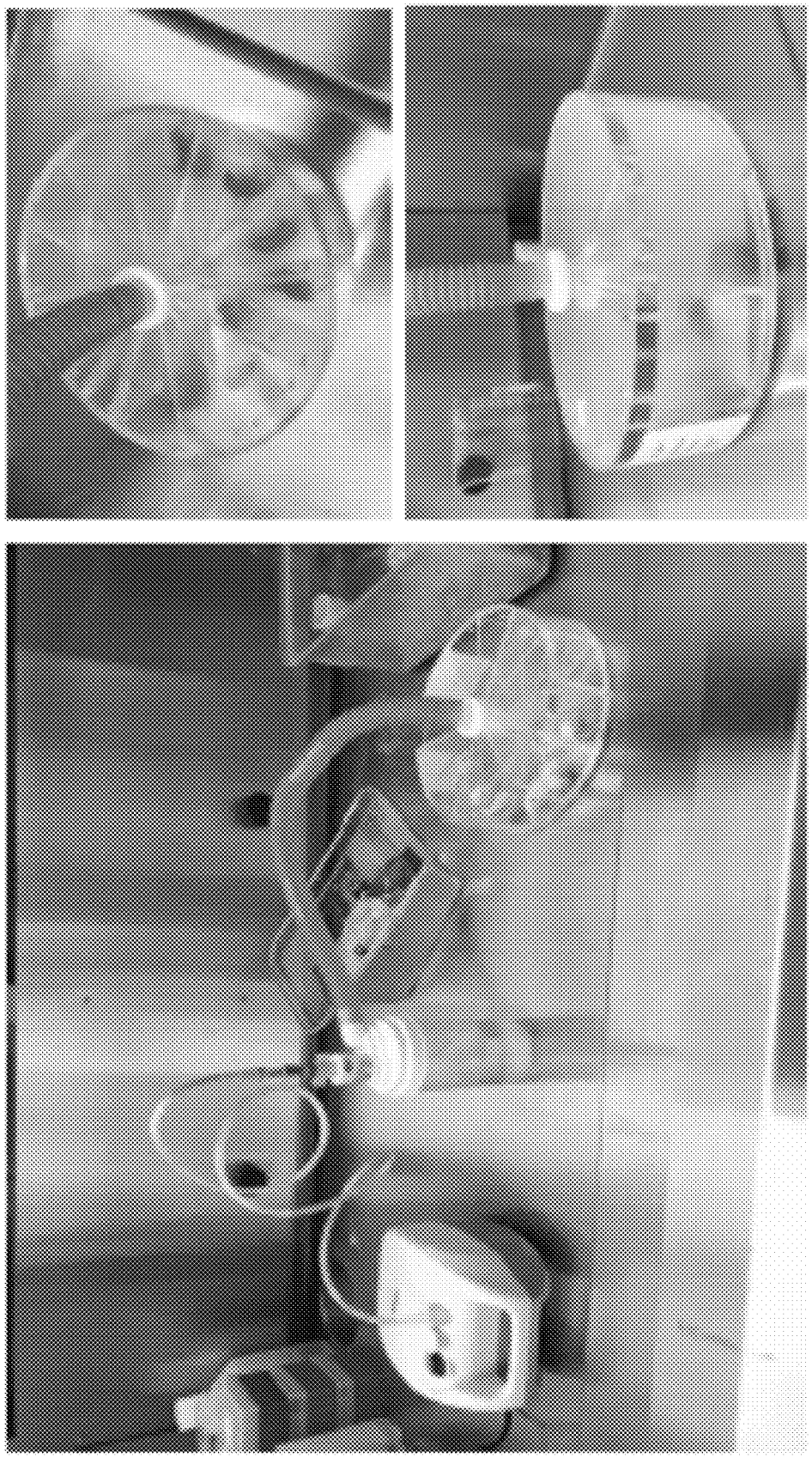

FIG. 19 illustrates an in vivo bacteria nebulizer experimental setup.

FIGS. 20A-20E are graphs illustrating the effects of *E. coli* and *Lactobacilli* combinations on cultured human bronchial epithelial cells (NHBE).

Figure 20A:
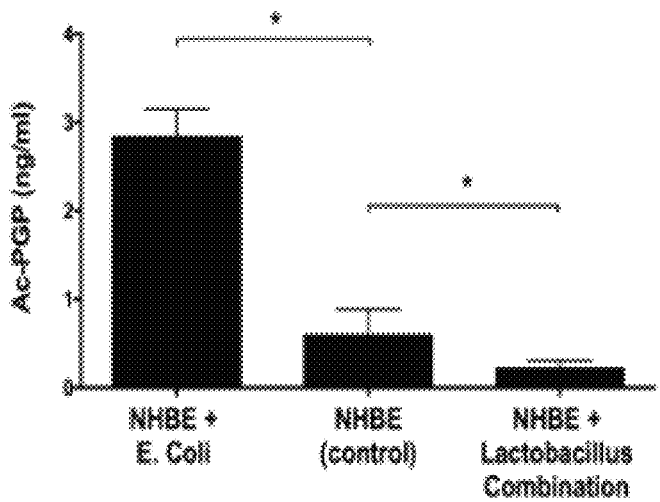

FIG. 20A illustrates Ac-PGP synthesis by NHBE cells in the presence of *E. coli* or *Lactobacilli* combinations.

Figure 20B:
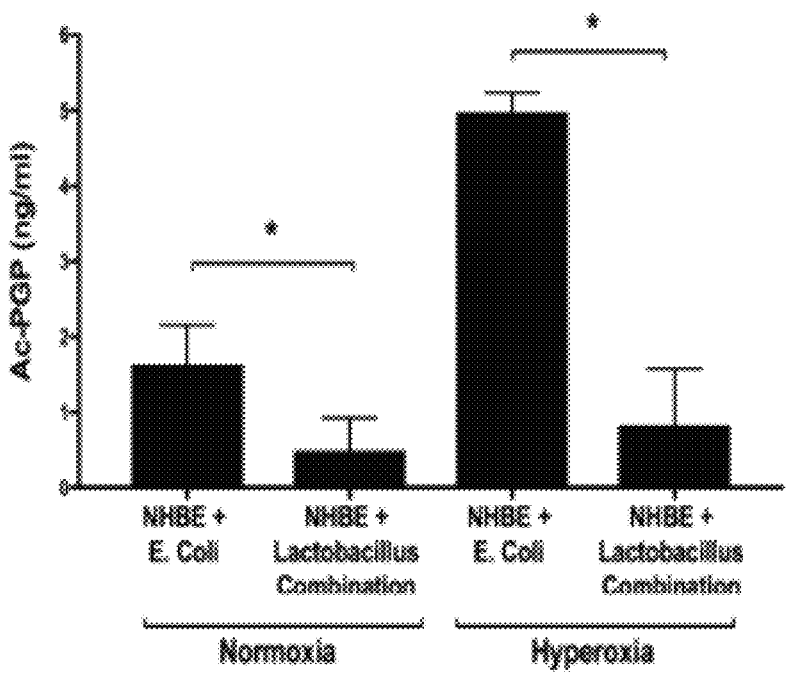

FIG. 20B illustrates Ac-PGP synthesis by NHBE cells in the presence of *E. coli* or *Lactobacilli* combinations under normoxia or hyperoxia conditions.

Figure 20C:
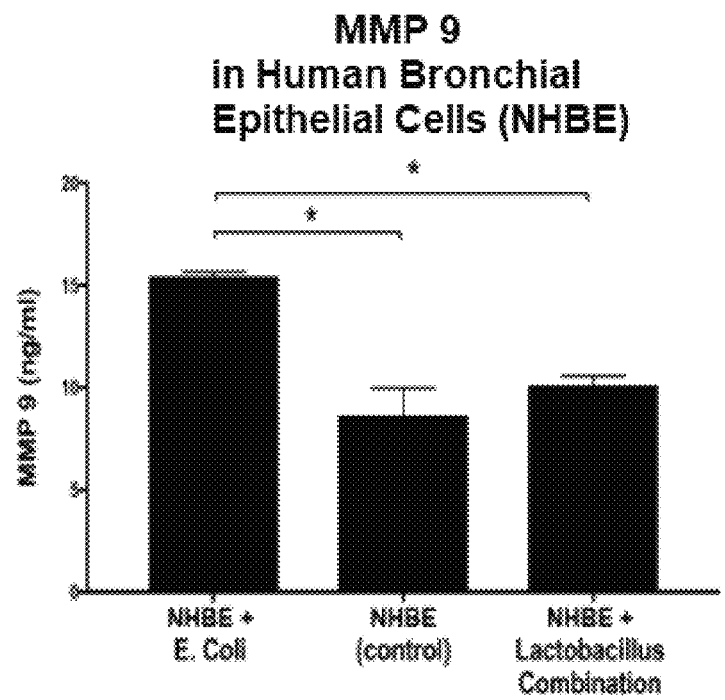

FIG. 20C illustrates MMP9 synthesis by NHBE cells in the presence of *E. coli* or *Lactobacilli* combinations.

Figure 20D:
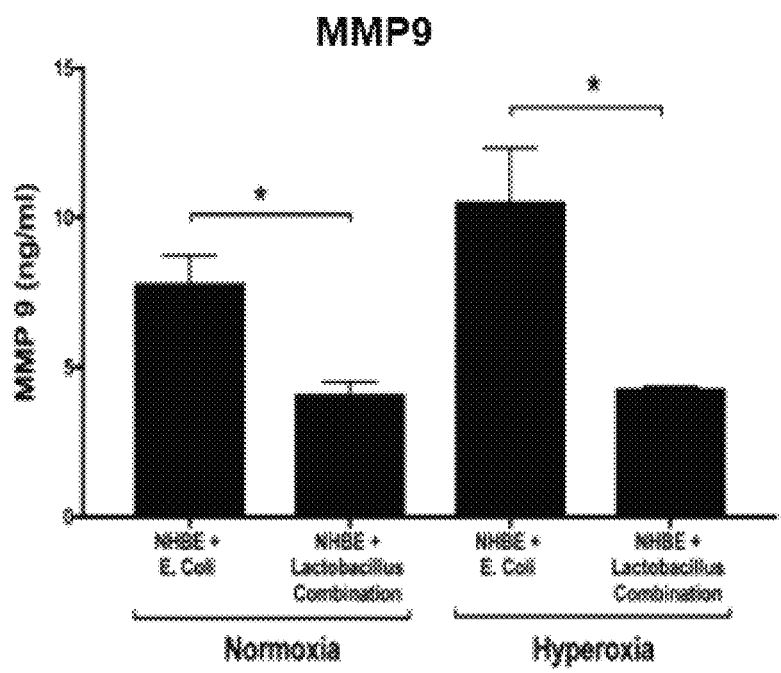

FIG. 20D illustrates MMP 9 synthesis by NHBE cells in the presence of *E. coli* or *Lactobacilli* combinations under normoxia or hyperoxia conditions.

Figure 20E:
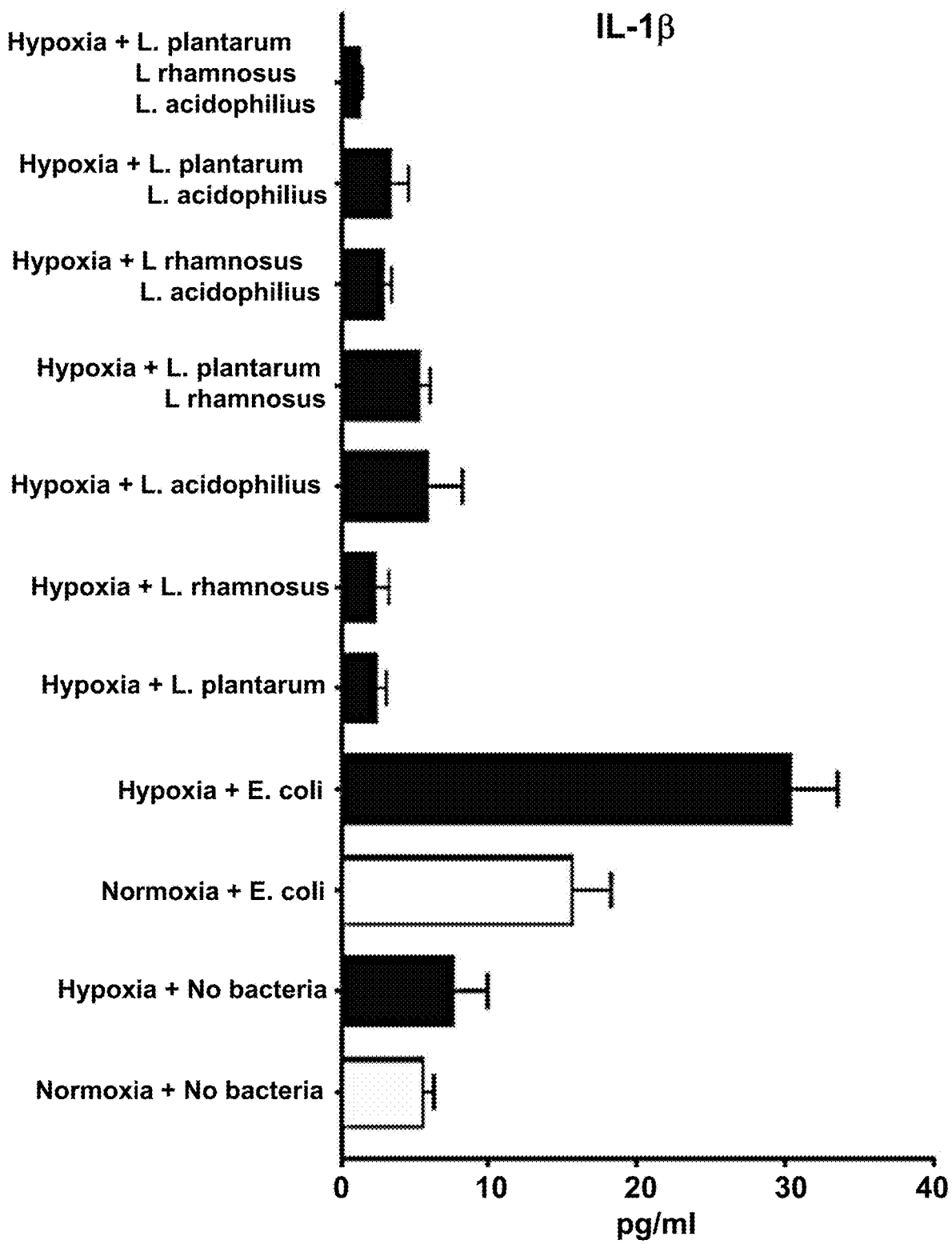

FIG. 20E illustrates IL-1β synthesis by NHBE cells in the presence of *E. coli* or *Lactobacilli* combinations under normoxia or hyperoxia conditions.

Figure 21:
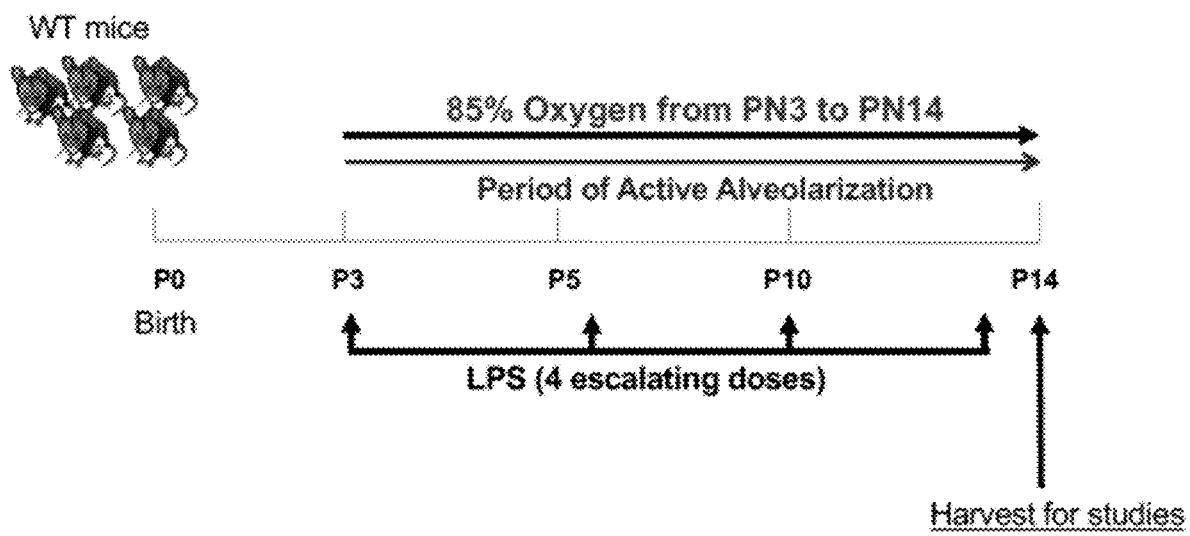

FIG. 21 schematically illustrates a postnatal model of lung injury in mice.

Figure 22:
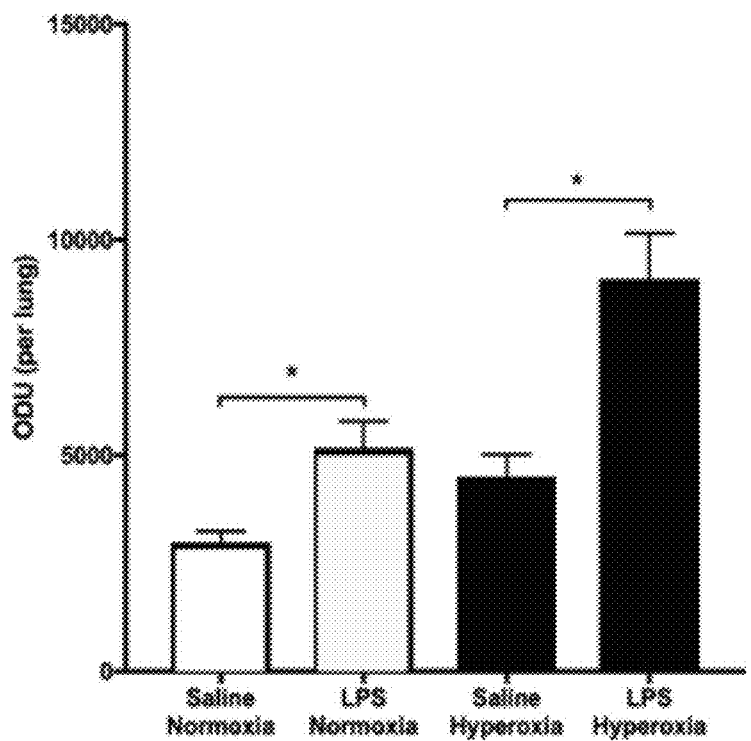
Figure 23A:
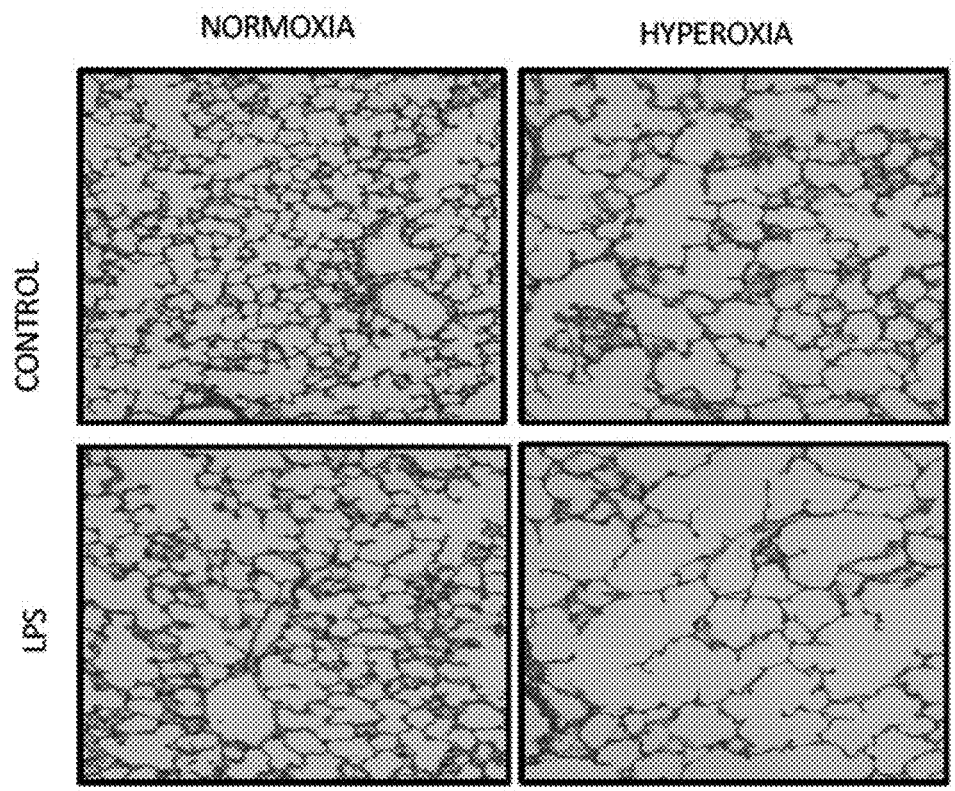
Figure 23B:
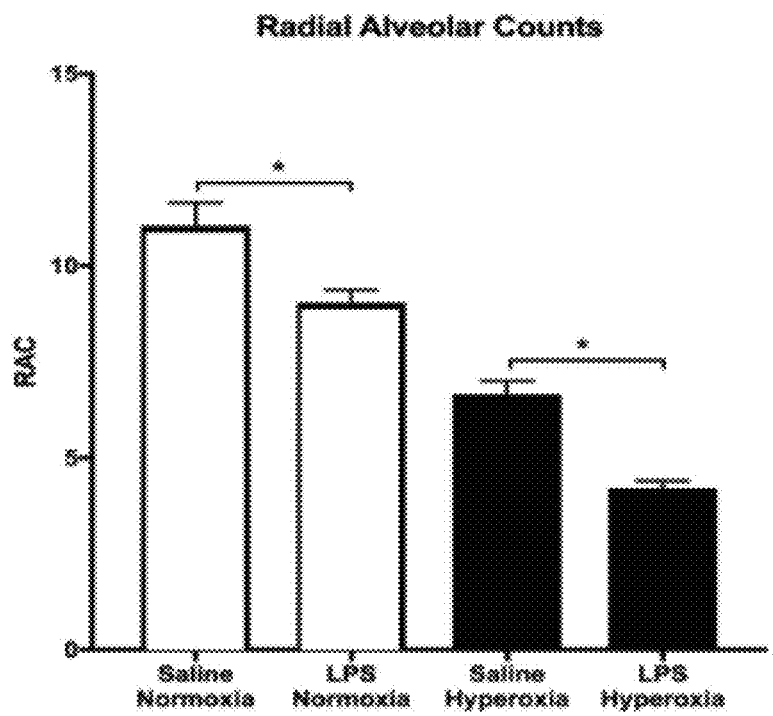
Figure 23C:
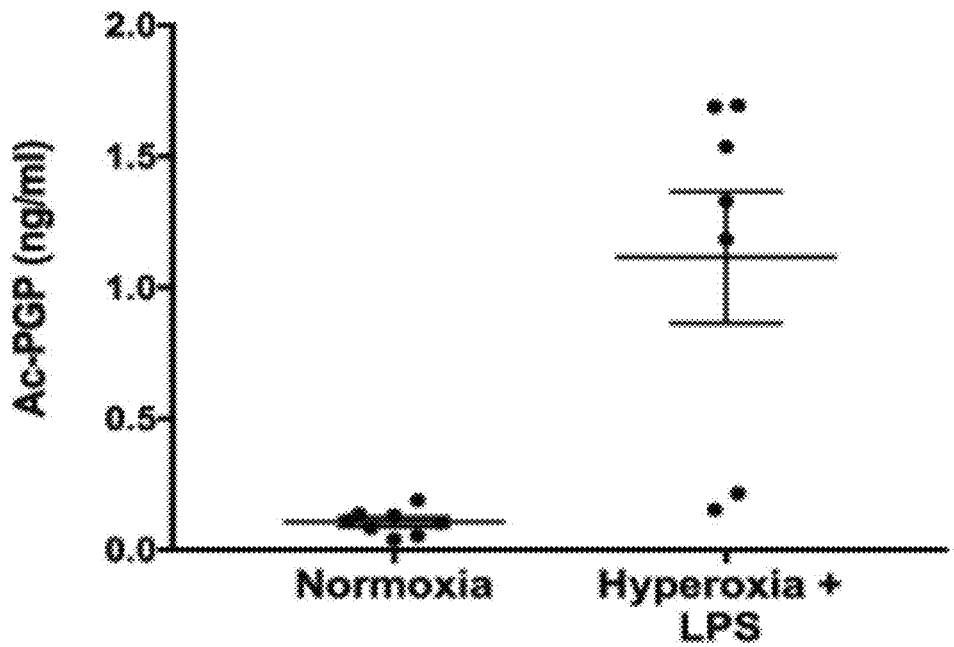
Figure 23D:
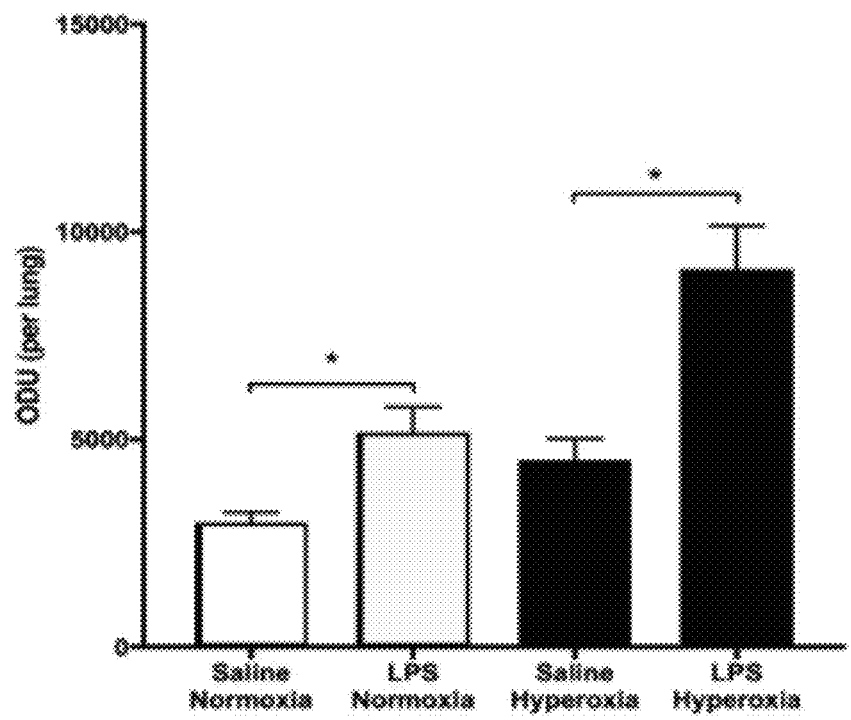
Figure 23E:
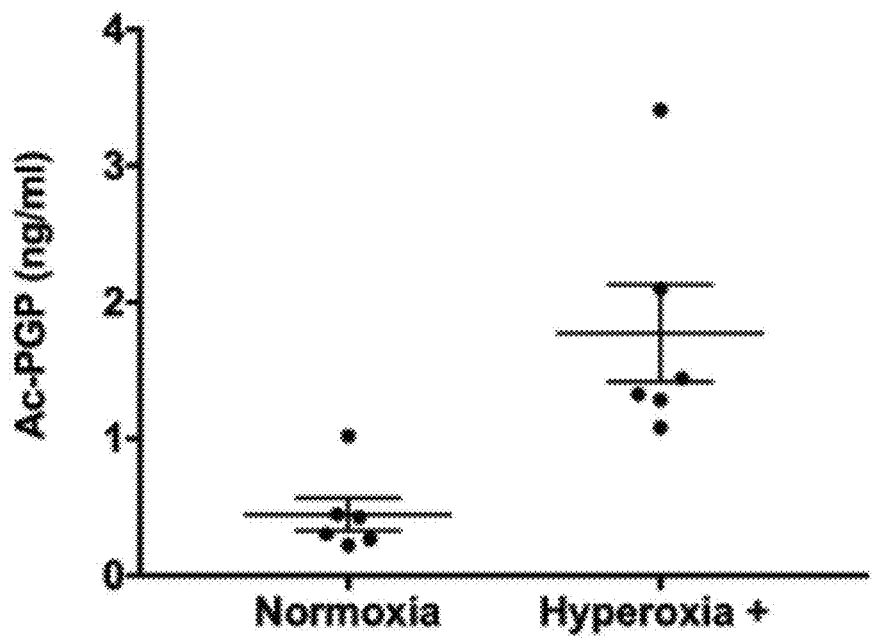
Figure 23F:
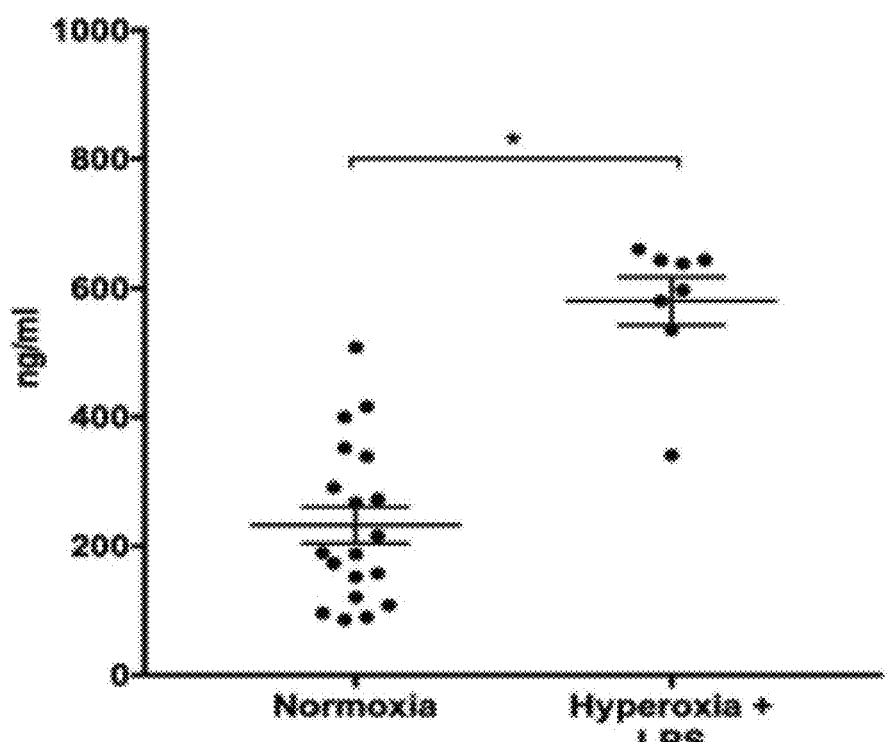
Figure 23G:
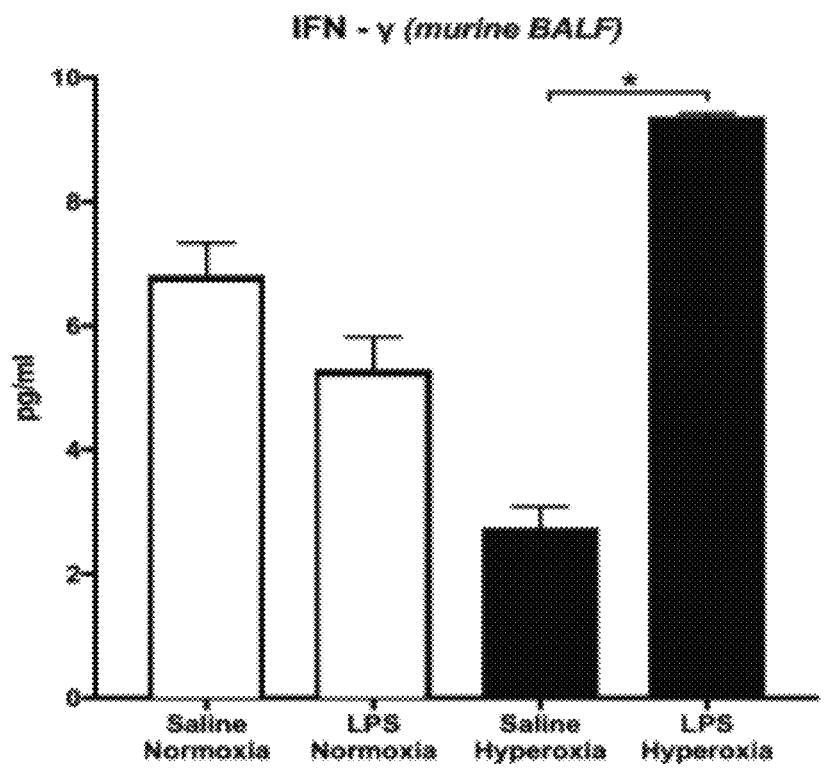
Figure 23H:
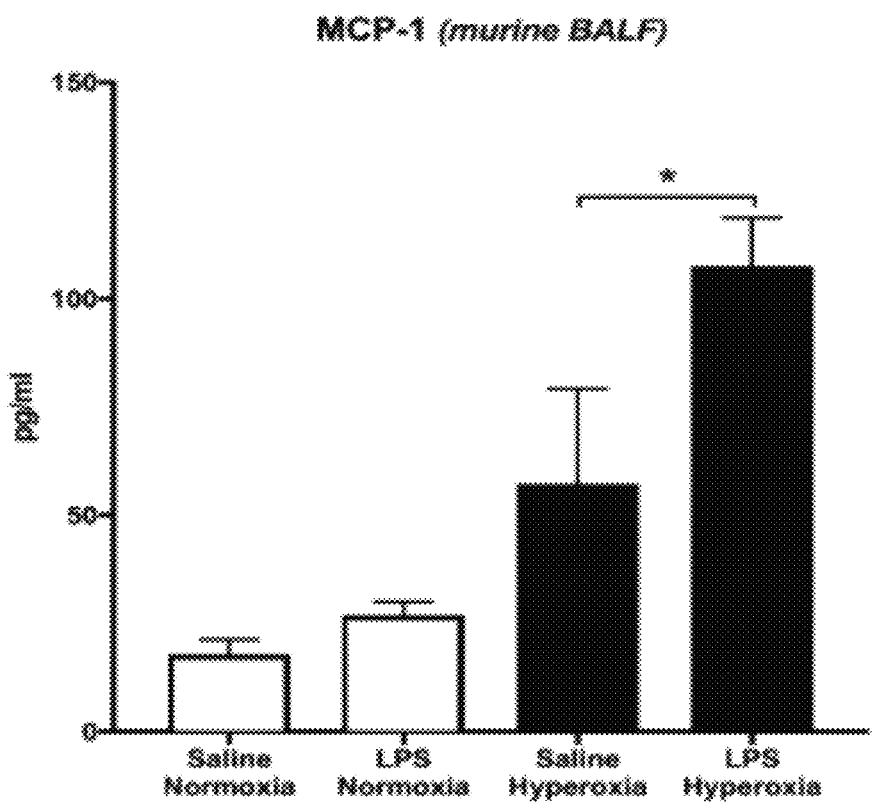
Figure 23I:
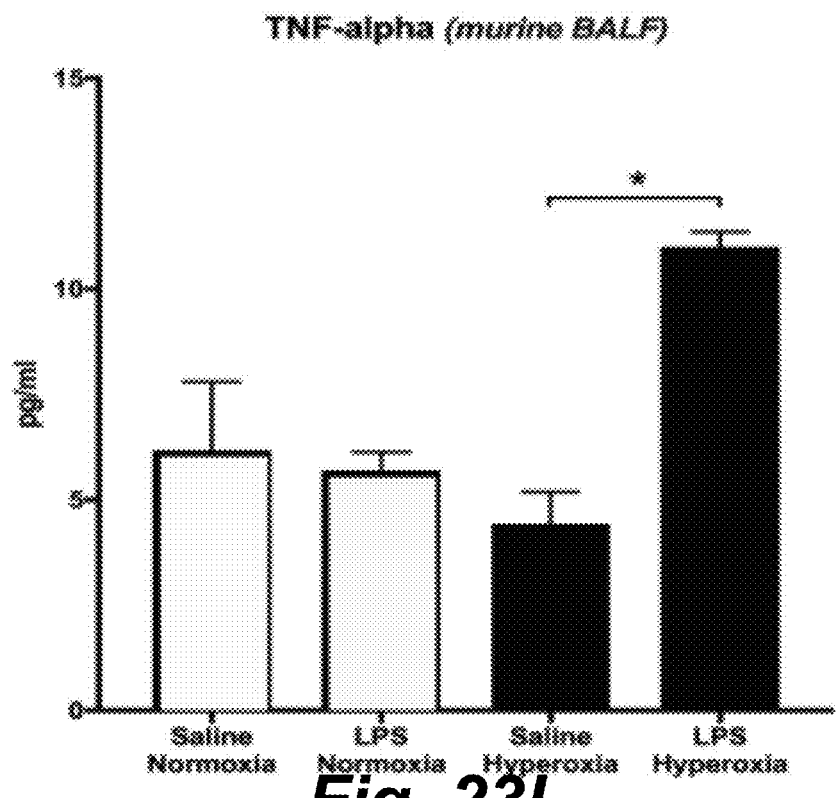
Figure 23J:
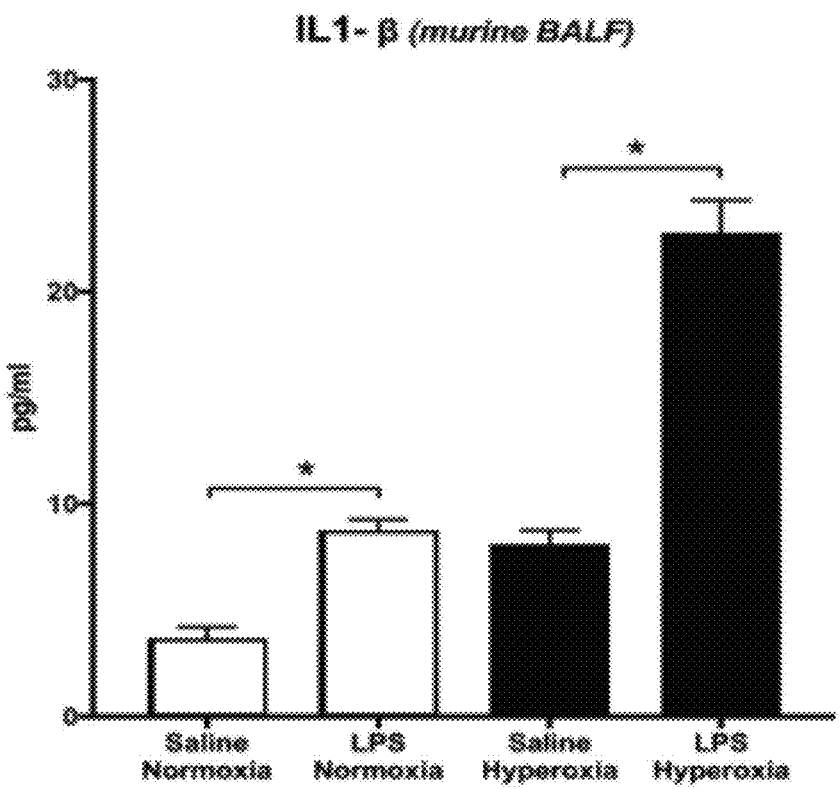
Figure 23K:
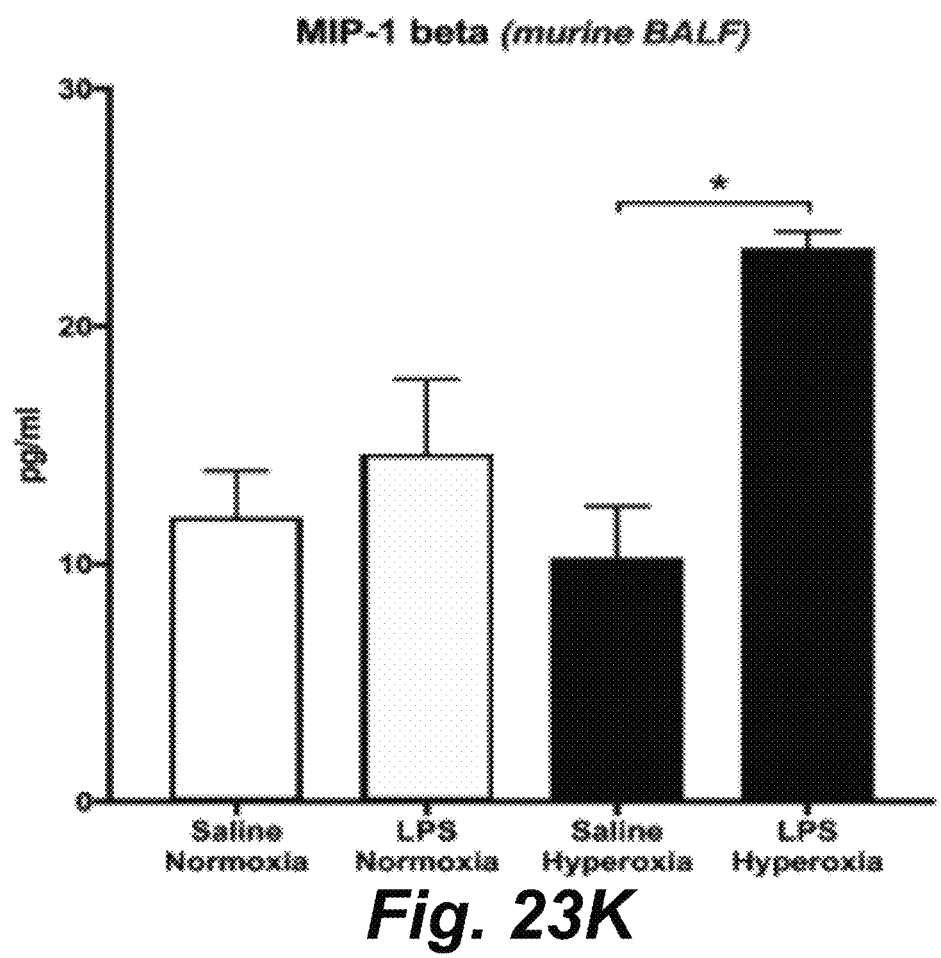

FIG. 22 is a graph illustrating that in vivo addition of *E. coli* LPS increases neutrophil activity in normoxia and hyperoxia.

FIGS. 23A-23K illustrate that in vivo addition of *E. coli* LPS causes severe alveolar hypoplasia under both normoxia and hyperoxia conditions in neonatal mice.

Figure 24:
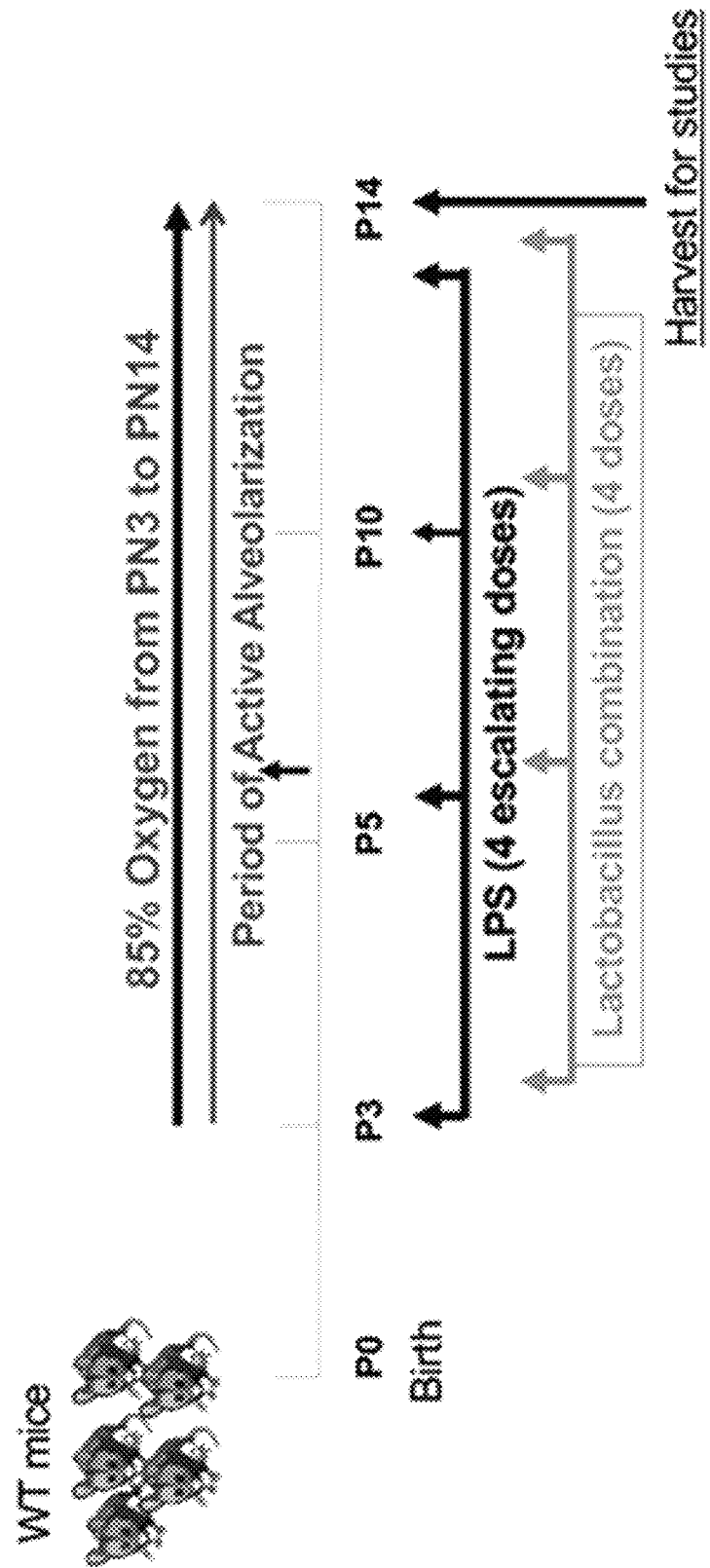

FIG. 24 schematically illustrates treatment with *Lactobacillus* combination.

Figure 25:
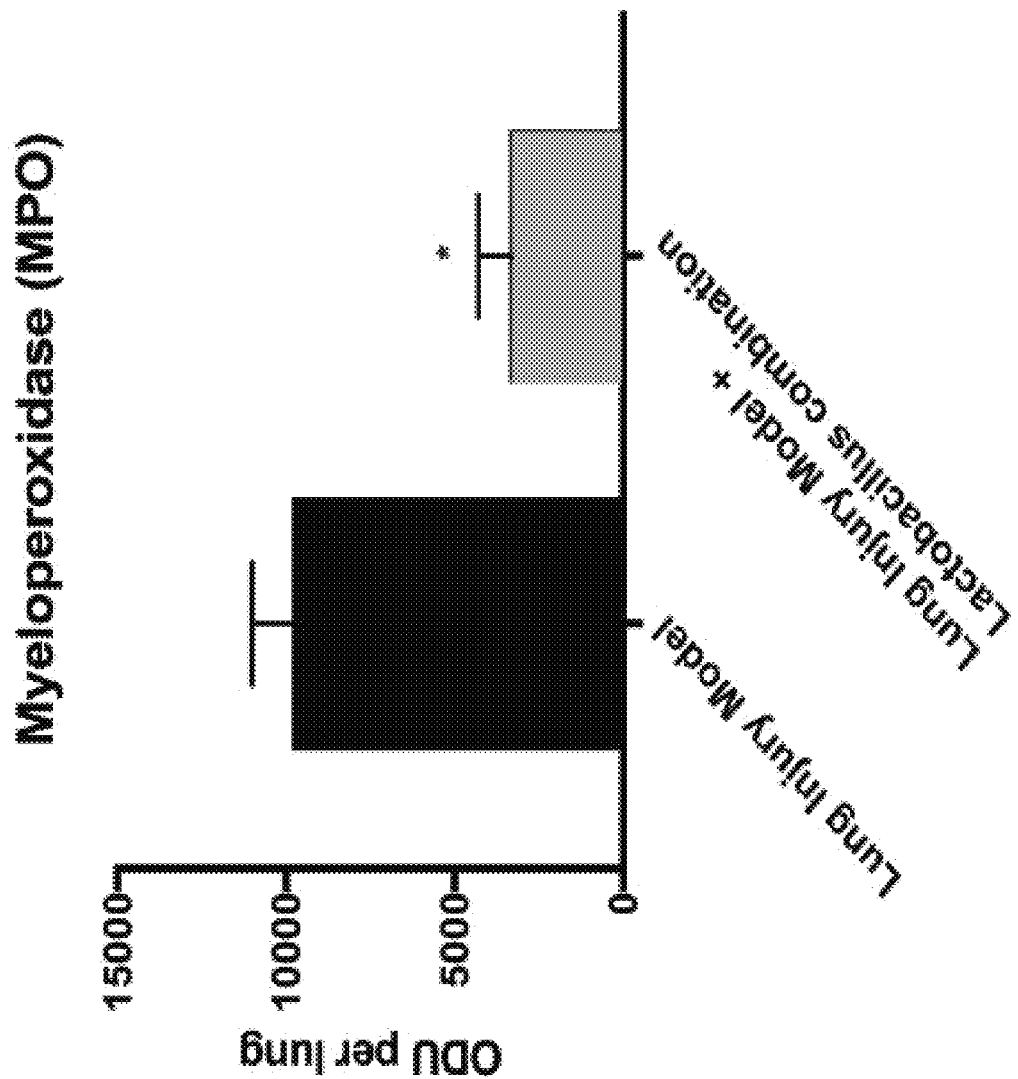

FIG. 25 is a graph illustrating the effect of in vivo treatment by the addition of a combination of *Lactobacilli* decreases neutrophilic inflammation (MPO) in the lung injury model.

FIGS. 26A and 26B illustrate that in vivo treatment by the addition of a combination of *Lactobacilli* improves lung functions (decreased resistance and improved compliance) in the lung injury model.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated.

Abbreviations

Bronchopulmonary Dysplasia, BPD; Chronic Obstructive Pulmonary Diseases, COPD; Cystic fibrosis, CF; Acute Respiratory Distress Syndrome, ARDS; Severe Acute Respiratory Syndrome, SARS; N-acetyl-Proline-Glycine-Proline, Ac-PGP; Human Bronchial Epithelial Cells, NHBE; Extremely low birth weight, ELBW; Full term, FT Definitions The terms "administering" and "administration" as used herein refer to a process by which a therapeutically effective amount of a compound of the disclosure or compositions contemplated herein are delivered to a subject for prevention and/or treatment purposes. Compositions are administered in accordance with good medical practices taking into account the subject's clinical condition, the site and method of administration, dosage, patient age, sex, body weight, and other factors known to physicians.

The term "bacterial population" as used herein refers to a homogeneous population of bacteria consisting of a single strain of a bacterial species or to a heterogeneous population of bacteria consisting of at least two distinguishable strains of a single bacterial species or of a plurality of species.

The term "bronchopulmonary disease" as used herein refers to a disease of the respiratory system, including the lungs and bronchial tree. Pulmonary diseases include, but are not limited to, cystic fibrosis, Chronic Obstructive Pulmonary Diseases (COPD), emphysema, asthma, sarcoidosis, chronic bronchitis, bronchopulmonary dysplasia, pulmonary fibrosis, pneumonia, and adult respiratory distress syndrome. The term "respiratory diseases", as used herein, means diseases or conditions related to the respiratory system. Examples include, but not limited to, airway inflammation, allergy (ies), asthma, impeded respiration, cystic fibrosis (CF), allergic rhinitis (AR), Acute Respiratory Distress Syndrome (ARDS), pulmonary hypertension, lung inflammation, bronchitis, airway obstruction, bronchoconstriction, microbial infection, and viral infection, such as SARS.

The term "child" as used herein refers to a human between the ages of about 0 and 12 years old. In certain embodiments, a child is between the ages of about 0 and 6 years old. In other embodiments, a child is between the ages of about 7 and 12 years old.

The terms "co-administration" or "co-administered" as used herein refer to the administration of at least two compounds or agent(s) or therapies to a subject. In some embodiments, the co-administration of two or more agents/therapies is concurrent. In other embodiments, a first agent/therapy is administered prior to a second agent/therapy in this aspect, each component may be administered separately, but sufficiently close in time to provide the desired effect, in particular a beneficial, additive, or synergistic effect. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

The term "composition" as used herein refers to a product comprising the specified ingredients in the specified amounts, as well as any product which results, directly or indirectly, from combination of the specified ingredients in the specified amounts. Such a term in relation to a pharmaceutical composition is intended to encompass a product comprising the active ingredient(s), and the inert ingredient(s) that make up the carrier, as well as any product which results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the present disclosure encompass any composition made by admixing a compound of the present disclosure and a pharmaceutically acceptable carrier.

When a compound of the present disclosure is used contemporaneously with one or more other drugs, a pharmaceutical composition containing such other drugs in addition to the compound of the present disclosure is contemplated. Accordingly, the pharmaceutical compositions of the present disclosure include those that also contain one or more other active ingredients, in addition to a compound of the present disclosure. The weight ratio of the compound of the present disclosure to the second active ingredient may be varied and will depend upon the effective dose of each ingredient. Generally, an effective dose of each will be used. Thus, for example, but not intended to be limiting, when a compound of the present disclosure is combined with another agent, the weight ratio of the compound of the present disclosure to the other agent will generally range from about 1000:1 to about 1:1000, preferably about 200:1 to about 1:200. Combinations of a compound of the present disclosure and other active ingredients will generally also be within the aforementioned range, but in each case, an effective dose of each active ingredient should be used. In such combinations the compound of the present disclosure and other active agents may be administered separately or in conjunction. In addition, the administration of one element may be prior to, concurrent to, or subsequent to the administration of other agent(s).

A composition of the disclosure can be a liquid solution, suspension, emulsion or a powder. Various delivery systems are known and can be used to administer a composition of the disclosure, e.g. encapsulation in liposomes, microparticles, microcapsules, and the like, and then delivered to a patient by means of such as a nebulizer.

Compositions for administration may include sterile aqueous or non-aqueous solvents, such as water, isotonic saline, isotonic glucose solution, buffer solution, or other solvents conveniently used for parenteral administration of therapeutically active agents, stabilizers, buffers, or preservatives, e.g. antioxidants such as methylhydroxybenzoate or similar additives.

A composition of the disclosure may be sterilized by, for example, addition of sterilizing agents to the composition, irradiation of the composition, or heating the composition. Alternatively, the compounds or compositions of the present disclosure may be provided as sterile solid preparations e.g. lyophilized powder, which are readily dissolved in sterile solvent immediately prior to use.

After pharmaceutical compositions have been prepared, they can be placed in an appropriate container and labeled for treatment of an indicated condition. For administration of a composition of the disclosure, such labeling would include amount, frequency, and method of administration.

The term "freeze-dried (lyophilized) as used herein refers to a preparation of bacterial cells that have been initially frozen and the water content removed by vacuum.

The terms "inactivated probiotic" or "inactivated microorganism" as used herein mean that the metabolic activity or reproductive ability of the organism has been reduced or destroyed. The inactivated organisms do, however, still retain, at the cellular level, at least a portion their biological glycol-protein and DNA/RNA structure. As used herein, the term "inactivated" is synonymous with "non-viable".

The term "infant" as used herein refers to a human that is less than about 1 year old.

The term "*Lactobacillus*" as used herein refers to a genus of Gram-positive, facultative anaerobic or microaerophilic, rod-shaped, non-spore-forming bacteria. They are a major part of the lactic acid bacteria group (i.e. they convert sugars to lactic acid). *Lactobacillus* species include *Lactobacillus acetotolerans, Lactobacillus acidifarinae, Lactobacillus acidipiscis, Lactobacillus acidophilus* (*Doderlein bacillus*), *Lactobacillus agilis, Lactobacillus algidus, Lactobacillus alimentarius, Lactobacillus amylolyticus, Lactobacillus amylophilus, Lactobacillus amylotrophicus, Lactobacillus amylovorus, Lactobacillus animalis, Lactobacillus antri, Lactobacillus apodemi, Lactobacillus aviarius, Lactobacillus bifermentans, Lactobacillus brevis, Lactobacillus buchneri, Lactobacillus camelliae, Lactobacillus casei, Lactobacillus catenaformis, Lactobacillus ceti, Lactobacillus coleohominis, Lactobacillus collinoides, Lactobacillus composti, Lactobacillus concavus, Lactobacillus coryniformis, Lactobacillus crispatus, Lactobacillus crustorum, Lactobacillus curvatus, Lactobacillus delbrueckii, Lactobacillus delbrueckii* subsp. *Bulgaricus, Lactobacillus delbrueckii* subsp. *Lactis, Lactobacillus diolivorans, Lactobacillus equi, Lactobacillus equigenerosi, Lactobacillus farraginis, Lactobacillus farciminis, Lactobacillus fermentum, Lactobacillus fornicalis, Lactobacillus fructivorans, Lactobacillus frumenti, Lactobacillus fuchuensis, Lactobacillus gallinarum, Lactobacillus gasseri, Lactobacillus gastricus, Lactobacillus ghanensis, Lactobacillus graminis, Lactobacillus hammesii, Lactobacillus hamsteri, Lactobacillus harbinensis, Lactobacillus hayakitensis, Lactobacillus helveticus, Lactobacillus hilgardii, Lactobacillus homohiochii, Lactobacillus iners, Lactobacillus ingluviei, Lactobacillus intestinalis, Lactobacillus jensenii, Lactobacillus johnsonii, Lactobacillus kalixensis, Lactobacillus kefiranofaciens, Lactobacillus kefiri, Lactobacillus kimchii, Lactobacillus kitasatonis, Lactobacillus kunkeei, Lactobacillus leichmannii, Lactobacillus lindneri, Lactobacillus malefermentans, Lactobacillus mali, Lactobacillus manihotivorans, Lactobacillus mindensis, Lactobacillus mucosae, Lactobacillus murinus, Lactobacillus nagelii, Lactobacillus namurensis, Lactobacillus nantensis, Lactobacillus oligofermentans, Lactobacillus oris, Lactobacillus panis, Lactobacillus pantheris, Lactobacillus parabrevis, Lactobacillus parabuchneri, Lactobacillus paracollinoides, Lactobacillus parafarraginis, Lactobacillus parakefiri, Lactobacillus paralimentarius, Lactobacillus paraplantarum, Lactobacillus pentosus, Lactobacillus perolens, Lactobacillus plantarum, Lactobacillus pontis, Lactobacillus psittaci, Lactobacillus rennini, Lactobacillus reuteri, Lactobacillus rhamnosus, Lactobacillus rimae, Lactobacillus rogosae, Lactobacillus rossiae, Lactobacillus ruminis, Lactobacillus saerimneri, Lactobacillus sakei, Lactobacillus salivarius, Lactobacillus sanfranciscensis, Lactobacillus satsumensis, Lactobacillus secaliphilus, Lactobacillus sharpeae, Lactobacillus siliginis, Lactobacillus spicheri, Lactobacillus suebicus, Lactobacillus thailandensis, Lactobacillus ultunensis, Lactobacillus vaccinostercus, Lactobacillus vaginalis, Lactobacillus versmoldensis, Lactobacillus vini, Lactobacillus vitulinus, Lactobacillus zeae,* and *Lactobacillus zymae*, and strains thereof. A preferred embodiment of the disclosure consists essentially of at least one strain of at least one of the *Lactobacillus* species *Lactobacillus plantarum, Lactobacillus paracasei, Lactobacillus acidophilus* and *Lactobacillus rhamnosus*.

The term "pharmaceutically acceptable carrier" as used herein refers to a diluent, adjuvant, excipient, or vehicle with which a probe of the disclosure is administered and which is approved by a regulatory agency of the Federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. When administered to a patient, the probe and pharmaceutically acceptable carriers can be sterile. Water is a useful carrier when the probe is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use.

The term "preterm" as used herein refers to an infant born before the end of the 37th week of gestation.

The term "preventing" means to stop or hinder a disease, disorder, or symptom of a disease or condition through some action.

The term "probiotic" is recognized in the state of the art as a microorganism which, when administered in adequate amounts, confers a health benefit to the host. A probiotic microorganism must fulfil several requirements related to lack of toxicity, viability, adhesion and beneficial effects. These probiotic features are strain-dependent, even among bacteria of the same species. Therefore, it is important to find those strains that have a better performance in all probiotic requirements.

The term "reducing" means to diminish in extent, amount, or degree.

The term "therapeutic agent" as used herein refers to a therapeutic substance selected from a group consisting of, but not limited to, analgesics, anesthetics, anti-inflammatory agents, antiasthma agents, antibiotics (including penicillins), anticoagulants, antihistamines, antitussives, antihypertensive agents, antimuscarinic agents, antimycobacterial agents, antioxidant agents, antipyretics, immunosuppressants, immunostimulants, antiviral agents, bacteriostatic agents, bronchodilators, buffering agents, contrast media, corticosteroids, cough suppressants (expectorants and mucolytics), diagnostic agents, diagnostic imaging agents, free radical scavenging agents, growth factors, haemostatics, immunological agents, lipid regulating agents, muscle relaxants, proteins, peptides and polypeptides, prostaglandins, radio-pharmaceuticals, time release binders, anti-allergic agents, stimulants and anoretics, steroids, sympathomimetics, vasodilators, and xanthines.

The terms "treating" or "treatment" as used herein refers to an alleviation of symptoms associated with a disorder or disease, or inhibition of further progression or worsening of those symptoms, or prevention or prophylaxis of the disease or disorder, or curing the disease or disorder. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount of a therapy (e.g., a prophylactic or therapeutic agent) that is sufficient to reduce or ameliorate the severity and/or duration of a respiratory condition or one or more symptoms thereof, prevent the advancement of a respiratory condition, cause regression of a respiratory condition, prevent the recurrence, development, or onset of one or more symptoms associated with a respiratory condition, or enhance or improve the prophylactic or therapeutic effect(s) of another therapy (e.g., prophylactic or therapeutic agent).

DESCRIPTION

The present disclosure encompasses embodiments of a probiotic pharmaceutical composition that delivers strains of *Lactobacillus* to the epithelial lining of the respiratory tract of human subjects to relieve inflammation and other pathological conditions of bronchopulmonary dysplasia. The probiotic compositions of the disclosure comprise at least one strain of *Lactobacillus* that may be either a live organism capable of proliferation in the subject patient, a non-living strain such as, but not limited to, a heat-killed non-proliferative strain, or a combination of proliferative and non-proliferative populations of a strain. It is further contemplated that the compositions of the disclosure may comprise a plurality of strains of the same *Lactobacillus* species or a plurality of species, each of which may be proliferative or non-proliferative. In some embodiments of the compositions of the disclosure, additional bacterial species or strains thereof may be included with the *Lactobacillus*.

In addition, the disclosure encompasses embodiments of a method of reducing symptoms associated with bronchopulmonary dysplasia by administering to a patient in need a volume of a probiotic composition as herein described. The composition Alterations of pulmonary microbiome have been recognized in multiple respiratory disorders. It is critically important to ascertain if an airway microbiome exists at birth and if so, whether it is associated with subsequent lung disease. Found was an established diverse and similar airway microbiome at birth in both preterm and term infants, which was more diverse and different from that of older preterm infants with established chronic lung disease (bronchopulmonary dysplasia). Consistent temporal dysbiotic changes in the airway microbiome were seen from birth to the development of bronchopulmonary dysplasia in extremely preterm infants. Genus *Lactobacillus* was decreased at birth in infants with chorioamnionitis and in preterm infants who subsequently went on to develop lung disease. The results, taken together with previous literature indicating a placental and amniotic fluid microbiome, suggest fetal acquisition of an airway microbiome. The early airway microbiome may prime the developing pulmonary immune system, and dysbiosis in its development may set the stage for subsequent lung disease.

It was hypothesized that an airway microbiome is present at birth, and that the airway microbiota at birth would differ between extremely low birth weight (ELBW) preterm infants (less than 1 Kg birth weight) and full term (FT) infants, and would change over time in preterm infants who go on to develop BPD. It was also hypothesized that early (at birth) airway microbiota would differ in ELBW infants who later go on to develop BPD from the ones who are resilient to the disease. It has been found that a diverse airway microbiome at birth with prognostic potential that becomes dysregulated during development of BPD Bronchopulmonary dysplasia (BPD), Cystic fibrosis (CF), Chronic Obstructive Pulmonary Disease (COPD) and Acute Respiratory Distress Syndrome (ARDS) are chronic lung diseases spanning from infancy to old age. Together these respiratory diseases effect more than 25 million Americans each year. The common problem in all these respiratory conditions is inflammation initiated by injury to the immature lung by early neutrophil influx, followed by a persistent inflammatory process and extracellular matrix (ECM) remodeling, resulting in impaired lungs. It has now been discovered that airways are not sterile even at birth but are occupied by a diverse microbiome, and that the airway microbiome is altered (dysbiosis) during the development of lung disease. The study of microbiome is a novel and new field, but less has been studied about the lung microbiome. It has been established that the tri peptide N-acetyl-proline-glycine-proline (Ac-PGP) derived from ECM breakdown plays a critical role in various adult chronic lung diseases by enhancing neutrophilic inflammation and endothelial permeability. Bacteria drive Ac-PGP release. We have discovered that, the inflammatory cascade shown in FIG. 1 is prevented by *Lactobacillus*. It is contemplated, therefore, that probiotic-*Lactobacillus* reduces the inflammation of lungs in various lung diseases by inhibition of neutrophilic inflammation.

Data indicates that probiotic *Lactobacillus* species inhibit inflammation in in vitro and animal models of chronic lung diseases. Accordingly, the present disclosure encompasses embodiments of an inhaled probiotic therapy that may be delivered by such means as, but not limited to, a nebulization or meter dose inhaler for the treatment of bronchopulmonary pathologies as BPD, COPD, CF and ARDS. The probiotic therapy would include a combination of various *Lactobacillus* species such as *Lactobacillus plantarum*, *Lactobacillus paracasei*, *Lactobacillus acidophilus* and *Lactobacillus rhamnosus* to form a mega probiotic mixture. Formulations: one with live bacteria and the other with heat inactivated bacteria are contemplated. A third formulation with would include an antioxidant along with probiotic.

Embodiments of combinations of *Lactobacilli* species advantageous in the methods of the disclosure are given, but not limited to, those in Table 1. Other species of *Lactobacilli*, identifiable in the bronchopulmonary microbiome of neonates may also be usefully employed, alone or in combination with those of Table 1.

TABLE 1

Examples of *Lactobacilli* combinations for use in the methods and compositions of the disclosure

| Lactobacilli combination | *Lactobacillus plantarum* | *Lactobacillus paracasei* | *Lactobacillus acidophilus* | *Lactobacillus rhamnosus* |
|---|---|---|---|---|
| 1 | + | − | − | − |
| 2 | − | + | − | − |
| 3 | − | − | + | − |
| 4 | − | − | − | + |
| 5 | + | + | − | − |
| 6 | + | − | + | − |
| 7 | + | − | − | + |
| 8 | − | + | + | − |
| 9 | − | + | − | + |
| 10 | − | − | + | + |
| 11 | + | + | + | − |
| 12 | + | + | − | + |
| 13 | + | − | + | + |
| 14 | − | + | + | + |
| 14 | + | + | + | + |

One example of a composition of the disclosure is, but not limited to, the strains *Lactobacillus rhamnosus* ATCC 53103, *Lactobacillus plantarum* wcfs1 ATCC BAA-793, and *Lactobacillus acidophilus* ATCC 4356. In all combinations as shown, for example, in Table 1, one or more of the bacterial strains may be non-viable, particularly heat-killed and one or more of the strains may be viable and able to colonize the bronchopulmonary tissues of the recipient subject.

In general the composition of the present invention can contain non-replicating probiotic microorganisms in a therapeutically effective dose and/or in a prophylactic effective dose. In prophylactic applications, compositions according to the invention are administered to a person susceptible to or otherwise at risk of a disorder in an amount that is sufficient to at least partially reduce the risk of developing that disorder. Such an amount is defined to be "a prophylactic effective dose". Again, the precise amounts depend on a number of factors such as the child's state of health and weight. Those skilled in the art will be able to adjust the therapeutically effective dose and/or the prophylactic effective dose appropriately. Typically, the therapeutically effective dose and/or the prophylactic effective dose is in the range of about 0.005 mg-1000 mg non-replicating, probiotic micro-organisms per daily dose. Preferably the non-replicating micro-organisms are present in an amount equivalent to between $10^4$ to $10^9$ cfu/g of dry composition, even more preferably in an amount equivalent to between $10^5$ and $10^9$ cfu/g of dry composition.

In terms of numerical amounts, the "short-time high temperature" treated non-replicating micro-organisms may be present in the composition in an amount corresponding to between $10^4$ and $10^{12}$ equivalent cfu/g of the dry composition. Obviously, non-replicating micro-organisms do not form colonies, consequently, this term is to be understood as the amount of non-replicating micro-organisms that is obtained from $10^4$ and $10^{12}$ cfu/g replicating bacteria. This includes micro-organisms that are inactivated, non-viable or dead or present as fragments such as or cell wall or cytoplasmic compounds. In other words, the quantity of micro-organisms which the composition contains is expressed in terms of the colony forming ability (cfu) of that quantity of micro-organisms as if all the micro-organisms were alive irrespective of whether they are, in fact, non-replicating, such as inactivated or dead, fragmented or a mixture of any or all of these states.

The probiotics may be rendered non-replicating by any method that is known in the art. The technologies available today to render probiotic strains non-replicating are usually heat-treatment, .gamma.-irradiation, UV light or the use of chemical agents (formalin, paraformaldehyde). It may be convenient, to be able to heat treat the probiotic micro-organisms of the disclosure either together so that the probiotics retain or improve their beneficial properties.

Heat treatment may be carried out at least at 71.5° C. for at least 1 second. Long-term heat treatments or short-term heat treatments may also be used. Hence, for example, the heat treatment may be a high temperature treatment at about 71.5-150° C. for about 1-120 seconds. More preferred the micro-organisms may be subjected to a high temperature treatment at about 90-140° C., for example 90-120° C., for a short term of about 1-30 secs. This high temperature treatment renders the micro-organisms at least in part non-replicating.

The high temperature treatment may be carried out at normal atmospheric pressure but may be also carried out under high pressure. Typical pressure ranges are from 1 to 50 bar, preferably from 1-10 bar, even more preferred from 2 to 5 bar. Obviously, it is preferred if the probiotics are heat treated in a medium that is either liquid or solid, when the heat is applied. An ideal pressure to be applied will therefore depend on the nature of the composition which the micro-organisms are provided in and on the temperature used. Depending on the nature and amount of the composition the micro-organisms are provided in and depending on the architecture of the heating apparatus used, the time of heat application may differ.

According to the disclosure, a kit is also provided. In an aspect, the kit comprises a compound of the disclosure or a formulation of the disclosure in kit form. The kit can be a package which houses a container which contains compounds of the disclosure or formulations of the disclosure and also houses instructions for administering the compounds or formulations to a subject. The disclosure further relates to a commercial package comprising compounds of the disclosure or formulations of the disclosure together with instructions for simultaneous, separate or sequential use. In particular a label may include amount, frequency, and method of administration.

The disclosure also provides a pharmaceutical pack or kit comprising one or more containers filled with one or more of the ingredients of a composition of the disclosure to provide a therapeutic effect. Associated with such container(s) can be various written materials such as instructions for use, or a notice in the form prescribed by a governmental agency regulating the labeling, manufacture, use or sale of pharmaceuticals or biological products, which notice reflects approval by the agency of manufacture, use, or sale for human administration.

The disclosure also relates to articles of manufacture and kits containing materials useful for treating a disease disclosed herein. An article of manufacture may comprise a container with a label. Examples of suitable containers include bottles, vials, and test tubes, or a delivery device such as a nebulizer, which may be formed from a variety of materials including glass and plastic. A container holds compounds of the disclosure or formulations of the disclosure which are effective for treating a disease disclosed herein. The label on the container indicates that the compounds of the disclosure or formulations of the disclosure are used for treating a disease disclosed herein and may also indicate directions for use. In aspects of the disclosure, a medicament or formulation in a container may comprise any of the medicaments or formulations disclosed herein.

The disclosure also contemplates kits comprising one or more of compounds of the disclosure. In aspects of the disclosure, a kit of the disclosure comprises a container described herein. In particular aspects, a kit of the disclosure comprises a container described herein and a second container comprising a buffer. A kit may additionally include other materials desirable from a commercial and user standpoint, including, without limitation, buffers, diluents, filters, needles, syringes, and package inserts with instructions for performing any methods disclosed herein (e.g., methods for treating a disease disclosed herein). A medicament or formulation in a kit of the disclosure may comprise any of the formulations or compositions disclosed herein.

The compositions and methods described herein are indicated as therapeutic agents or methods either alone or in conjunction with other therapeutic agents or other forms of treatment. They may be co-administered, combined or formulated with one or more therapies or agents used to treat a condition described herein. Compositions of the disclosure may be administered concurrently, separately, or sequentially with other therapeutic agents or therapies. Therefore, compounds of the disclosure may be co-administered with one or more additional therapeutic agents for the treatment of complications resulting from or associated with a disease disclosed herein, or general medications that treat or prevent side effects.

One aspect of the disclosure encompasses a pharmaceutical composition comprising a bacterial population comprising at least one *Lactobacillus* species.

In some embodiments of this aspect of the disclosure, the bacterial population may comprise at least one *Lactobacillus* species selected from the group consisting of *Lactobacillus plantarum, Lactobacillus paracasei, Lactobacillus acidophilus* and *Lactobacillus rhamnosus*.

In some embodiments of this aspect of the disclosure, the bacterial population can consist of *Lactobacillus plantarum, Lactobacillus acidophilus* and *Lactobacillus rhamnosus*.

In some embodiments of this aspect of the disclosure, at least one of the *Lactobacillus* species is not capable of proliferating in the recipient patient.

In some embodiments of this aspect of the disclosure, at least one of the *Lactobacillus* species is heat-killed.

In some embodiments of this aspect of the disclosure, at least one of the *Lactobacillus* species is viable and capable of proliferating in the recipient patient.

In some embodiments of this aspect of the disclosure, the bacterial population is freeze-dried.

In some embodiments of this aspect of the disclosure, the pharmaceutical composition can further comprise at least one therapeutic agent, wherein said agent or agents can reduce at least one symptom or pathological effect of a bronchopulmonary disease.

In some embodiments of this aspect of the disclosure, the therapeutic agent can be selected from the group consisting of: an anti-inflammatory agent or an anti-oxidant.

In some embodiments of this aspect of the disclosure, the bacterial population can be suspended in a pharmaceutically acceptable carrier.

In some embodiments of this aspect of the disclosure, the pharmaceutical composition is formulated for administration to the respiratory tract of a patient by nasal spray delivery.

In some embodiments of this aspect of the disclosure, the pharmaceutical composition can be formulated for administration to the respiratory tract of a patient by a nebulizer.

Another aspect of the disclosure encompasses embodiments of a method of reducing a bronchopulmonary disease of a patient, the method comprising the step of administering to the patient in need thereof a pharmaceutical composition comprising a bacterial population comprising at least one *Lactobacillus* species.

In some embodiments of this aspect of the disclosure, the bacterial population may comprise at least one *Lactobacillus* species selected from the group consisting of *Lactobacillus plantarum, Lactobacillus paracasei, Lactobacillus acidophilus* and *Lactobacillus rhamnosus*.

In some embodiments of this aspect of the disclosure, the bacterial population can consist of *Lactobacillus plantarum, Lactobacillus acidophilus* and *Lactobacillus rhamnosus*.

In some embodiments of this aspect of the disclosure, the bacterial population can consist of the strains *Lactobacillus rhamnosus* ATCC 53103, *Lactobacillus plantarum* wcfs 1 ATCC BAA-793, and *Lactobacillus acidophilus* ATCC 4356.

In some embodiments of this aspect of the disclosure, the bronchopulmonary disease of a patient is bronchopulmonary dysplasia.

In some embodiments of this aspect of the disclosure, at least one of the *Lactobacillus* species is not capable of proliferating in the recipient patient.

In some embodiments of this aspect of the disclosure, at least one of the *Lactobacillus* species is heat-killed.

In some embodiments of this aspect of the disclosure, at least one of the *Lactobacillus* species is viable and capable of proliferating in the recipient patient.

In some embodiments of this aspect of the disclosure, the bacterial population can be suspended in a pharmaceutically acceptable carrier.

In some embodiments of this aspect of the disclosure, the pharmaceutical composition can be delivered to the patient by a nebulizer.

In some embodiments of this aspect of the disclosure, the pharmaceutical composition can further comprise at least one therapeutic agent, wherein said agent or agents can reduce at least one symptom or pathological effect of a bronchopulmonary disease.

In some embodiments of this aspect of the disclosure, the therapeutic agent can be selected from the group consisting of: an anti-inflammatory agent or an anti-oxidant.

Still another aspect of the disclosure encompasses embodiments of a device for delivery of a pharmaceutical composition to the respiratory tract of a patient in need thereof, wherein the device comprises a nebulizer containing a pharmaceutical composition comprising a bacterial population comprising at least one *Lactobacillus* species.

In some embodiments of this aspect of the disclosure, the bacterial population may comprise at least one *Lactobacillus* species selected from the group consisting of *Lactobacillus plantarum*, *Lactobacillus paracasei*, *Lactobacillus acidophilus* and

*Lactobacillus rhamnosus*.

In some embodiments of this aspect of the disclosure, the bacterial population can consist of *Lactobacillus plantarum*, *Lactobacillus acidophilus* and *Lactobacillus rhamnosus*.

In some embodiments of this aspect of the disclosure, the bacterial population can consist of the strains *Lactobacillus rhamnosus* ATCC 53103, *Lactobacillus plantarum* wcfs 1 ATCC BAA-793, and *Lactobacillus acidophilus* ATCC 4356.

In some embodiments of this aspect of the disclosure, at least one of the *Lactobacillus* species is not capable of proliferating in the recipient patient.

In some embodiments of this aspect of the disclosure, at least one of the *Lactobacillus* species is viable and capable of proliferating in the recipient patient.

In some embodiments of this aspect of the disclosure, the bacterial population is suspended in a pharmaceutically acceptable carrier.

In some embodiments of this aspect of the disclosure, the pharmaceutical composition can further comprise at least one therapeutic agent, wherein said agent or agents can reduce at least one symptom or pathological effect of a bronchopulmonary disease.

In some embodiments of this aspect of the disclosure, the therapeutic agent can be selected from the group consisting of: an anti-inflammatory agent or an anti-oxidant.

In some embodiments of this aspect of the disclosure, the pharmaceutical composition can be formulated for administration to the respiratory tract of a patient by nasal spray delivery.

Still another aspect of the disclosure encompasses embodiments of a kit comprising: at least one container and a pharmaceutical composition therein, said pharmaceutical composition comprising a bacterial population comprising at least one *Lactobacillus* species and instructions for delivery of an effective amount of the composition to a patient in need thereof.

In some embodiments of this aspect of the disclosure, the bacterial population may comprise at least one *Lactobacillus* species selected from the group consisting of *Lactobacillus plantarum*, *Lactobacillus paracasei*, *Lactobacillus acidophilus* and *Lactobacillus rhamnosus*.

In some embodiments of this aspect of the disclosure, the bacterial population can consist of *Lactobacillus plantarum*, *Lactobacillus acidophilus* and *Lactobacillus rhamnosus*.

In some embodiments of this aspect of the disclosure, the bacterial population can consist of the strains *Lactobacillus rhamnosus* ATCC 53103, *Lactobacillus plantarum* wcfs1 ATCC BAA-793, and *Lactobacillus acidophilus* ATCC 4356

In some embodiments of this aspect of the disclosure, the kit can further comprise a pharmaceutically acceptable carrier.

In some embodiments of this aspect of the disclosure, the bacterial population can be admixed with the pharmaceutically acceptable carrier.

In some embodiments of this aspect of the disclosure, the kit can further comprise at least one therapeutic agent, wherein said agent or agents can reduce at least one symptom or pathological effect of a bronchopulmonary disease.

In some embodiments of this aspect of the disclosure, the therapeutic agent can be selected from the group consisting of: an anti-inflammatory agent or an anti-oxidant.

In some embodiments of this aspect of the disclosure, the therapeutic agent can be admixed with the pharmaceutically acceptable carrier.

In some embodiments of this aspect of the disclosure, the kit can further comprise a nebulizer.

In some embodiments of this aspect of the disclosure, the container is a nebulizer.

It should be emphasized that the embodiments of the present disclosure, particularly any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following claims.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

Isolation of Microbial DNA and Creation of 16S V4 amplicon Library: Microbial genomic DNA was isolated using the Fecal DNA isolation kit from Zymo Research (catalog #D6010; Zymo Research Corporation, Irvine, CA). Once the sample DNA was prepared, PCR was used with unique bar coded primers to amplify the V4 region of the 16S rRNA gene to create an amplicon library from individual samples (Kozich et al. (2013) *Appl. Environ. Microbiol.* 79:5112-5120; Kumar et al. (2014) *Curr. Protoc. Hum. Genet.* 82:18.8.1-18.8.29). Entire PCR reactions were electrophoresed on a 1.0% agarose/Tris-borate-EDTA gel.

Example 2

DNA sequencing: The PCR products were sequenced using NextGen sequencing Illumina MiSeq platform (Kozich et al. (2013) *Appl. Environ. Microbiol.* 79:5112-5120). Paired 250 base pair end kits from Illumina for the V4 region were used in the microbiome analysis. The samples were first quantitated using Pico Green, adjusted to a concentration of 4 nM then used for sequencing on the Illumina MiSeq (Kumar et al. (2014) *Curr. Protoc. Hum. Genet.* 82:18.8.1-18.8.29). Fastq conversion of the raw data files was performed following demultiplexing. Quality control of the fastq files was performed then subject to quality assessment and filtering using the FASTX toolkit (FASTX). The remainder of the steps was performed with the Quantitative Insight into Microbial Ecology (QIIME) suite, version 1.7 (Kumar et al. (2014) *Curr. Protoc. Hum. Genet.* 82:18.8.1-18.8.29; Lozupone et al. (2006) *BMC Bioinformatics* 7:371).

Example 3

Bioinformatics and Statistical Analysis: The sequence data covered the 16S rRNA V4 region with a PCR product length of approximately 255 bases and 250 base paired-end reads. Since the overlap between fragments was approximately 245 bases, the information from both ends of the paired reads was merged to generate a single high quality read using the module "fastq_mergepairs" of USEARCH.

Read pairs with an overlap of less than 50 bases or with too many mismatches (>20) in the overlapping region were discarded. Chimeric sequences were also filtered using the "identify_chimeric_seqs.py" module of USEARCH[47]. Overall read quality was assessed before and after filtering using FASTQC (FASTQC). The QIIME data analysis package was used for subsequent 16S rRNA data analysis. Sequences were grouped into operational taxonomic units (OTUs) using the clustering program UCLUST at a similarity threshold of 0.97%.

The Ribosomal Database Program (RDP) classifier was used to make taxonomic assignments (to the species level) for all OTUs at confidence threshold of 60% (0.6). The RDP classifier was trained using the Greengenes (v13_8) 16S rRNA database. The resulting OTU table included all OTUs, their taxonomic identification, and abundance information. OTUs whose average abundance was less than 0.0005% were filtered out. OTUs were then grouped together to summarize taxon abundance at different hierarchical levels of classification (e.g. phylum, class, order, family, genus, and species). These taxonomy tables were also used to generate bar charts of taxon abundance. Multiple sequence alignment of OTUs was performed with PyNAST. Alpha diversity (within sample diversity) was calculated using a variety of diversity metrics including Shannon's, Chao1, and Simpson, as implemented in QIIME[41]. Beta diversity (between sample diversity) among different samples was measured using Unifrac analysis, t tests[42]. Principal coordinates analysis (PCoA) was performed by QIIME to visualize the dissimilarity matrix (beta-diversity) between all the samples, such that samples which are more similar are closer in space than samples that are more divergent. 3D PCoA plots were generated using EMPEROR (Vazquez-Baeza et al. (2013) *Gigascience* 2:16). A heat map with the top 50 most highly abundant taxa across all samples was generated using the "heatmap.2" function in R package.

Example 4

Endotoxin Assay: The endotoxin concentration in samples was measured using the Pierce Limulus Amebocyte Lysate (LAL) assay Chromogenic Endotoxin Quantitation Kit (Pierce: 88282) via a chromogenic signal generated in the presence of endotoxins. A standard curve was created using the *E. coli* endotoxin standard included with each kit to calculate endotoxin levels as low as 0.1 EU/mL, where one endotoxin unit/mL (EU/mL) equals approximately 0.1 ng endotoxin/mL of solution.

Example 5

Patient population Discovery Cohort (UAB): Inborn and outborn ELBW and FT infants who underwent endotracheal intubation and mechanical ventilation at birth (in the first 6 hours of life) were included. In addition, infants diagnosed with moderate or severe BPD at 36 weeks' PMA defined using the physiologic definition (Walsh et al. (2004) *Pediatrics* 114:1305-1311) were included. Samples from a total of 150 infants were collected but only 51 were utilized for analysis based on strict inclusion criteria (23 ELBW infants and 10 FT infants-samples obtained at birth or within 6 h of birth at the time of intubation; 18 infants with established BPD-samples obtained at 36 wks PMA at the time of ETT change; samples with only >1000 bacterial sequence reads were used).

All 10 full term infants enrolled were intubated at or within 6 h of birth due to either surgical indications (congenital heart disease, abdominal wall defect) or due to perinatal depression (with no signs of meconium aspiration syndrome). Sample size calculations could not be performed as no baseline data in this population was available, but statistical power was established using standard statistical methods as described later.

No specific exclusions were made. Chorioamnionitis was determined by placental histopathology and all mothers with chorioamnionitis were administered antibiotics prenatally.

Example 6

Validation Cohort (Philadelphia): Patient samples from Philadelphia were used as a validation cohort to confirm the data. Tracheal aspirate (TA) samples from inborn and outborn ELBW infants who underwent endotracheal intubation and mechanical ventilation at birth were included. These samples were collected as part of ongoing studies (Mody et al. (2012) *J. Matern. Fetal Neonatal Med.* 25:1483-1487; Aghai et al. (2012) *Am. J. Perinatol.* 29:567-572; Aghai et al. (2013) *Pediatr. Pulmonol.* 48:8-13).

Example 7

Sample collection: Tracheal aspirate (TA) specimens were obtained from patients at the time of intubation in the first hours of life and thereafter whenever tracheal suctioning was clinically indicated, per unit protocol. Samples were obtained after ensuring that the infant was adequately oxygenated. The protocol for TA collection involved instillation of 1 mL sterile isotonic saline into the infant's endotracheal tube, manual bagging through the endotracheal tube for three breaths, and suctioning of the fluid into a sterile mucus trap. Samples were stored frozen in −80° C. until further processing. A similar protocol was employed at both study sites.

Example 8

Isolation of microbial DNA, creation of 16S V4 amplicon library and DNA sequencing: Microbial genomic DNA was isolated and PCR was used with unique bar coded primers to amplify the V4 region of the 16S rRNA gene to create an amplicon library from individual samples (Kozich et al. (2013) *Appl. Environ. Microbiol.* 79:5112-5120; Kumar et al. (2014) *Curr. Protoc. Hum. Genet.* 82:18.8.1-18.8.29). The PCR products were sequenced using the NextGen sequencing Illumina MiSeq platform (Kozich et al. (2013) *Appl. Environ. Microbiol.* 79:5112-5120). The sequence data covered the 16S rRNA V4 region with a PCR product length of approximately 255 bases and 250 base paired-end reads. Sequences were grouped into operational taxonomic units (OTUs). Only samples with >1000 reads were included. Alpha diversity value (within sample diversity) was calculated using Shannon's indez Caporaso et al. (2010) *Nat. Methods.* 7:335-336). Difference in alpha diversity amongst samples was calculated using t-tests. Unifrac analysis was used to determine relationships between different samples (beta diversity) (Lozupone et al. (2006) *BMC Bioinformatics* 7:371). Differences in beta diversity among different groups were measured using permanova test. Principal coordinates analysis (PCoA) was used visualize the dissimilarity between all the samples. 3D PCoA plots were generated using EMPEROR (Vazquez-Baeza et al. (2013) *Gigascience* 2:16). All raw data files have been uploaded online on Sequence Read Archive (SRA-SUB1512169).

Example 9

Clinical data collection: Data collection was performed via electronic medical record review at time of enrollment and during remainder of hospitalization. Chorioamnionitis was determined by histopathology, BPD at 36 wks postmenstrual age was defined by the physiologic definition (Walsh et al. (2004) *Pediatrics* 114:1305-1311), and late sepsis was defined as a positive blood culture after 72 h of life.

Example 10

Demographics and characteristics of patients in the Discovery Cohort are as in Table 2.

TABLE 2

Demographic characteristics of ELBW, FT and BPD infants.

|  | Full term infants sampled on day 1 after birth (FT) | ELBW infants, sampled on day 1 after birth (ELBW) | Infants with established bronchopulmonary dysplasia (BPD) |
|---|---|---|---|
| Study population n | 10 | 23 | 18 |
| Postmenstrual age tracheal | 38.3 ± 2.2 | 24.5 ± 0.2 | 37.6 ± 1.5 |
| Gestational age, weeks ± SD | 38.2 ± 2.2 | 24.3 ± 1.5 | 25.3 ± 2.1 |
| Birth weight, grams ± SD | 3334 ± 521 | 645 ± 163 | 731 ± 287 |
| Male sex, no. (%) | 8 (80) | 8 (35) | 9 (50) |
| Race |  |  |  |
| Black, no. (%) | 5 (50) | 17 (74) | 12 (67) |
| White, no. (%) | 5 (50) | 6 (26) | 6 (33) |
| Antenatal corticosteroids, no. | 1 (10) | 22 (96) | 16 (89) |
| Chorioamnionitis, no. (%) | 2 (20) | 10 (43) | 9 (50) |
| Rupture of membranes >18 | 3 (30) | 4 (17) | 5 (28) |
| Cesarean section, no. (%) | 4 (40) | 15 (65) | 12 (67) |
| Pre-eclampsia, no. (%) | 1 (10) | 13 (57) | 5 (28) |
| Intrauterine growth | 0 (0) | 10 (43) | 6 (33) |
| Intubation in delivery room, | 3 (30) | 10 (43) | 12 (67) |
| Respiratory distress | 2 (20) | 22 (96) | 18 (100) |
| Treatment with surfactant, no. | 2 (20) | 21 (91) | 18 (100) |
| High frequency ventilation, | 1 (10) | 7 (26) | 7 (39) |
| Ventilator days, mean ± SD | 6 ± 7 | 32 ± 38 | 77 ± 49 |
| CPAP days, mean ± SD | 1 ± 2 | 21 ± 19 | 54 ± 38 |
| Oxygen days, mean ± SD | 9 ± 11 | 92 ± 58 | 225 ± 92 |
| Died, no. (%) | 0 (0) | 1 (4) | 7 (39) |
| Bronchopulmonary dysplasia, | 0 (0) | 10 (43) | 18 (100) |
| Pulmonary hemorrhage, no. | 0 (0) | 5 (22) | 2 (11) |
| Symptomatic patent ductus | 0 (0) | 9 (39) | 9 (50) |
| Sepsis, no. (%) | 0 (0) | 8 (35) | 13 (72) |
| Intracranial hemorrhage≥ | 0 (0) | 2 (9) | 1 (6) |
| Retinopathy of prematurity≥ | 0 (0) | 2 (9) | 4 (22) |
| Necrotizing enterocolitis≥ | 0 (0) | 5 (22) | 4 (22) |

Based on their pulmonary outcomes, the 23 ELBW infants were further categorized as the ones who did not develop BPD (BPD Resistant, n=13) or the ones who later developed BPD (BPD Predisposed, n=10) at 36 wks postmenstrual age (PMA). The demographics and clinical characteristics of enrolled ELBW patients from UAB are shown in 5 Table 3.

TABLE 3

Discovery Cohort Demographics.

|  | Discovery Cohort | |
| --- | --- | --- |
|  | BPD-Resistant | BPD-Predisposed |
| Study population, n | 13 | 10 |
| Gestational age, weeks ± SD | 24.8 ± 1.7 | 23.5 ± 0.7 |
| Birth weight, grams ± SD * | 686 ± 140 | 564 ± 93 |
| Male sex, no. (%) | 4 (31) | 4 (40) |
| Race |  |  |
| Black, no. (%) | 10 (77) | 7 (70) |
| White, no. (%) | 3 (23) | 3 (30) |
| Antenatal corticosteroids, no. (%) | 12 (92) | 10 (100) |
| Chorioamnionitis, no. (%) | 6 (46) | 4 (40) |
| Rupture of membranes >18 hours, no. (%) | 3 (23) | 1 (10) |
| Cesarean section, no. (%) | 8 (62) | 7 (70) |
| Pre-eclampsia, no. (%) | 7 (54) | 6 (60) |
| Intrauterine growth restriction, no. (%) | 4 (31) | 6 (60) |
| Intubation in delivery room, no. (%) | 5 (38) | 5 (50) |
| Respiratory distress syndrome, no. (%) | 12 (92) | 10 (100) |
| Treatment with surfactant, no. (%) | 11 (85) | 10 (100) |
| High frequency ventilation, no. (%) | 2 (15) | 5 (50) |
| Ventilator days, mean ± SD * | 13 ± 18 | 58 ± 43 |
| CPAP days, mean ± SD | 14 ± 14 | 29 ± 23 |
| Oxygen days, mean ± SD * | 51 ± 39 | 145 ± 26 |
| Died, no. (%) | 0 (0) | 0 (0) |
| Pulmonary hemorrhage, no. (%) | 2 (15) | 3 (30) |
| Symptomatic patent ductus arteriosus, no. | 6 (46) | 3 (30) |
| Sepsis, no. (%) | 4 (31) | 4 (40) |
| Intracranial hemorrhage ≥ grade 3, no. | 2 (15) | 0 (0) |
| Retinopathy of prematurity ≥ stage 3, no. | 0 (0) | 2 (20) |
| Necrotizing enterocolitis ≥ stage 2, no. (%) | 1 (8) | 4 (40) |

The validation cohort was also categorized based on their pulmonary outcomes, into infants who did not go on to develop BPD (BPD Resistant, n=7) or the ones who later developed BPD (BPD Predisposed, n=7). The demographics and clinical characteristics of enrolled ELBW patients for the validation cohort are shown in Table 4.

TABLE 4

Validation Cohort-Demographics.

|  | Validation cohort | |
| --- | --- | --- |
|  | BPD-Resistant | BPD-Predisposed |
| Study population, n | 7 | 7 |
| Gestational age, weeks± | 25.1 ± 0.7 | 24.8 ± 1.7 |
| Birth weight, grams ± SD | 700 ± 340 | 686 ± 140 |
| Male sex, no. (%) | 5 (71) | 4 (57) |

To determine the temporal changes in airway microbiome serial tracheal aspirates (TA) were collected at various time points from birth until the development of BPD in 5 infants from the discovery cohort.

Example 11

Figure 1A:
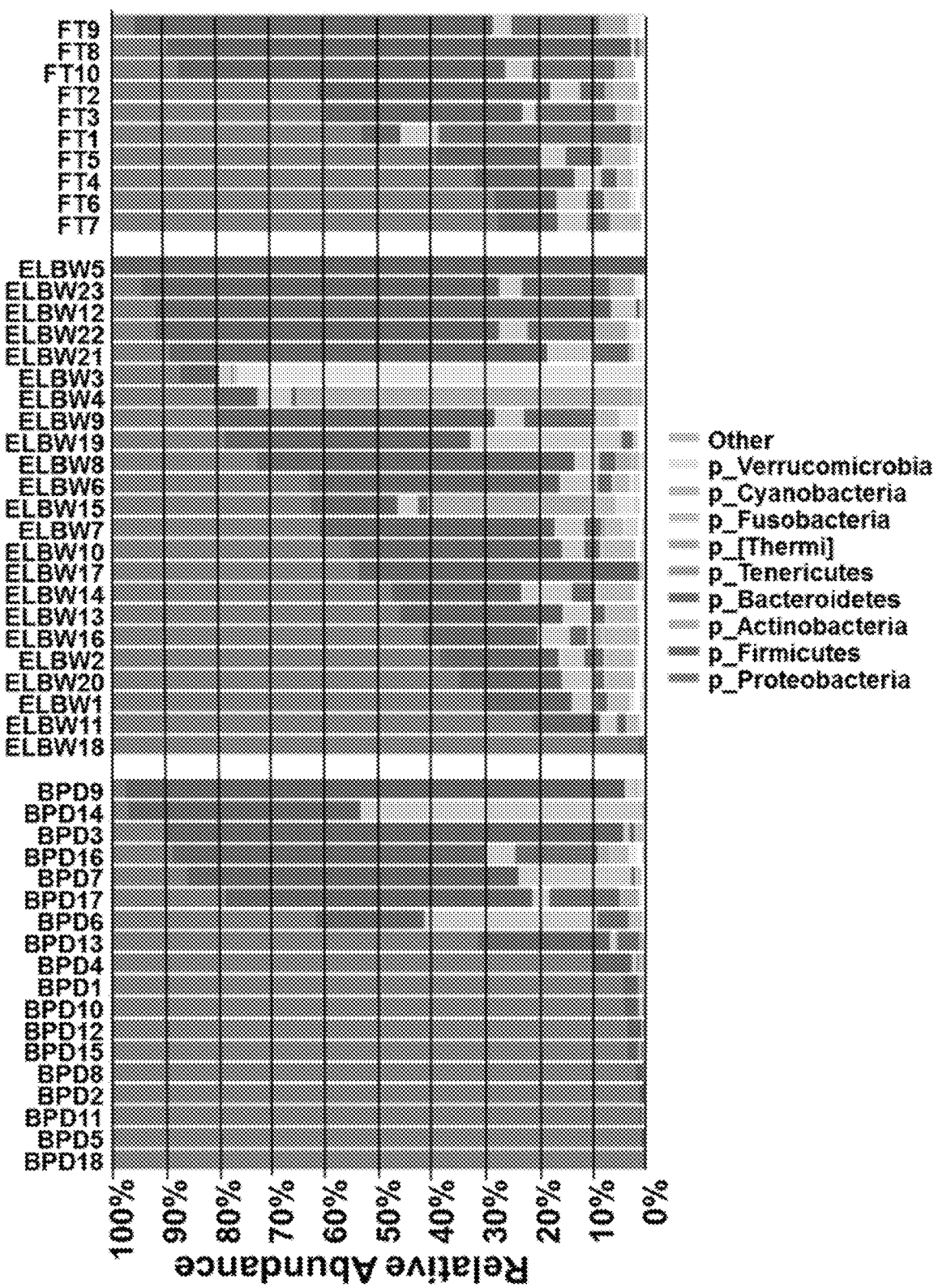
FIGS. 1A-1D. Comparison of lung microbiota of newborn infants and patients with BPD.
Figure 2:
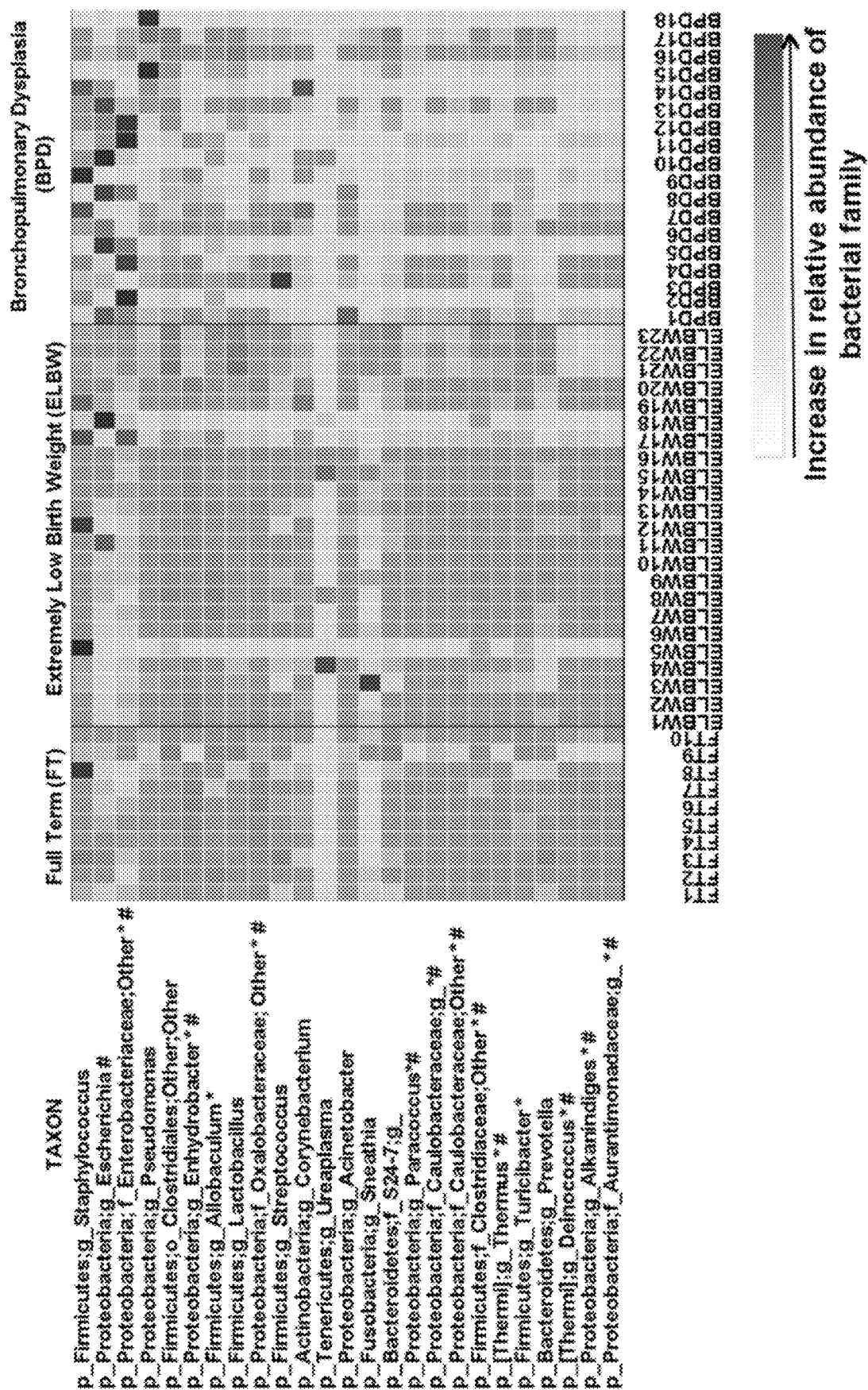
FIG. 2. Genus level lung microbial abundance of ELBW infants, FT infants and patients with BPD. Heat map depicting the relative abundance of the most common bacterial families at the genus level. Statistically significant difference in microbial abundance is seen between lung microbiome of ELBW and BPD infants (*) and between FT and BPD infants (#).

The airways of ELBW and FT infants have a distinct microbiota even at birth: It was possible to detect and characterize bacterial DNA in tracheal aspirates of all ELBW and FT infants soon after birth (FIGS. 1A and 2). All specimens resulted in amplification of the 16S rRNA used for microbiome analysis. Most mothers of premature infants received antimicrobial therapy before delivery (Table 5).

TABLE 5

Maternal antibiotic administration prior to birth in ELBW infants.

| Patient | Maternal Antibiotics (within 72 h prior to birth) | Type of Antibiotics |
| --- | --- | --- |
| BPD Predisposed | | |
| 1 | No | |
| 2 | Yes | ampicillin, amoxicillin, gentamicin |
| 3 | No | |
| 4 | No | |
| 5 | Yes | cefazolin |
| 6 | Yes | ampicillin |
| 7 | Yes | amphotericin B |
| 8 | Yes | acyclovir |
| 9 | Yes | ampicillin, gentamicin |
| 10 | Yes | cefazolin |
| BPD Resistant | | |
| 1 | Yes | ampicillin |
| 2 | Yes | amphotericin B, azithromycin, clindamycin, gentamicin |
| 3 | Yes | cefazolin |
| 4 | No | |
| 5 | Yes | ampicillin, amoxicillin, azithromycin |
| 6 | Yes | ampicillin |
| 7 | Yes | ampicillin, amoxicillin, azithromycin |
| 8 | Yes | ampicillin |
| 9 | Yes | ampicillin |
| 10 | Yes | ampicillin |
| 11 | Yes | ampicillin, cefepime, vancomycin, acyclovir |
| 12 | No | |
| 13 | Yes | acyclovir |

On statistical analysis, there were no differences in the airway microbiome of the infants of mothers who received prenatal antibiotics versus infants of mothers who did not.

Example 12

Figure 1B:
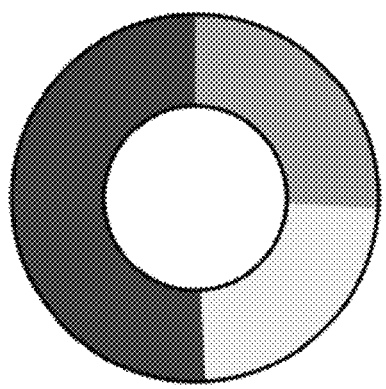
Figure 1B:
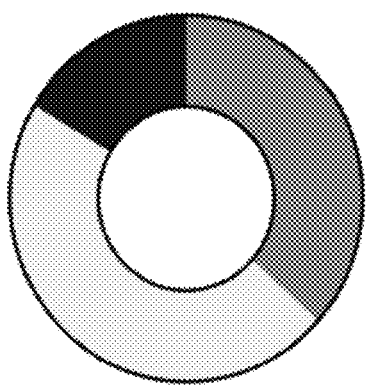
Figure 1C:
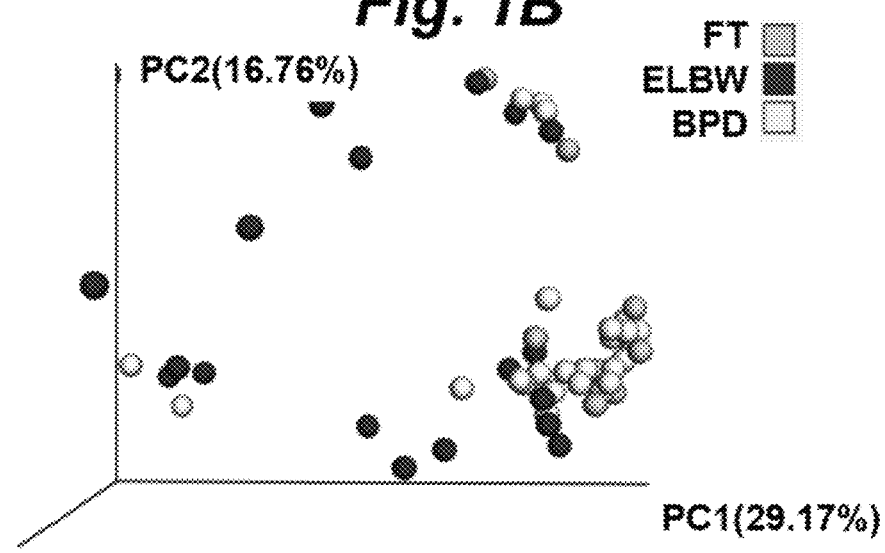

Airway microbiome of ELBW and FT infants is similar at birth: The taxonomic analysis has demonstrated that the lung microbiome was similar at birth in ELBW and FT infants irrespective of gestational age (FIGS. 1A and 1C). Both ELBW and FT infants had a predominance of Firmicutes and Proteobacteria on the first day of life, in addition to the presence of Actinobacteria, Bacteroidetes, Tenericutes, *Fusobacterium, Cyanobacteria*, and *Verrucomicrobia* (FIG. 1A).

The relative abundance of bacterial phyla did not differ between ELBW and FT infants. The diversity between the groups was compared and the Shannon diversity index for alpha diversity (which gives an estimate of richness, evenness, and microbial diversity within a sample) was calculated. There was no difference between the Shannon alpha diversity for ELBW and FT infants (p=0.46, t-test, FIG. 1D). As shown in the principal coordinate analysis (PCoA) plot (FIG. 1C), the BPD infant microbiomes clustered separately with a greater Unifrac distance separating them, whereas ELBW and FT microbiomes had significant overlap on the PCoA plot (p=0.19, permanova test, FIG. 1C). Tenericutes, including genus *Ureaplasma* were identified in the tracheal aspirates of both ELBW and FT infants (FIGS. 1A and 2), although the relative abundance was higher in ELBW infants.

Example 13

The microbial composition of the airway is different and less diverse in infants with BPD com-pared to FT and ELBW infants: Compared to newborn FT infants matched for post-menstrual age, the airway microbiome of infants after diagnosis of BPD was characterized by increased phylum Proteobacteria and decreased phyla Firmicutes and Fusobacteria (FIGS. 1A, and 1B). Gamma Proteobacteria were more abundant in BPD infants whereas Alpha Proteobacteria were in lower abundance in BPD infants compared to newborn ELBW and FT infants (FIG. 2). At the genus level, the most abundant Proteobacteria in BPD patients were Enterobacteriaceae (FIG. 2).

Figure 1D:
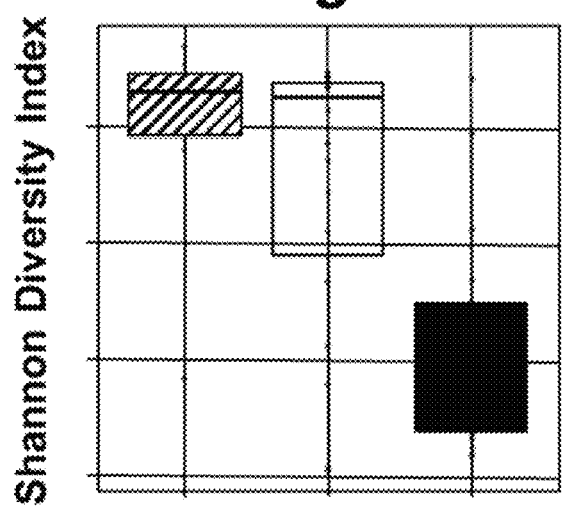

Differences in microbial composition between BPD and FT infants were confirmed by a difference in Shannon alpha diversity (p<0.002; t-test; FIG. 1D). Unifrac-weighted distances for beta diversity were used (that are inclusive of abundance, the presence or absence of OTUs between samples, and demonstrates how different microbes are distributed among samples). Different clustering as depicted in PCoA plots of Unifrac distances (p<0.0001; permanova test; FIG. 1C) was found. Differences in microbe diversity and abundance (alpha diversity p<0.003, t-test, FIG. 1D; beta diversity p<0.009, permanova test, FIG. 1C) were seen also between ELBW infants and infants with BPD (FIGS. 1 and 2). To confirm the presence of Proteobacteria in the BPD patient samples, specific endotoxin assays were also performed.

Example 14

Figure 3:
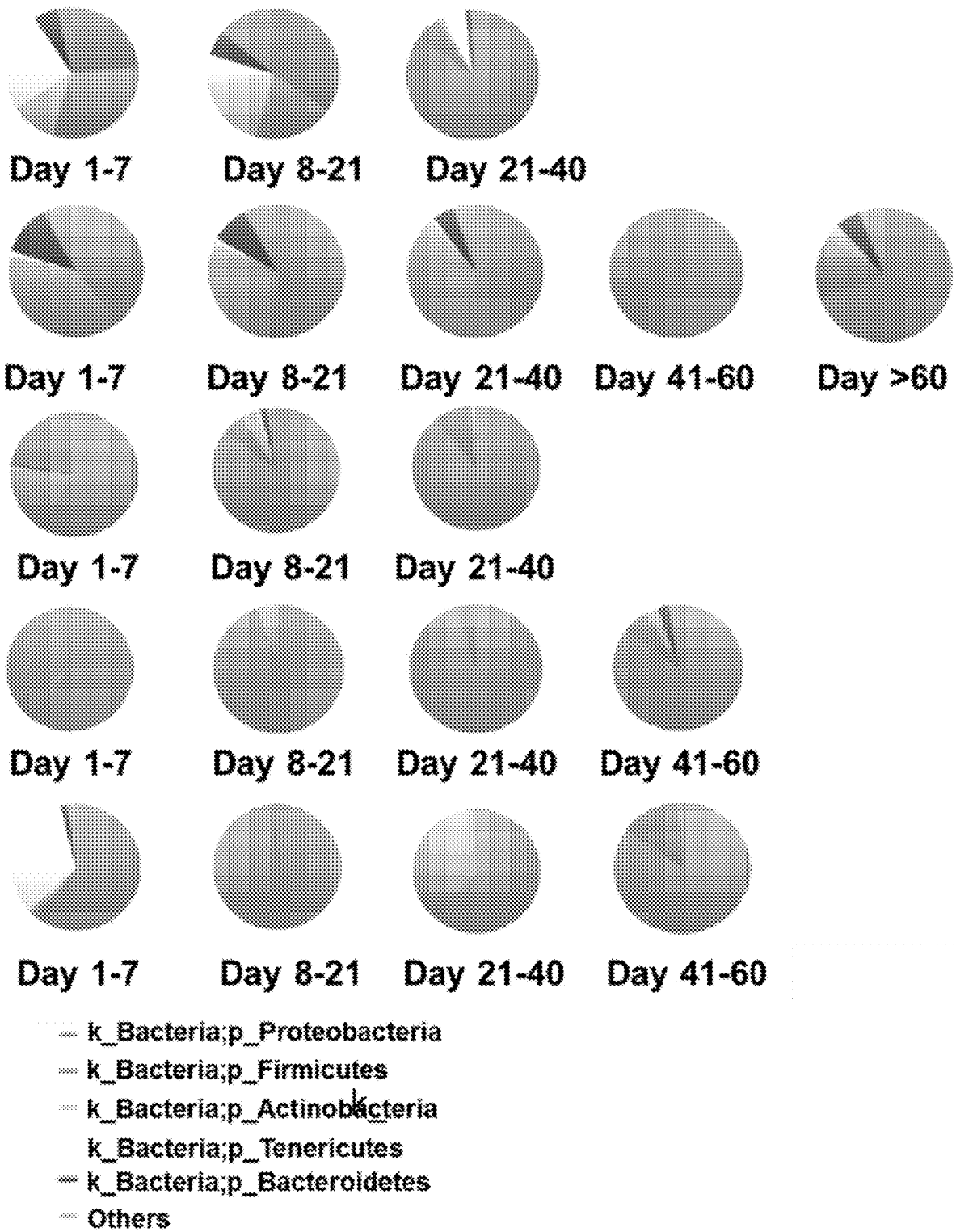
FIG. 3. Temporal changes in airway microbiome of ELBW infants who develop BPD. Pie charts showing the changes in airway microbiome with time in 5 ELBW patients (A-E) from birth onwards. In all patients, a relative increase in abundance of Proteobacteria and a relative decrease in abundances of Firmicutes, Actinobacteria, Tenericutes, Bacteroidetes and other microbes, are seen with time.

Airway microbiome of ELBW infants who go on to develop BPD show a consistent temporal dysbiosis: Five extremely premature infants were followed from birth until the development of BPD and serial TA collected at various postnatal time points (Day 1-7, Day 8-21, Day 21-40, Day 41-60, Day>60) (FIG. 3).

The first sample (labeled day 1-7) was collected on day 1 in 4 of the 5 patients (Patient A, B, C, D), whereas in the fifth patient the first sample was collected on day 5. The demographics of these infants are given in Table 5.

TABLE 5

Demographic characteristics of 5 ELBW infants who later develop BPD.

| Patient | A | B | C | D | E |
|---|---|---|---|---|---|
| Gestational age, | 23 | 23 | 23 | 22 | 24 |
| Birth weight, grams | 510 | 660 | 640 | 460 | 520 |
| Sex | Female | Male | Male | Female | Female |
| Race | Caucasian | African American | Caucasian | Caucasian | African American |
| Antenatal | Y | Y | Y | N | Y |
| Chorioamnionitis | N | Y | Y | Y | Y |
| Rupture of | N | Y | N | N | Y |
| Pre-eclampsia | N | N | N | N | N |
| Intrauterine growth | Y | N | N | N | N |
| Apgar - 1 minute | 5 | 3 | 2 | — | 1 |
| Apgar - 5 minutes | 8 | 8 | 2 | — | 3 |
| Intubation in | Y | N | Y | Y | Y |
| Respiratory | Y | Y | Y | Y | Y |
| Treatment with | Y | Y | Y | Y | Y |
| High frequency | N | N | N | Y | Y |

TABLE 5-continued

Demographic characteristics of 5 ELBW infants who later develop BPD.

| Patient | A | B | C | D | E |
|---|---|---|---|---|---|
| Pulmonary | N | N | N | N | Y |
| Symptomatic | Y | N | Y | N | N |
| Sepsis | Y | Y | N | N | N |
| Intracranial | N | N | N | Y | N |
| Retinopathy of | Y | N | N | N | N |
| Necrotizing | Y | N | N | N | N |

All 5 infants, despite having multiple courses of antibiotics at various different time points, had a distinct temporal dysbiotic change with a decrease in Firmicutes and increase in the abundance of Proteobacteria over time (FIG. 3).

Example 15

ELBW infants born by cesarean section (CS) and vaginal delivery have airway microbiota that do not differ at birth: Of the 23 ELBW infants in the discovery cohort, 15 (65%) were born by CS and 8 (35%) by vaginal delivery. There were no statistical differences between the airway microbiota of ELBW infants born by CS compared to the ones born by vaginal delivery (all microbial taxa: p>0.1, t-test).

Example 16

Genus *Lactobacillus* was decreased in airway microbiota of ELBW infants with chorioamnionitis: Among the discovery cohort of 23 ELBW infants, 10 (43%) had histological chorioamnionitis. The microbiome of infants with versus without histological chorioamnionitis differed at the genus level but not at the phylum level. A decreased abundance of genus *Lactobacillus* was seen in infants exposed to chorioamnionitis as compared to infants not exposed to chorioamnionitis (p=0.037, t-test, FIG. 3D). Among the validation cohort of 14 infants, only 2 had chorioamnionitis and hence this analysis was not possible (Table 3).

Example 17

Genus *Lactobacillus* is less abundant in the early airway microbiome of infants who later develop BPD: ELBW infants from both the discovery cohort and the validation cohort were subdivided into two groups based on their pulmonary outcomes into either BPD Resistant or BPD Predisposed.

Figure 4A:
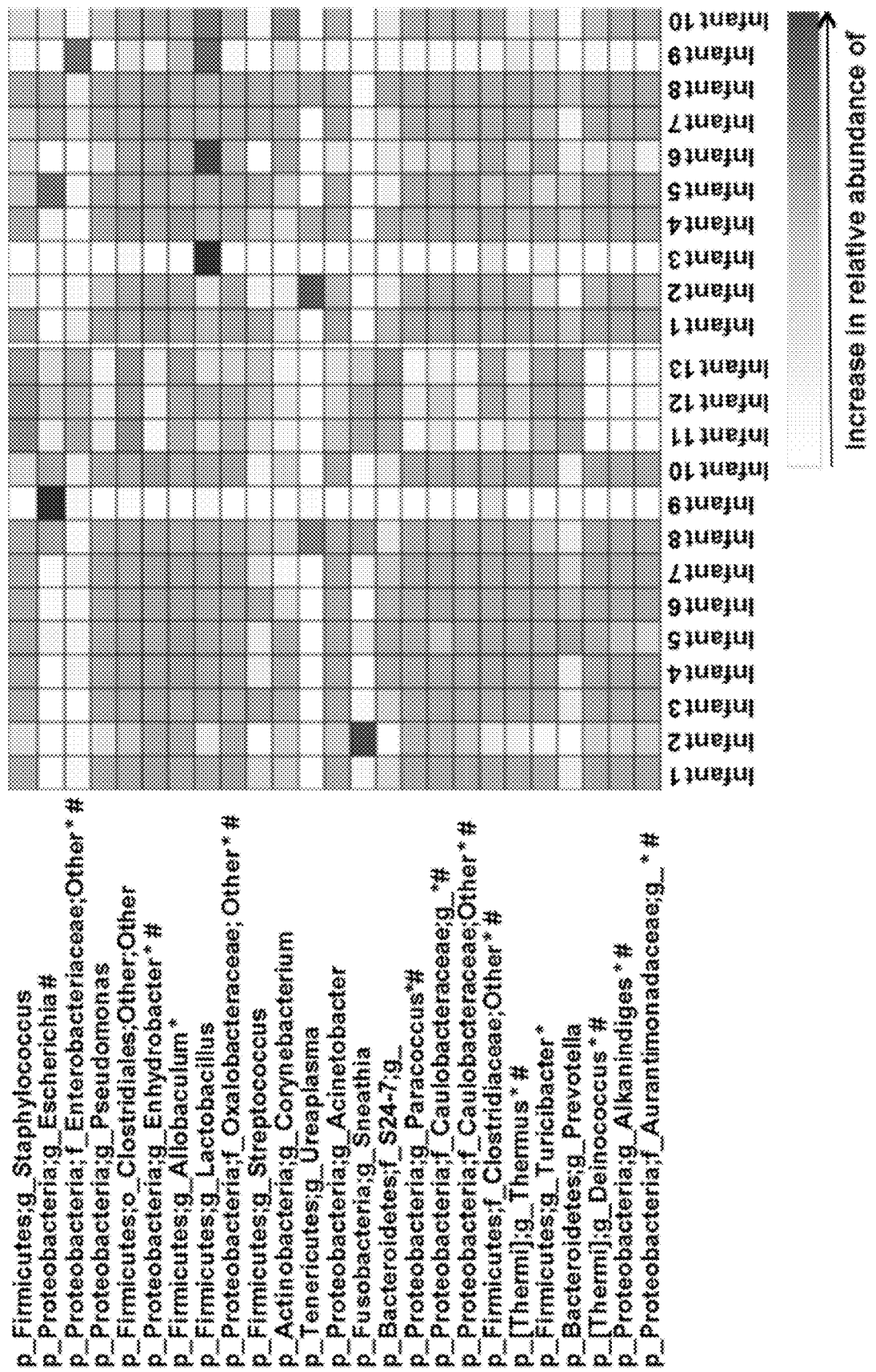
FIGS. 4A-4D. Early airway microbiome of ELBW infants and its association with development of BPD-Discovery Cohort.
Figure 4B:
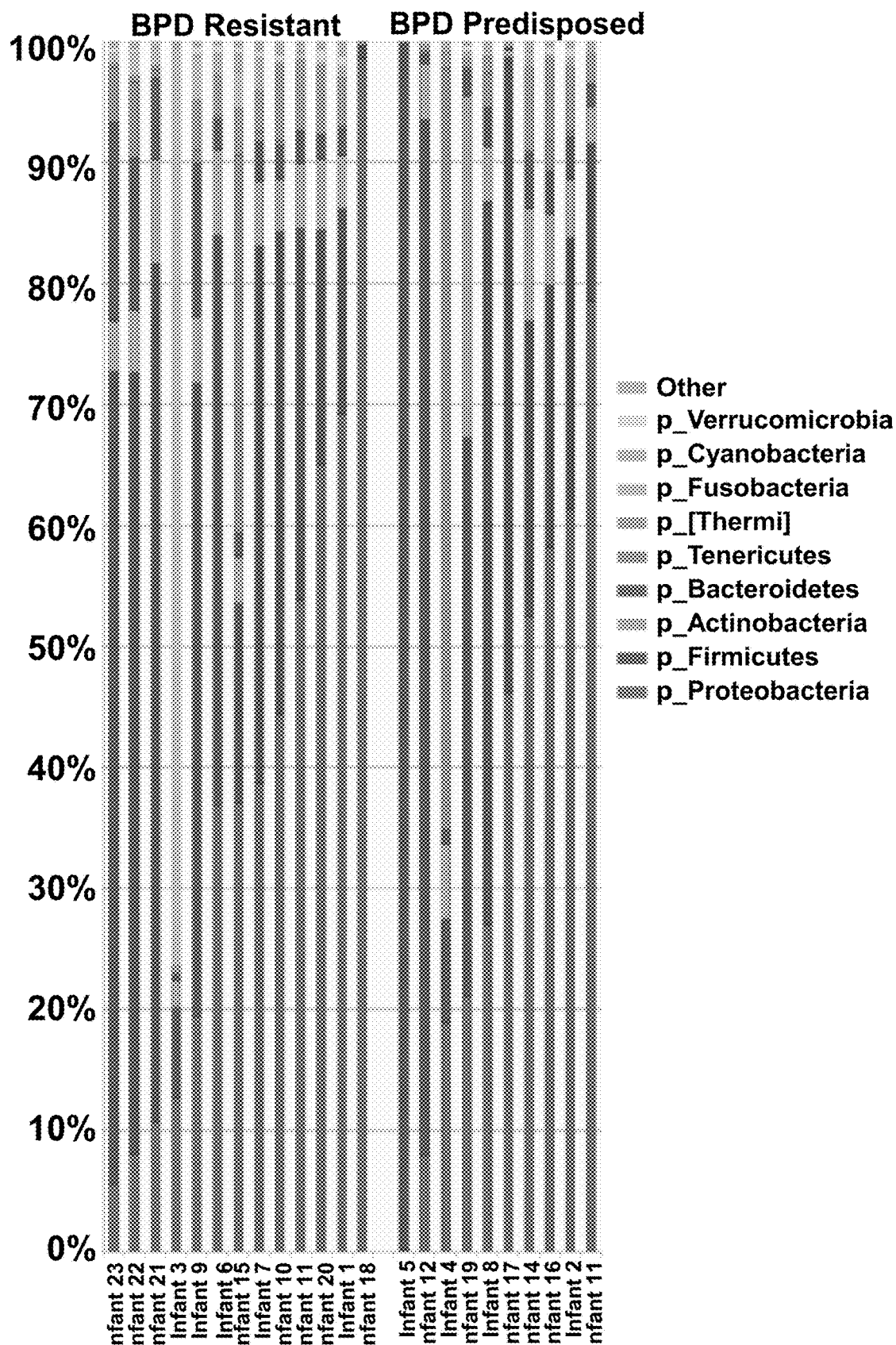
Figure 4C:
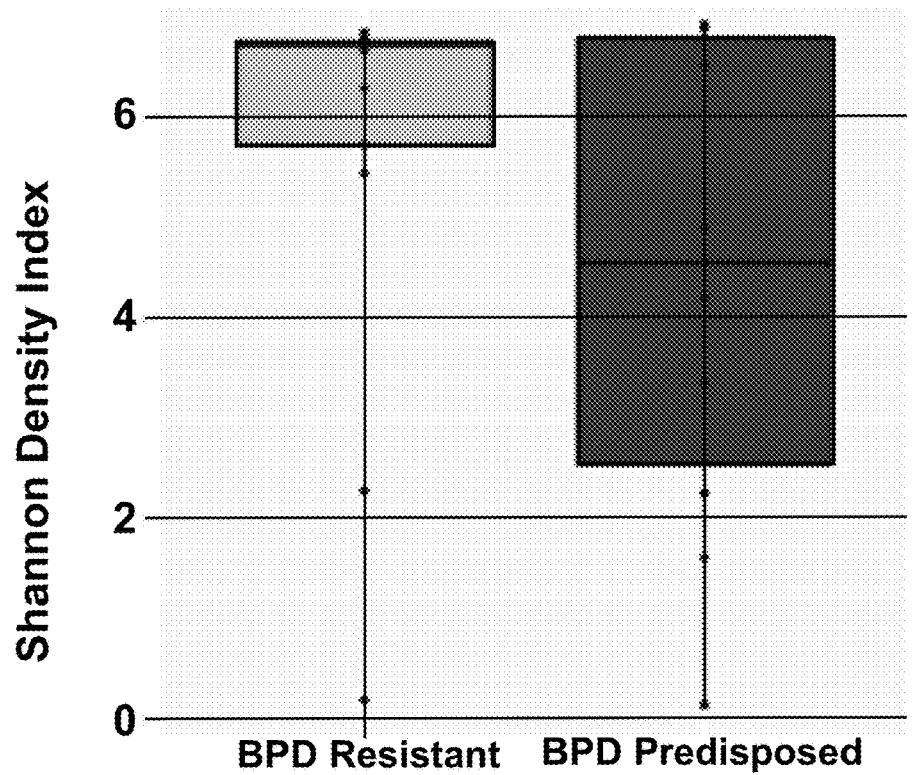
Figure 4D:
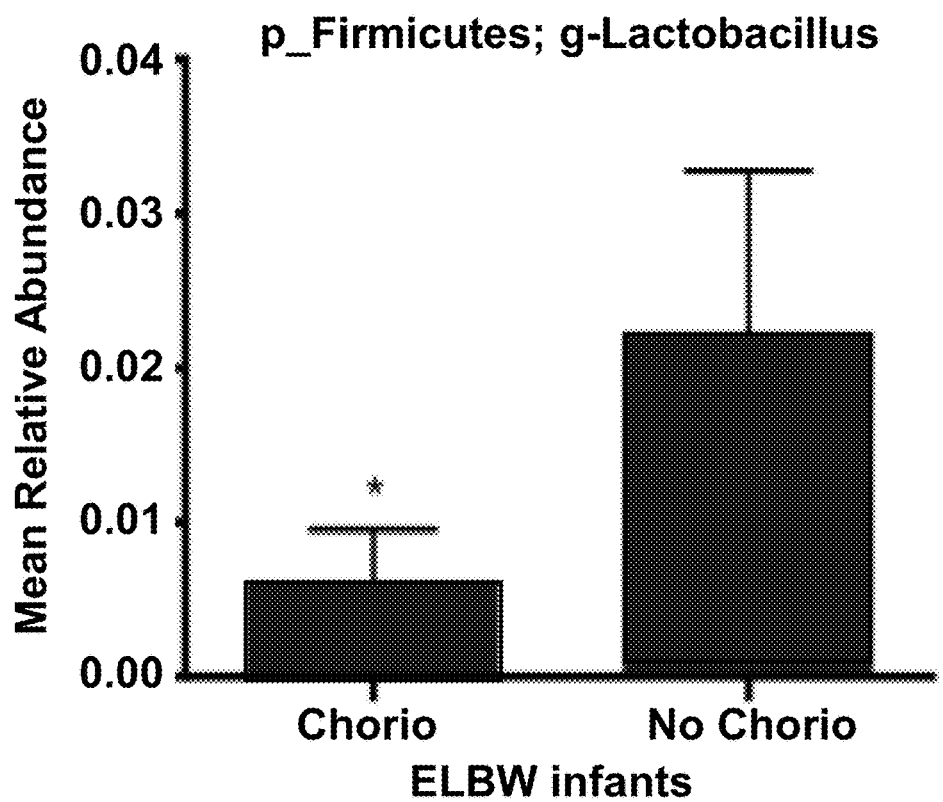

Discovery Cohort: All 23 ELBW infants survived to 36 wks PMA and were similar in demographic characteristics (Table 2). 10 of these 23 infants went on to develop BPD (BPD Predisposed) (FIG. 4). 13 of the 23 ELBW did not develop BPD and were deemed resistant to the disease (BPD Resistant) (FIG. 4). The relative phylum level microbial abundance (FIGS. 4A and 4B) and alpha diversity (p=0.18, FIG. 4C) were not statistically different between the BPD Resistant and BPD Predisposed groups. However at the genus level, genus *Lactobacillus* was less abundant in BPD-predisposed infants at birth, compared to the BPD Resistant infants (p<0.05, t-test; FIG. 4A).

Figure 5A:
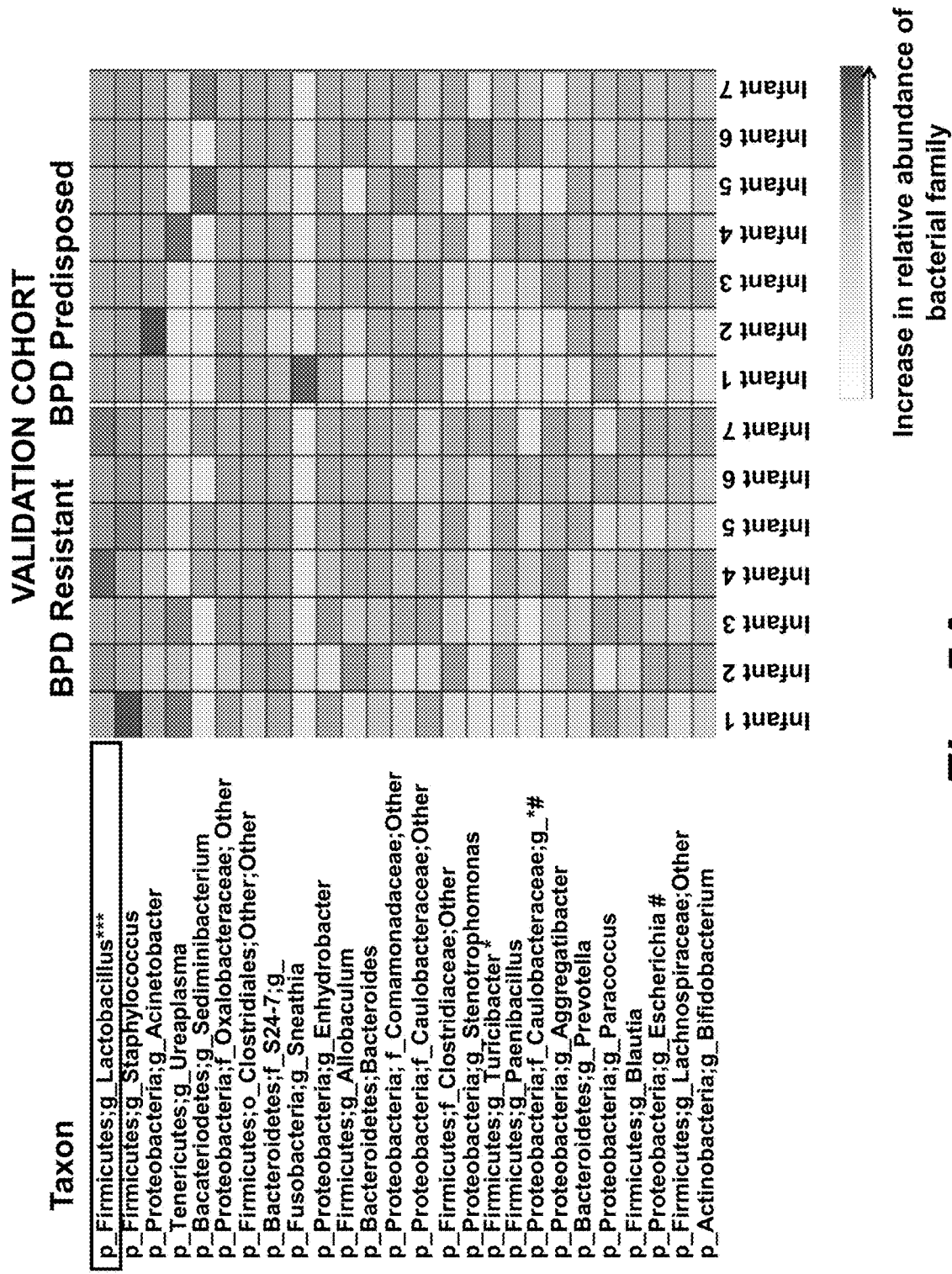
FIGS. 5A-5C. Early airway microbiome of ELBW infants and its association with development of BPD-Validation Cohort.
Figure 5B:
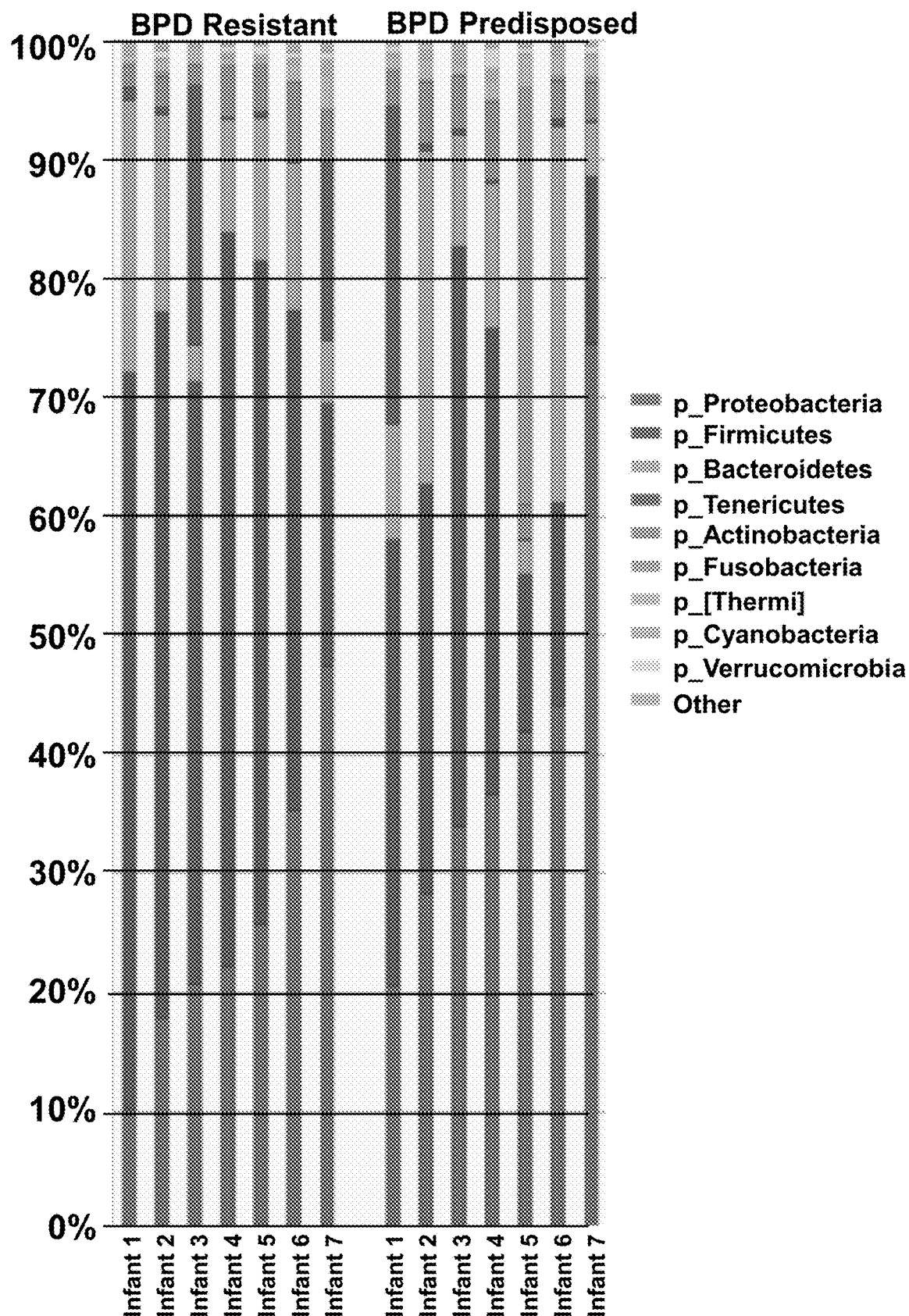
Figure 5C:
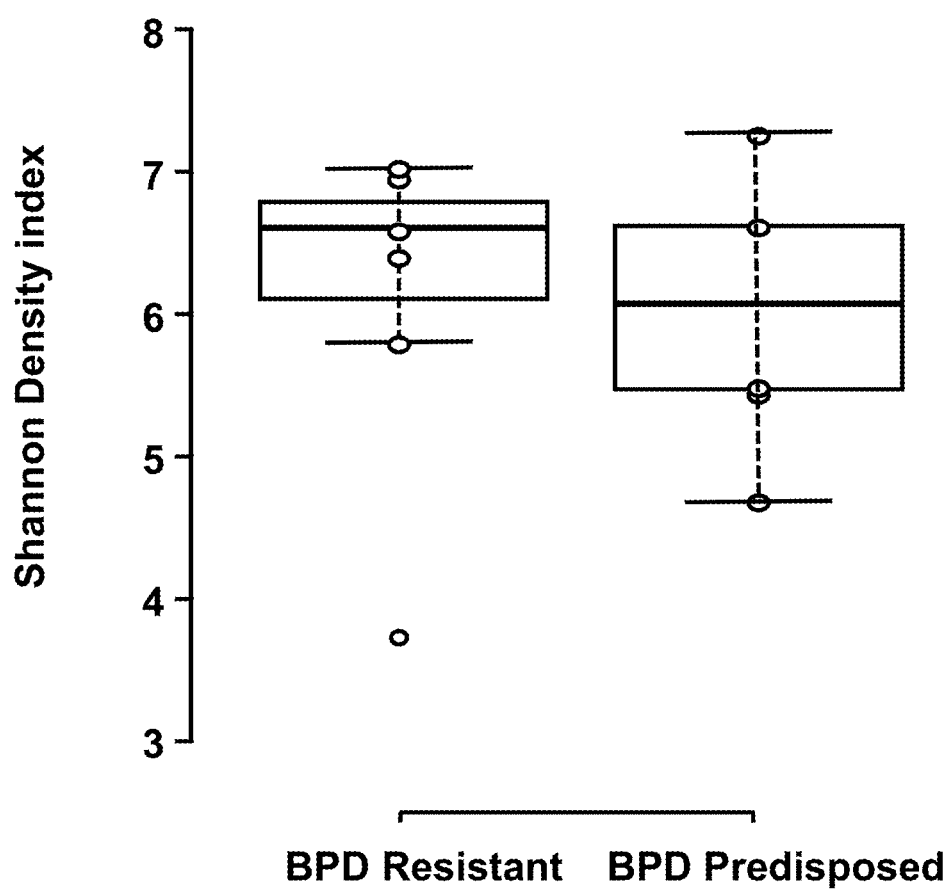
Figure 6:
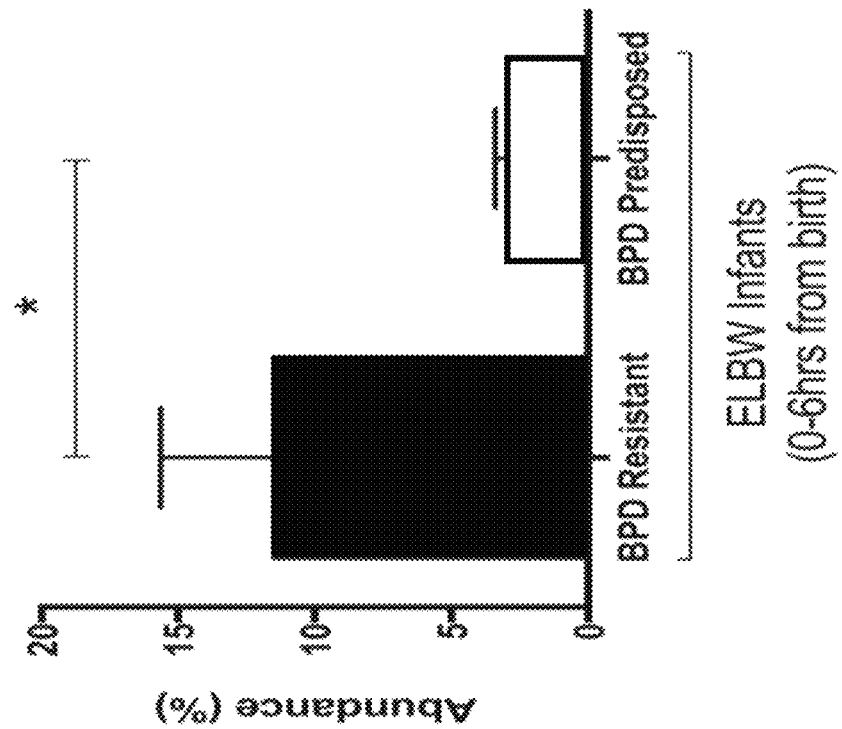
FIG. 6. Early airway Lactobacillus abundance in discovery and validation cohorts. Bar graphs depicting the relative abundance of Lactobacillus in ELBW infants at birth. In both the discovery cohort and the validation cohort the relative abundance of Lactobacillus is significantly higher in the BPD Resistant infants compared to BPD Predisposed infants (p<0.05).
Figure 6:
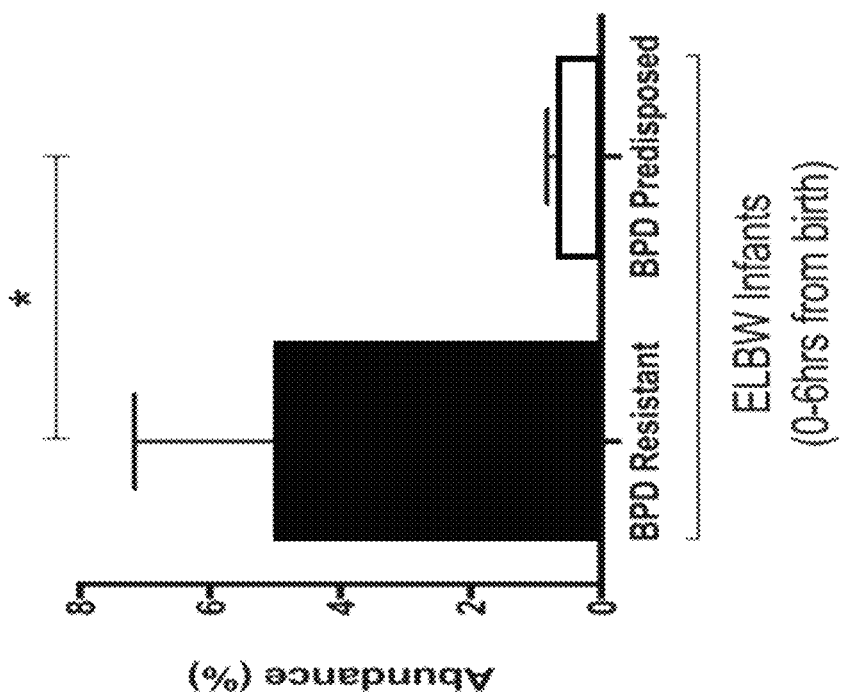

Validation Cohort: ELBW infants from the validation cohort were similarly subdivided into two groups based on their pulmonary outcomes-BPD Resistant (7 infants) and BPD Predisposed (7 infants). Both groups were similar in demographic characteristics (Table 3). Consistent with the findings of the discovery cohort, *Lactobacillus* was less abundant at the genus level in BPD Predisposed infants at birth compared to the BPD Resistant (p<0.04, t-test; FIG. 5A). The relative phylum level microbial abundance (FIGS. 5A and 5B) and diversity (p>0.1, FIG. 5C) were not statistically different between the BPD Resistant or BPD Predisposed groups.

Example 18

Figure 7:
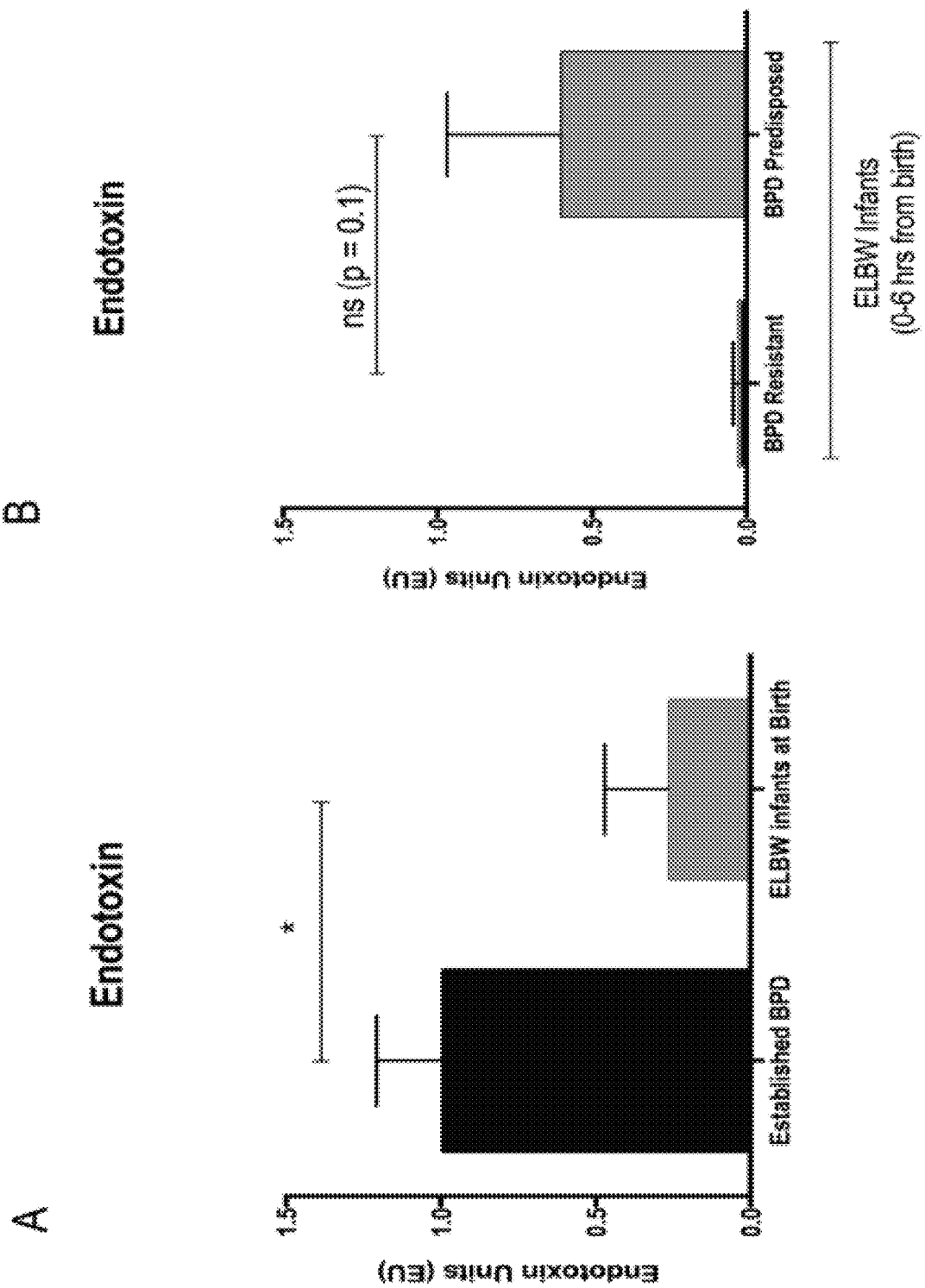
FIG. 7. Limulus amebocyte lysate chromogenic endotoxin levels in tracheal aspirates of infant. (A) Endotoxin concentrations are increased in tracheal aspirate samples collected from infants with BPD compared to infants at birth (p<0.05). (B) No difference was seen in endotoxin amounts in airways of BPD Resistant and BPD Predisposed ELBW infants at birth (p=0.1).
Figure 8:
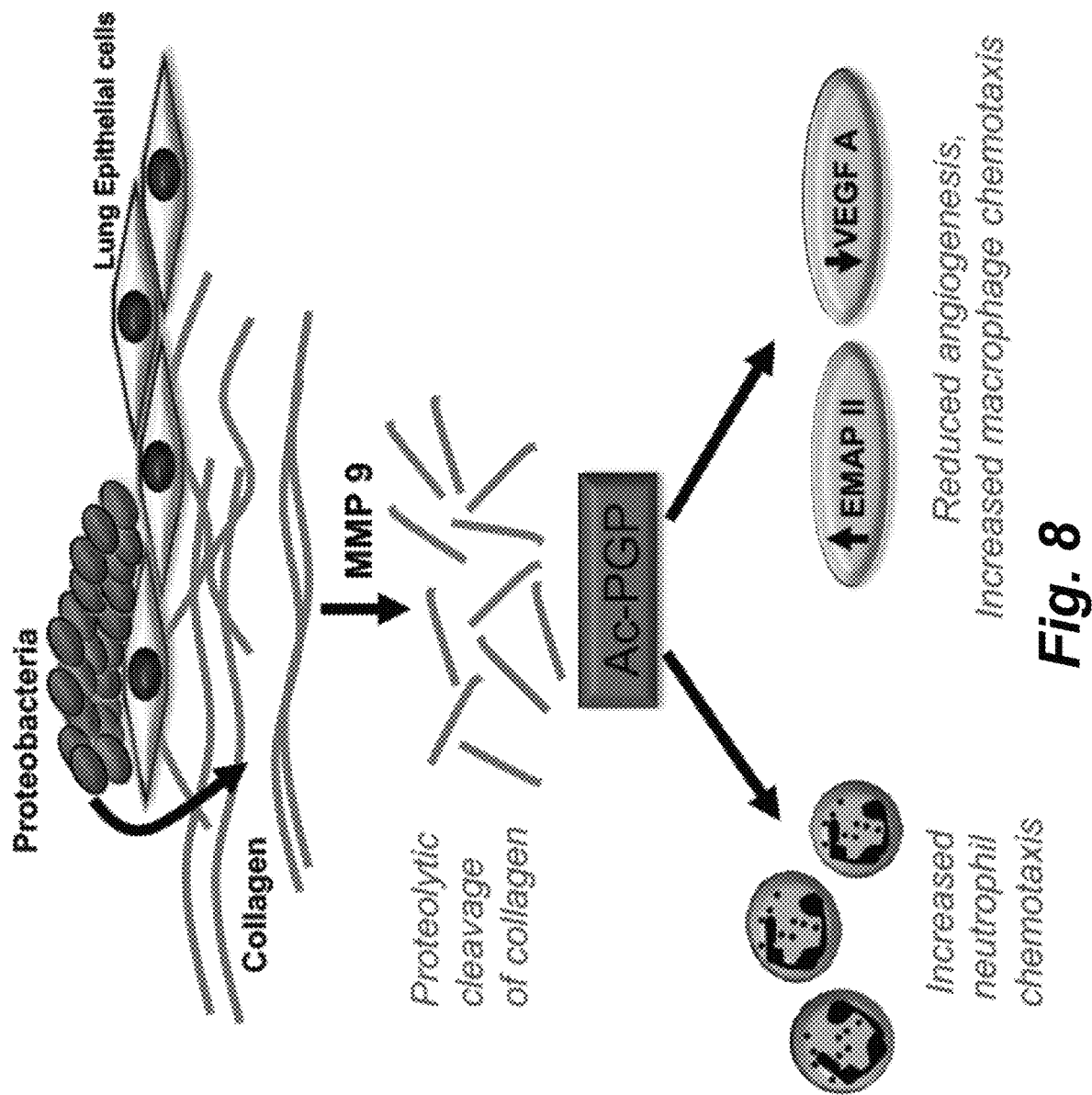
FIG. 8 schematically illustrates the generation of N-acetyl-Proline-Glycine-Proline (Ac-PGP) by Proteobacteria in the lungs of human subjects having reduced Lactobacillus populations.
Figure 9:
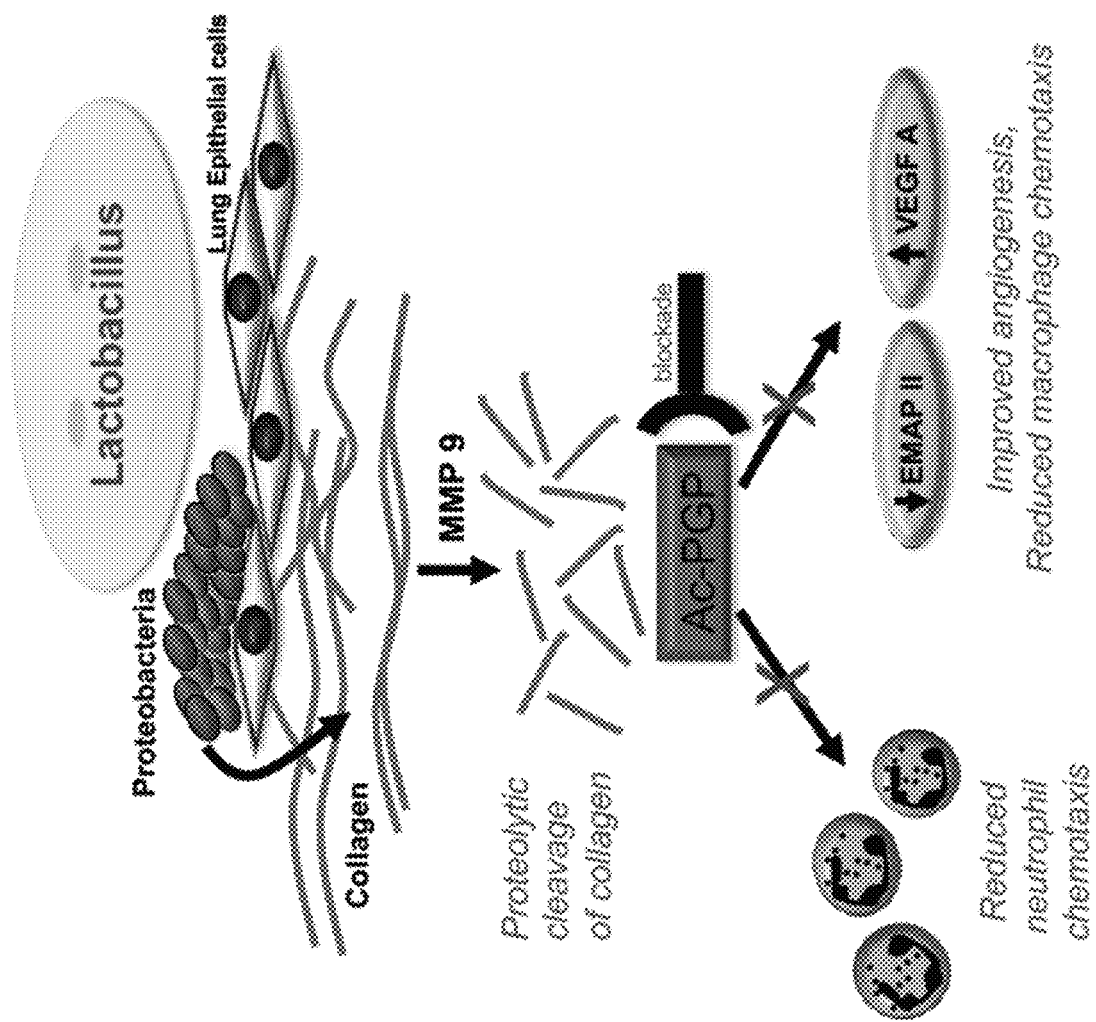
FIG. 9 schematically illustrates blockage of the generation of N-acetyl-Proline-Glycine-Proline (Ac-PGP) by Proteobacteria in the lungs of human subjects having elevated Lactobacillus populations.
Figure 10:
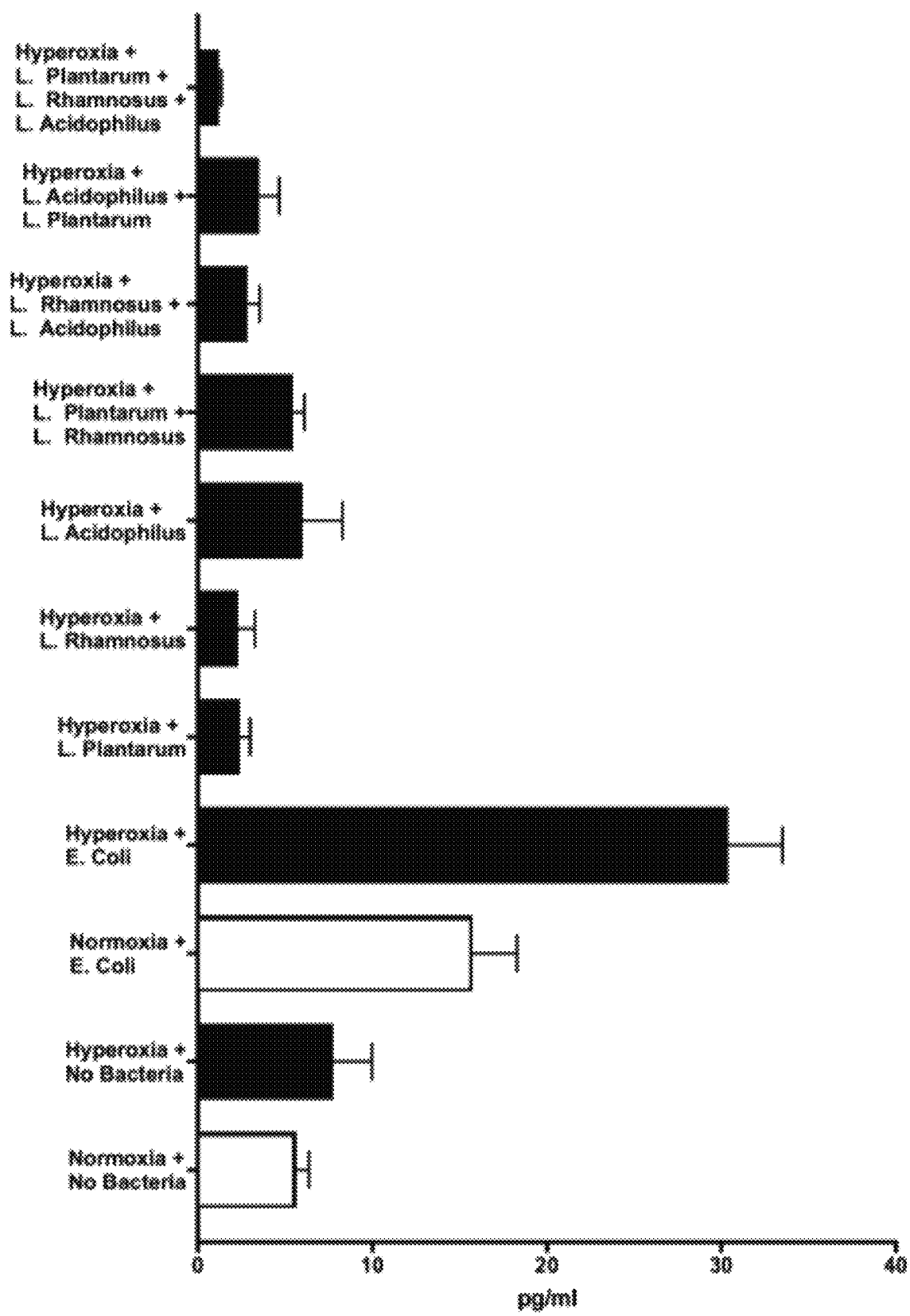
FIG. 10: To delineate the most anti-inflammatory combination of different Lactobacillus strains, in vitro experiments where normal human bronchial epithelial cells were inoculated with different strains of Lactobacillus (obtained from ATCC). Cytokine analysis were performed for various pro inflammatory cytokines including IL1β, TNF alpha, Interferon γ, MIP 1α, etc. were performed using custom made Milliplex Multiplex Assay kits. As Proteobacteria, (E. coli) increased cytokines production, most Lactobacillus decreased inflammatory cytokine production. The strongest anti-inflammatory effect was seen with combination of L. plantarum, L. acidophilus and L. rhamnosus. Shown is a representative cytokine (Interleukin 1β).
Figure 11:
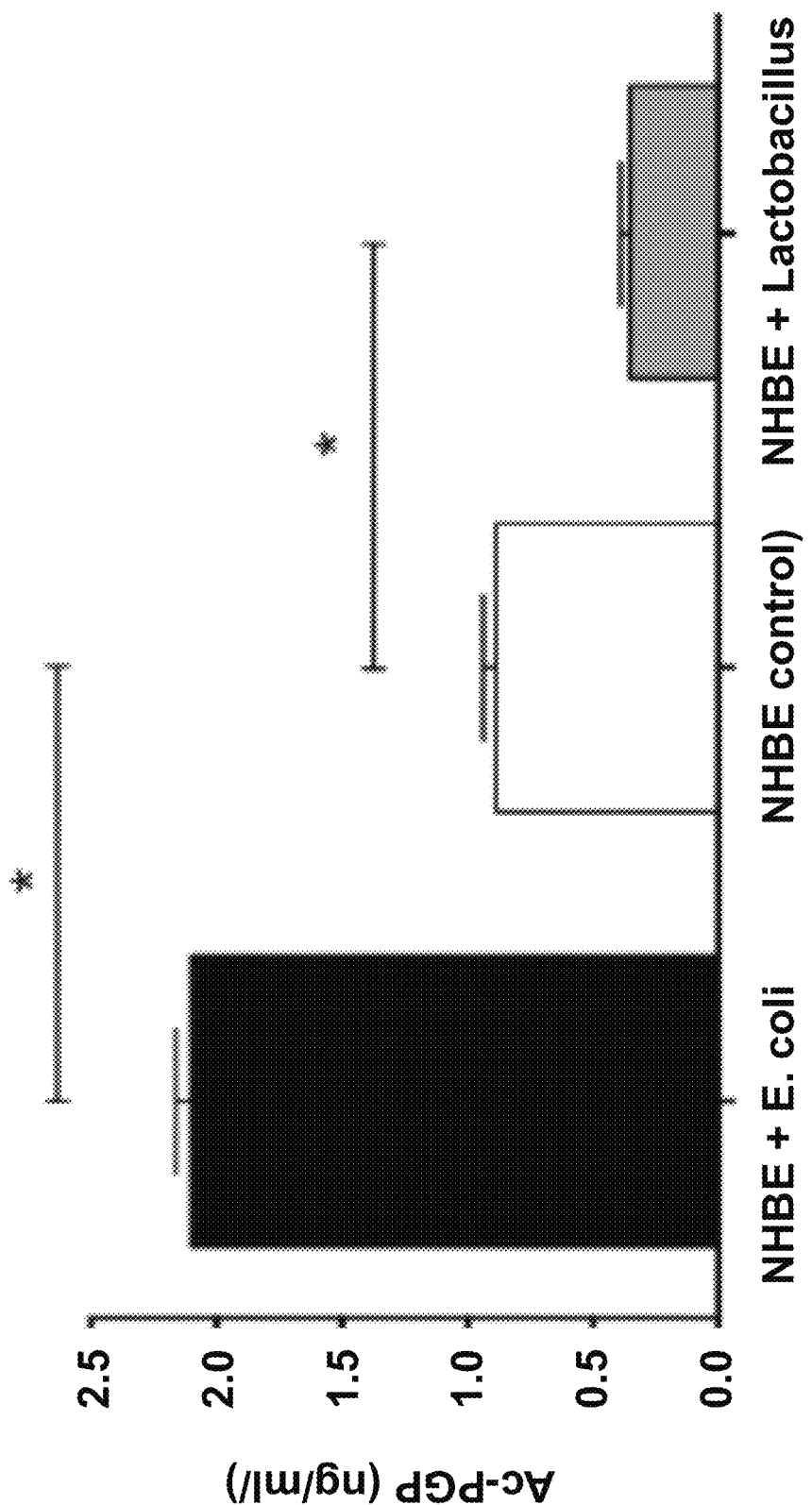
FIG. 11 is a graph illustrating the depression of Ac-PGP formation by Human Bronchial Epithelial Cells (NHBE) in tissue culture by Lactobacillus and elevation by a non-Lactobacillus species (E. coli). The Lactobacillus combination versus E. coli (pathogen in Bronchopulmonary Dysplasia) was administered to normal bronchial epithelial cells for 12 h and levels of potent neutrophilic chemotactic agent Ac-PGP were checked. The Lactobacillus combination decreased Ac-PGP levels, even below normal levels.
Figure 12:
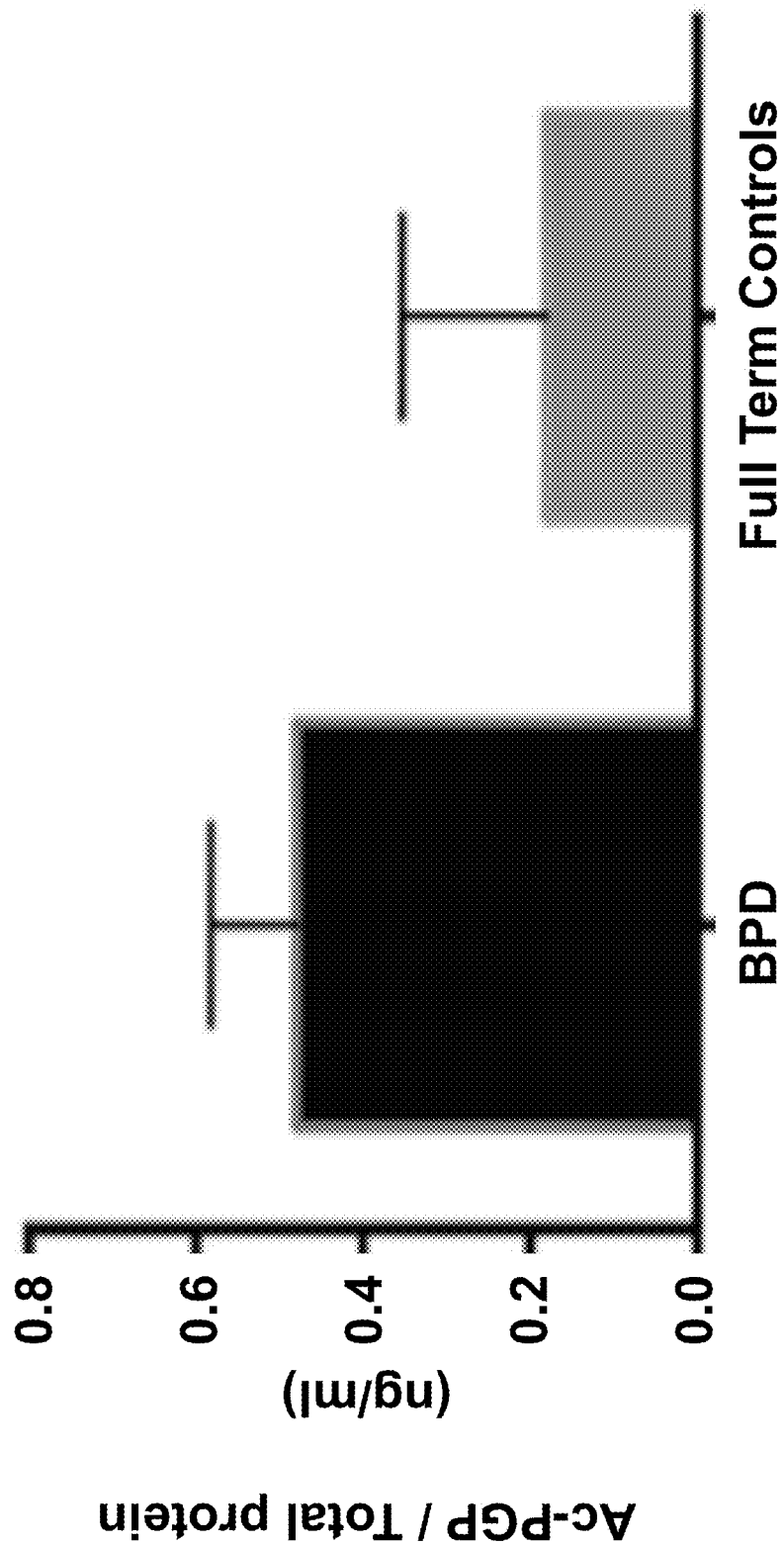
FIG. 12 is a graph illustrating the elevation of Ac-PGP in tracheal aspirates from pre-term infants compared with aspirates from full-term infants.
Figure 13:
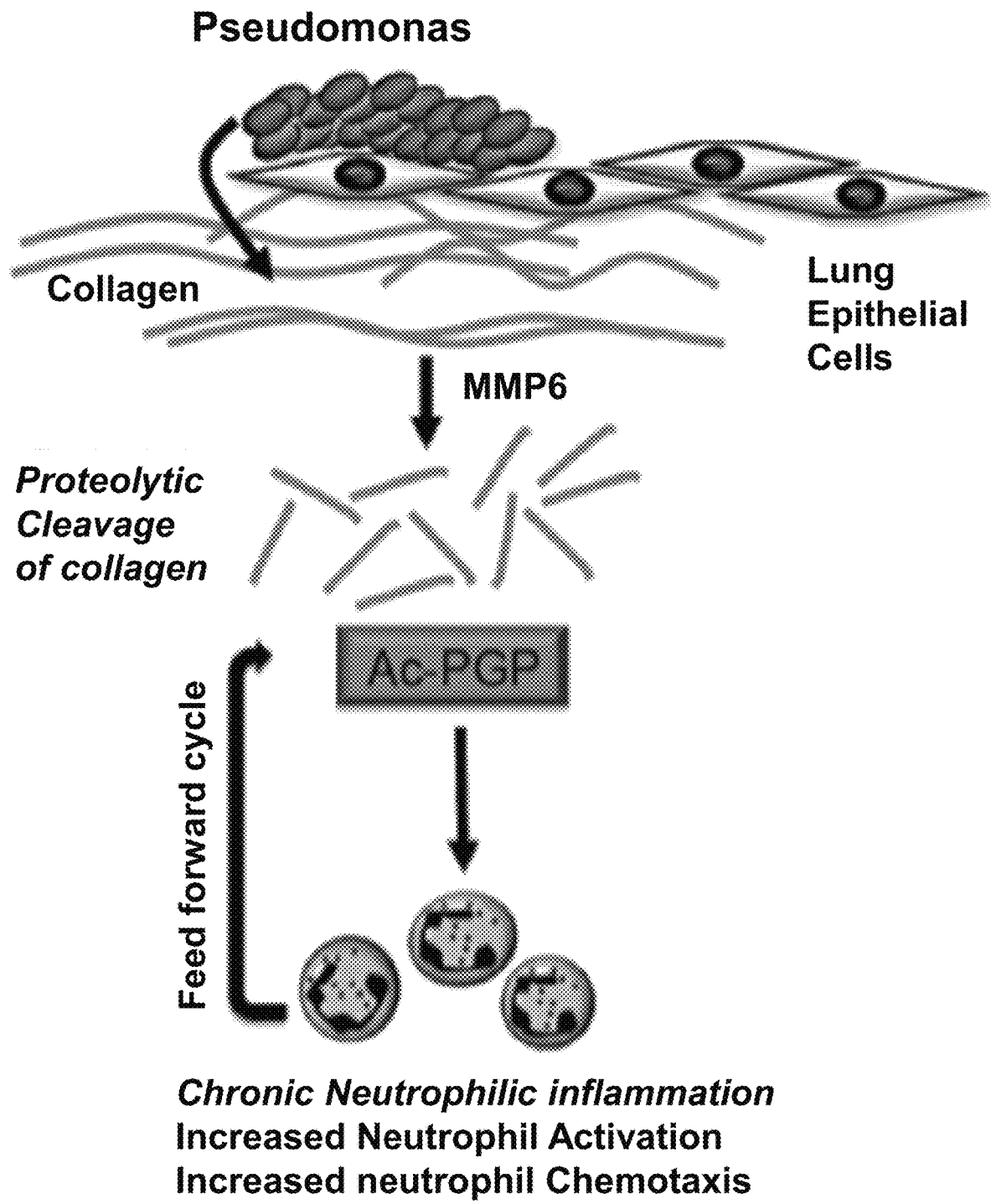
FIG. 13 schematically illustrates the generation of N-acetyl-Proline-Glycine-Proline (Ac-PGP) by Pseudomonas in the lungs of human subjects.
Figure 14:
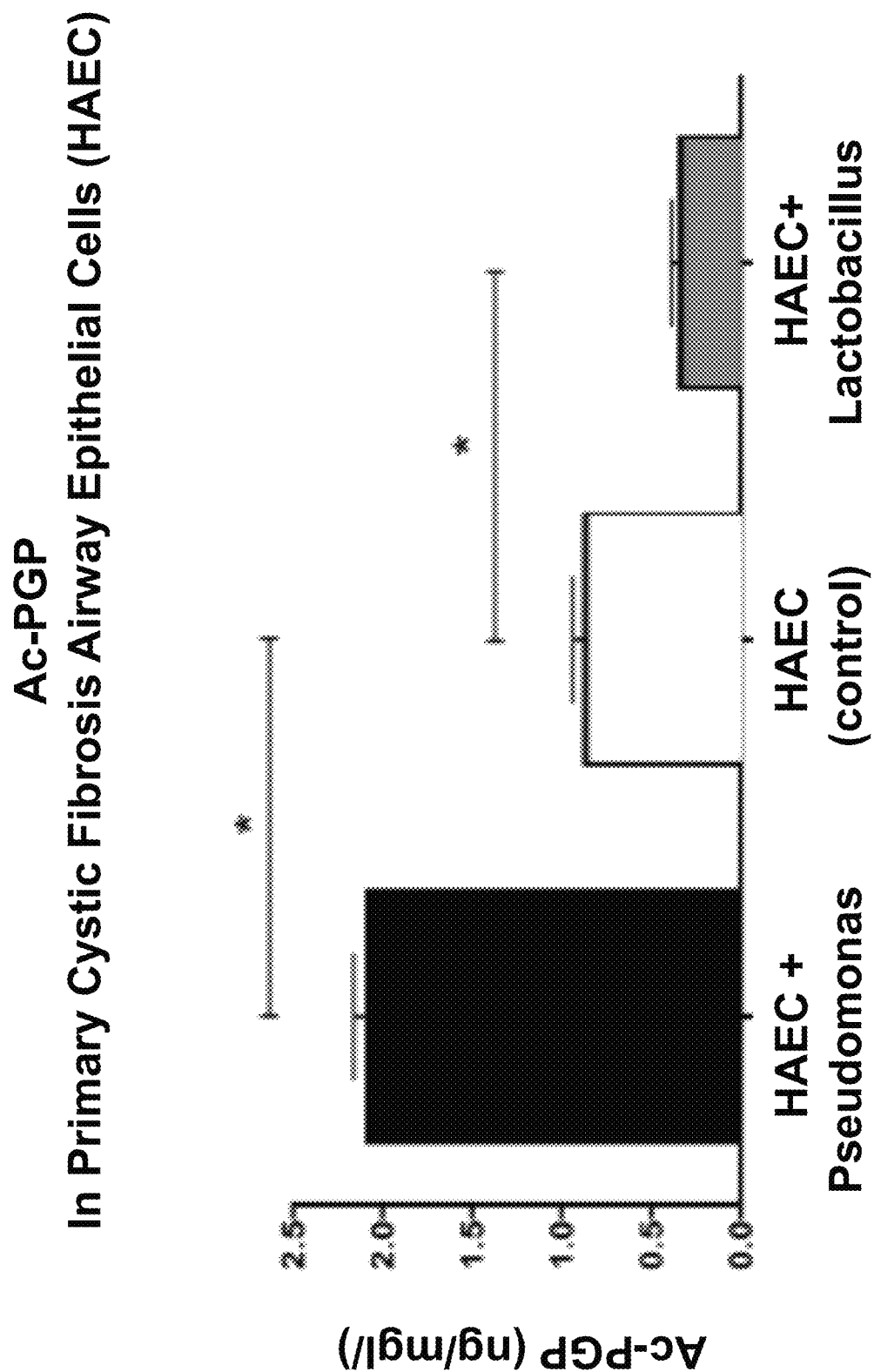
FIG. 14 is a graph illustrating the depression of Ac-PGP formation by primary Human Bronchial Epithelial Cells (NHBE) in tissue culture by Lactobacillus and elevation by a non-Lactobacillus species (Pseudomonas). The Lactobacillus combination versus Pseudomonas (pathogen in cystic fibrosis) was administered to Cystic Fibrosis Human Airway Epithelial cells for 12 hours and levels of potent neutrophilic chemotactic agent Ac-PGP were checked. The Lactobacillus combination decreased Ac-PGP levels, even below normal levels.
Figure 15:
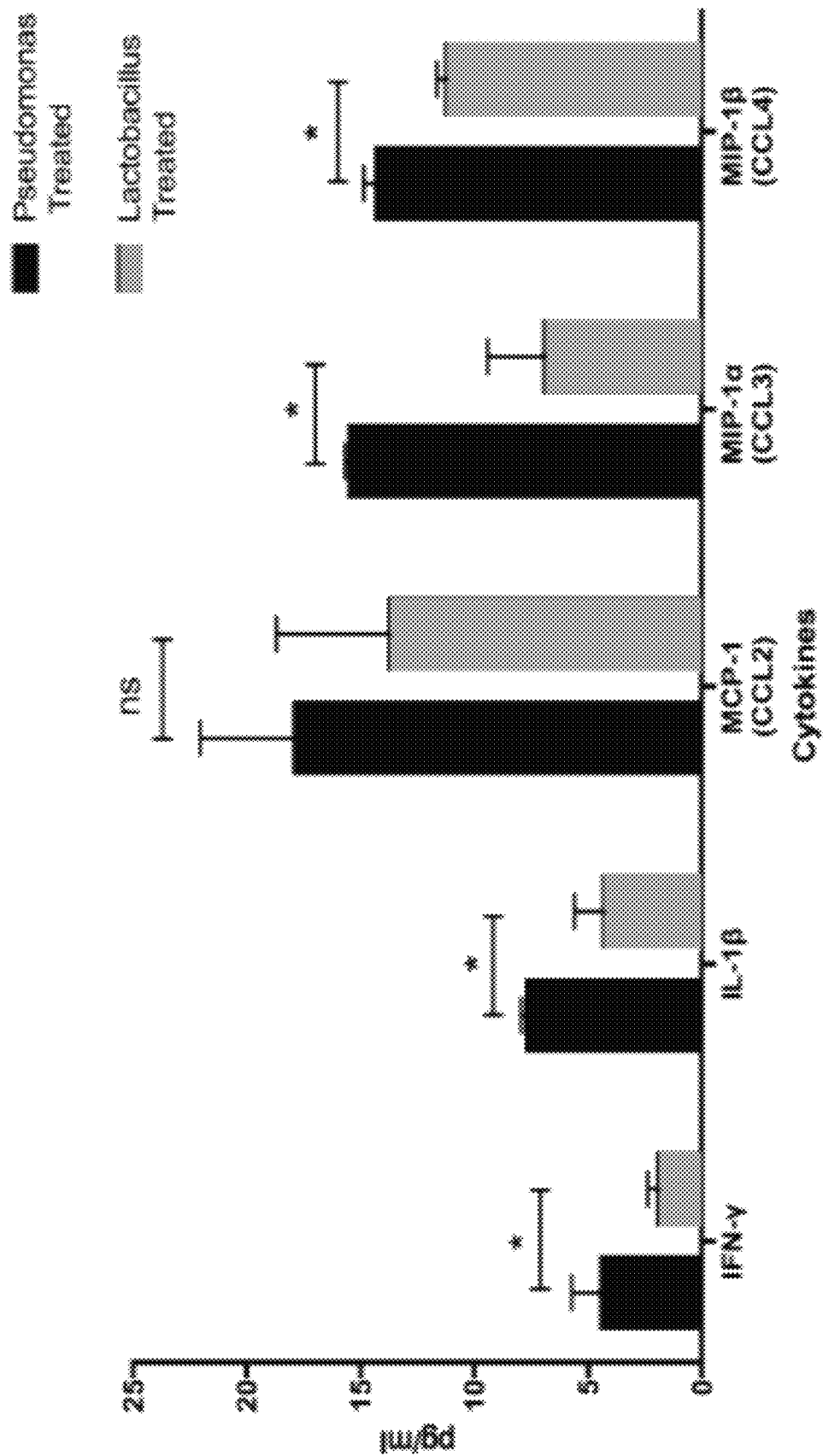
FIG. 15 is a graph illustrating the reduced level of cytokines in cultured HAEC cells from a cystic fibrosis patient formation from exposure to a Lactobacillus and elevation by a non-Lactobacillus species (Pseudomonas).

Endotoxin levels are increased in airways of infants with established BPD: Using a highly specific limulus amebocyte lysate (LAL) endotoxin assay endotoxin (Proteobacterial products) concentrations in TA were determined. Endotoxin expression was significantly increased in infants with established BPD compared to infants at birth (FIG. 7A, p<0.05). This corresponds to the airway microbiome analysis finding of increased Proteobacteria in infants with established BPD, compared to ELBW or FT infants at birth. At birth, endotoxin concentrations in airways of BPD Resistant and BPD Predisposed ELBW infants showed a statistically non-significant trend towards increase in BPD Predisposed infants, (FIG. 7B, p=0.1). In addition, no difference was seen in endotoxin levels in ELBW infants versus FT infants at birth (p>0.1).

Example 19

The airway microbiome of extremely preterm and term infants soon after birth and in preterm infants with established BPD was evaluated. One finding was that the airways have a diverse microbiome even at birth regardless of gestational age. It had been considered that infant mucosal surfaces are populated by skin, vaginal, and intestinal microbes derived from the mother (Dominguez-Bello et al. (2010) *Proc. Natl. Acad. Sci. USA* 107:11971-11975). As it is commonly believed that colonization of neonates originates in the birth canal, it was surprising to find that the airway microbiome of vaginally delivered and caesarean section-delivered neonates were similar, which suggests that the microbial DNA in the airways is probably transplacentally derived, consistent with reports that the placenta has a rich microbiome (Aagaard et al. (2014) *Sci. Transl. Med* 6: 237ra265).

It was also found that airway microbiota in infants with BPD has decreased diversity and is very different from that of either preterm infants soon after birth, or full term infants at a similar post-menstrual age. Observations indicate that the early airway microbiota is associated with the development of BPD in ELBW infants and the airway microbiome shows consistent changes over time from birth to the development of BPD.

In the absence of direct access to the newborn lung tissue and due to the inability to obtain broncheoalveolar lavage fluid in newborn infants, tracheal aspirates are a surrogate for evaluation of the processes in the lower airways and distal lungs. To date, two studies have utilized culture independent methods to detect airway organ-isms in preterm infants. In a study of 10 infants (Mourani et al. (2011) *PloS One* 6: e25959) airways of premature infants were shown not to be sterile. *Staphylococcus, Ureaplasma parvum,* and *Ureaplasma urealyticum* were the most frequently identified dominant organisms, among other identified organisms like *Pseudomonas, Enterococcus,* and *Escherichia*. Lohmann et al. (Lohmann et al. (2014) *Ped. Res.*, doi: 10.1038/pr.2014.85) studied the respiratory microbiome of 25 preterm infants but did not evaluate the microbiota of normal term infants.

The present study provides a more detailed comparison of the respiratory microbiome of ELBW, FT and BPD infants. The tight gestational age criteria in the ELBW group (mean gestation of 24.3±1.5 weeks) allowed study of infants who are at the highest risk of developing BPD. In this cohort, most mothers of ELBW infants received prenatal antimicrobial therapy close to delivery. As it is routine clinical practice to treat mothers in preterm labor with antimicrobials, it is difficult to generate an adequate sample size to determine the effect of antimicrobial therapy on the neonatal airway microbiome as there are very few infants who are not exposed.

A strength of the present study was the sterile collection of tracheal aspirate samples from intubated ELBW and FT infants at or within six hours of birth, thus reducing the chances of contamination or postnatal colonization. Only samples with greater than 1000 sequence reads were utilized for the qualitative analysis, further reducing the chances of erroneous results. Samples with low bacterial biomass were discarded. The increase in Proteobacteria in infants established BPD was marked by a corresponding increase in endotoxin levels, which adds validity to the microbiome analysis.

In the present study genomic approaches were employed rather than culture, and utilized separate development and validation cohorts to explore the predictive role of airway microbiome at birth for the future development of BPD. A central finding was the decreased *Lactobacillus* abundance in airway microbiome of infants born to mothers with chorioamnionitis. Gritz & Bhandari ((2015) Front. Pediatr. 3: doi: 10.3389/fped.2015.00017) have shown the importance of *Lactobacillus* spp. in preterm infants. Also, as chorioamnionitis is an independently-associated risk factor for BPD[14], this finding could be important in defining the association of chorioamnionitis and BPD. Decreased *Lactobacillus* abundance was found at birth in the airways of BPD-Predisposed ELBW infants as compared to BPD-Resistant infants. This finding is congruent with findings of Lynch et al. (Cox et al. (2010) *PLOS One* 5: e8745; Fujimura. et al. (2014) *Proc. Natl. Acad. Sci. USA* 111:805-810; Cope & Lynch (2015) *Curr. Allergy Asthma Rep.* 15:504), who have reported a beneficial role of *Lactobacillus* in other airway diseases. Studies in mice have shown that intranasal administration of *Lactobacilli* may be more potent than intragastric application in reducing allergic airway inflammation, possibly linked to an increase in T-regulatory cells in the lungs (Pellaton et al. (2012) *Int. J. Inflamm.* 2012:686-739). Other investigators have shown that higher bacterial abundance in non-specific-pathogen-free mice correlated with more and smaller size alveoli indicating better lung development, which was corroborated by transplanting *Lactobacillus* spp. into germ-free mice, which responded by improvement in alveolar development (Yun et al. (2014) *PLOS One* 9: e113466).

Fecal microbiota in preterm infants may vary by center (Taft et al. (2014) *Microbiome* 2:36), and it is possible that there is center variation in airway microbiota as well, which may lead to center variation in short-term as well as longer-term pulmonary outcomes. Hence, the present findings were validated with patient samples from a different center. Relative decreased *Lactobacillus* abundance at birth in airway microbiome was found to be predictive of BPD in the validation cohort as well. The results indicate that the respiratory microbiome at birth could potentially be used for prognosis, and may potentially be modulated perhaps using "respiratory probiotics" for therapeutic interventions in preterm lung disease. Although it is known that mode of delivery can shape the acquisition and structure of the skin microbiota in newborns[9], the study found no differences between the respiratory microbiome of ELBW infants born by cesarean section versus those born by vaginal delivery.

This finding indicates that the airway microbiome is probably established well before delivery (as it is diverse and similar in both extremely preterm and term infants), and is potentially through a transplacental passage of bacterial products. (Aagard et al. (2014) *Sci. Transl. Med* 6: 237ra265) have shown that the placental microbiome is very diverse, resembles the oral microbiome, and is similar to the airway microbiome in this study. Stout et al. (Stout et al. (2013) *Amer. J. Obstetr. Gynecol.* 208:221-227) have also demonstrated gram positive and negative intracellular bacteria in the basal plates of 27% of all placentas, even though it is highly probable that visual identification in a few selected high power fields is likely to be a marked underestimate. It is possible that the biologic rationale for why the placental microbiome resembles the oral microbiome (Aagaard et al. (2014) *Sci. Transl. Med* 6: 237ra265) and the neonatal airway microbiome is because a hematogenous transfer of oral microbes to the placenta (Aagaard et al. (2014) *Sci. Transl. Med* 6: 237ra265; Fardini et al. (2010) *Infect. Immun.* 78:1789-1796; Han et al. (2010) *Obstet. Gynecol.* 115:442-445; Han et al. (2006) *J. Clin. Microbiol.* 44:1475-1483; Han et al. (2009) *J. Clin. Microbiol.* 47:38-47) followed by transplacental transfer of placental microbiota ensures that the early airway microbiome and its associated pathogen-associated molecular patterns can initiate establishment of respiratory innate immunity before respiratory pathogens can establish a niche. Alternatively there could be a local microbial transfer from placenta to the amniotic fluid, which the fetal lungs acquire. Multiple studies utilizing culture and culture-independent have now confirmed that various bacterial species are detected in amniotic fluid[26]. The amniotic fluid microbiota and the airway microbiota could have a common origin from the placenta, and the level of microbial cross-transfer between these pools needs to be determined.

Although all attempts were made to collect TA specimens in a sterile fashion, there is a possibility that contamination could have occurred as inhaled microbiota could contribute to the airway microbiome (Wassenaar & Panigrahi (2014) *Letts Applied Microbiol.* 59:572-579). This could explain the increased Genus *Staphylococcus* abundance at birth in the airways of BPD-Predisposed ELBW infants in the present discovery cohort, which was not validated in the samples from the second site. Also, TAs might not represent the true microbiome of the distal lungs and could contain oral microbiota or aspirated gastric micro-biota in addition to airway microbiota. Thus, very early (at birth or within 6 h) collection of TA samples was used, when none of the infants were feeding. In addition, samples with only greater than 1000 sequence reads were used. A limitation of the study is the absence of "normal" full term controls to compare with diseased group, as normal infants do not get intubated. Although our FT infant cohort might not be the perfect controls, they were the only and the closest available options.

Serial microbiome analysis from the same patient may yield useful information on temporal changes leading to BPD. Thus, TA samples were collected from extremely preterm infants in a serial fashion, and found consistent temporal changes in the airway microbiome from birth until the development of BPD. These infants were of the smallest viable gestational ages from 22-24 wks, and hence were the most prone to develop BPD. All five infants had similar temporal changes in the airway microbiota—that of increasing abundance of Proteobacteria and decreased Firmicutes in airway microbiome over time, despite multiple courses of antibiotics at different time points. Genus *Lactobacillus* has been known to have strong anti-inflammatory properties (Justino et al. (2015) *Cancer Chemother. Pharmacol.* 75:559-567; Mohamadzadeh et al. (2011) *Proc. Natl. Acad. Sci. USA*, 108 (Suppl 1): 4623-4630; Macho Fernandez et al. (2011) *Gut* 60:1050-1059; Plaza-Diaz et al. (2014) *PLOS One* 9: e98401; Sagar et al. (2014) *Respir. Res.* 15:46; Simeoli et al. (2015) *J. Nutr,* 145: 1202-1210), and has been shown to regulate alveolar development in animal models (Yun et al. (2014) *PLOS One* 9: e113466). Hence, the temporal microbial dysbiosis consisting of the increase in Protecbacteria and decrease in Firmicutes such as *Lactobacillus* may contribute to the airway inflammation associated with BPD and resulting impairment in lung development. The serial tracheal sample findings in our study do show that the initial lung microbiome in infants tends to evolve over time. It is likely that the postnatal changes in the airway microbiome are driven by exposure to environmental microbes, and is modulated by antimicrobial therapy to the infant.

Further understanding of the role of the complex airway microbiome in preterm infants requires investigation of the interactions among genes of the microbiota and host. There is a possibility that the microbiome may have beneficial cross-talk with the host preterm lung and the reduced diversity of microbes resulting from intensive care interventions makes the host lung more susceptible for injury and inflammation. The lung microbiome, similar that of other compartments, may be manipulated to correct dysbiosis and restore "healthy" microbial communities via use of probiotics, prebiotics or antibiotics. Early-life gut microbial alterations include changes in the production of microbial-derived metabolites, and a similar phenomenon may happen in the lungs (Trompette et al. (2014) *Nat. Med.* 20:159-166).

Example 20

Growing *Lactobacilli*:
1. Culture *Lactobacilli plantarum, L. rhamnosus* and *L. acidophilus* in sterile LG agar, 5 cc., separate 50 ml tubes. Sterile technique.
2. Place in incubator shaker at 37° C., 200 Oscillations/min for at least 30 h. All three cultures are slow growing.
3. Measure bacteria concentration for each *Lactobacillus* species in spectrophotometer $OD_{600}$. Using bacteria/spectrophotometer calculator measure bacteria/ml and adjust concentration by diluting $1 \times 10^6$ in 200 µl of culture media.
4. For combination bacteria exposure adjust dilutions to $5 \times 10^5$ for two species or $3.33 \times 10^5$ for a three species combination. Calculate appropriate volumes and bacteria concentrations in separate tubes before treating.

For In Vitro Studies:
1. Trypsinize and count HBE WT from at least 4 flasks at 80 to 90% confluency in order to obtain approximately $10 \times 10^6$ cells.
2. Use 6 well collagen I coated plates. Seed 200k cells diluted in 2 ml of antibiotic-free FBS-free media per well around 5 to 6 hours before treating with bacteria. Incubate at 37° C. in CO2 incubator.
3. At least 60 to 90 mins prior to treatment collect media from each well 400 µl and centrifuge 2500 RPM for 5 min. Aliquot in several tubes:

a. 90 µl for acPGP MS
b. 30 µl for cytokines
c. approximately 280 µl as reserve for other tests
4. For control non-treated HBE cells add 200 µl media without bacteria at time of treating.
5. Add 200 µl bacteria in medium ($1 \times 10^6$ to each well.
6. Place one of control or treated plates in CO2 incubator and another one in hyperoxia incubator at 85% O2, 5% CO2 and 37° C. Keep undisturbed for exactly 12 h.
7. Pull out plates from incubators and collect media from each well and aliquot:
a. 70 µl for acPGP MS
b. 25 µl for cytokines
c. 1000 µl as reserve for other tests
8. Save samples at −80° C. until ready for testing. Save plates in zipper bags at −80° C. as an additional precaution.

Example 21

For Bronchopulmonary Dysplasia (BPD): Hyperoxia Model of BPD: From postnatal (PN) days 3-14, C57BL6 or SW mice pups were exposed to either 85% hyperoxia or normoxia. Surrogate dams were exchanged between normoxia and hyperoxia every 36 h to prevent maternal toxicity. Pups were analyzed at PN 1, 7, 11, and 42 as outlined below. Normoxic mice served as controls for all experiments. In addition, normoxic and hyperoxic germ free mice were compared with normoxic and hyperoxic wild type mice to delineate baseline differences in phenotype.

*Lactobacillus* Administration: The data demonstrated the important role of Ac-PGP induced-inflammation in the pathogenesis of BPD. It was found that *Lactobacillus* decreased the production of Ac-PGP and cytokines tested in WT and gnotobiotic mice, with or without hyperoxia exposure (FIGS. 20A and 20B). To develop therapeutic strategies, the *Lactobacillus* combination instillation or inhalation model was used to prevent neutrophil influx, secondary to complementary Ac-PGP and cytokine blockade (Aghai et al. (2013) *Pediatr. Pulmonol.* 48:8-13; Kozich et al. (2013) *Appl. Environ. Microbiol.* 79:5112-5120). Gnotobiotic Experiments: Mice in the gnotobiotic facility were derived germfree by hysterectomy and fostering on germfree Swiss Webster mice obtained from Taconic Farms, Inc. For microbiological monitoring autoclaving and isolator sterilization protocols were verified using spore strips and vials. Each isolator was monitored every 1-2 months for contamination by bacterial and fungal cultures and examination of air dried Gram stained suspensions of fresh fecal samples.

Animal harvesting: Lungs from PN 1 to PN 28 (PN1-mid-saccular phase, PN4-late saccular phase, PN7-early alveolar phase, PN11-alveolar phase and PN42-completed alveolarization) (4-7) were assessed for pulmonary development and the impact of specific bacterial inoculation. BAL obtained from mice as previously described (Rogers et al. (2014) *Thorax* 70:74-81) and were used for microbiome, matrikine/protease/cytokine analysis—as described below. Blood was collected in a micro syringe from cardiac puncture. Lungs were either inflation-fixed at 25 mm Hg with 4% paraformaldehyde for paraffin embedding/histology or snap frozen for protein and RNA isolation.

Bronchoalveolar Lavage (BAL) were obtained from mice as previously described (Rogers et al. (2014) *Thorax* 70:74-81) and were used for microbiome, matrikine/protease/cytokine analysis.

Lung morphometry: Lung alveolar morphometry was performed as described previously, with measurements of mean linear intercepts (MLI) and radial alveolar counts (RAC) being performed by an observer masked to sample identity (Viscardi et al. (2004) *Ped. Res.* 55:1009-1017).

Matrikines/Protease/Cytokines/ECM Measurements: These studies were performed on cell supernatents and murine serum/BAL fluid (Dominguez-Bello et al. (2010) *Proc. Natl. Acad. Sci. USA* 107:11971-11975).

ESI-LC/MS/MS for Ac-PGP detection: Ac-PGP and non-acetylated PGP were measured in BAL and serum samples as previously, using a MDS Sciex API-4000 spectrometer (Applied Biosystems, Foster City, CA) equipped with HPLC (Shimadzu, Kyoto, Japan). Positive electrospray mass transitions were at 312-140 and 312-112 for Ac-PGP.

Prolyl Endopeptidase (PE) Activity Assay: 20 µl of specimen is incubated with a specific substrate (2 mM Z-Gly-Pro-pNa) for 24 h at 37° C. and 5% CO2 and cleavage of para-nitroaniline (pNa) from the substrate by PE is detected using a spectrophotometer at 410 nm and compared to a generated standard curve for PE activity.

Elisa for MMP-9/LTA4H: The concentrations in BAL and cell supernatants were measured using an ELISA, according to the manufacturer's directions (MMP-9: R&D Systems, Minneapolis, MN; LTA4H: USCN Life Science, Hubei, PRC).

Cytokines in lung dysplasia: Total cytokines including IL1β, IL6, and CXCL2 (MIP-2) were measured via Biorad Cytokine Plex.

Pulmonary Function Testing (PFTs): Lung mechanics were obtained at PN 28. At the time of harvest pulmonary compliance and resistance as well as PV curves were obtained by employing the forced oscillation techniques using flexivent (SciREq). In brief, following tracheal cannulation and degassing, the lungs were inflated in stepwise fashion to an airway pressure of 30 cm $H_2O$. The lungs were then deflated and re-inflated to obtain a static volume-pressure relationship. Static compliance and hysteresis were derived from this relationship. In addition, the lung resting volume, the volume pressure relationship, dynamic compliance and total resistance were calculated and correlated to the histological and protein analysis.

Statistical Analysis: Based on our preliminary results of hyperoxia-induced alveolar simplification in untreated WT mice, to detect a 25% increase in (two SD) in the RAC, 6 animals per group were needed to provide 80% power with an alpha of 0.05. Data were tested for normality and equal variance assumptions and log transformed prior to analysis if needed. Statistical analysis for most animal experiments was performed using student T test and one-way ANOVA on software PRISM 4.0 for Macintosh (Graph pad software's, Inc., San Diego, CA). Multiple comparisons testing by the posthoc Bonferroni test was performed if statistical significance was noted by ANOVA.

Example 22

Baseline in vivo lung microbiome is not affected by hyperoxia exposure (prelim data): In order to determine baseline murine microbiome changes associated with hyperoxia exposure, BAL were collected at PN 14 from pups exposed to either 21% O2 (normoxia) or 85% O2 (hyperoxia) from PN 3-14. Microbiome analyses was performed on these samples by 16s rRNA sequencing followed by bioinformatics as shown in FIG. 3. No difference in either bacterial abundance (p>0.1), or bacterial diversity (Shannon alpha diversity, p>0.1; beta diversity by permanova, p=0.20) was seen between the normoxic and hyperoxic groups. This data rules out any confounding effects of hyperoxia on the baseline respiratory microbiome in mice.

Example 23

Bacteria Nebulization Technique:
1. Use only under fume hood and suction, under sterile conditions.
2. Fill up nebulizer reservoir cup with at least 250 ml sterile saline.
3. Add bacteria combination and adjust bacteria to final concentration of $1 \times 10^4$ bacteria×12 chambers per 20 ml.
4. Place one pup per chamber in carrousel.
5. Nebulize for 20 mins and measure final volume remaining in reservoir. Average saline nebulized should be 20 ml.
6. Return pups to cage promptly to avoid hypothermia.
7. Disinfect equipment using 70% alcohol or chlorhexidine.

Example 24

Model of (Pseudomonal Bead Inoculation) Cystic Fibrosis mice: Gut corrected CFtrtm1UncTg (FABPCFTR) 1Jaw/J mice were used to minimize bowel obstruction and maintain a normal diet with littermate controls. CF mice were transiently anesthetized with isoflurane and mucoid *Pseudomonas* (human CF clinical strain) agar beads at 104 cfu/ml in 100 µl PBS directly delivered to the lower administered to the lower airway via transglottal aspiration. The lower dose of the mucoid strain was utilized to lessen the mortality associated with acute lung injury. Mice were carefully followed for weight loss and distress during the acute phase (initial 72 h). Thereafter, mice were weighed qMWF. At 14 days post-inoculation, lung physiology, histopathology and bronchoalveolar lavage (BAL) are performed. BAL consists of 0.7 ml of PBS being instilled through the tracheal cannula and then retracted with a 1 ml syringe. The BAL fluid was processed for microbiology, cytology and cytokine measures. Lung harvesting for microbiology and biochemical measures are performed on the left lung. The left mainstem bronchus was clamped with a hemostat. Lung homogenate from the distal third of the left lung was processed for microbiology, the middle third for protein, and the proximal third for RT-PCR. Lung histology was performed on the right lung, either through flash freezing or formaldehyde instillation for paraffin blocks. The preservative was instilled through the tracheal cannula at 30 cmH20 then the trachea ligated to preserve tissue inflation. Measures of lung histology utilize tissue morphometry utilizing automated thresholding and cell counting tools.

Example 25

Model of *Lactobacillus* Inoculation and RTR administration: In separate experiments, *Pseudomonas* colonized adult CF mice were administered: Intratracheal *Lactobacillus* ($10^4$ CFU/g, 100 µl sterile saline every 3 days from days 3-14 after Pseudomonal bead inoculation; *Lactobacillus* combination were used as described or sterile saline control were used. 16s rRNA microbiome analysis was conducted on BAL from a cohort of these administered animals on days 3, 6 and 14 to demonstrate temporal bacterial colonization. All animals were harvested at 14 days from Pseudomonal bead inoculation.

Example 26

COPD Animal Model: Cigarette smoke-induced animal models of chronic obstructive pulmonary disease support the protease-anti-protease hypothesis of emphysema. Specific inbred mouse strains, including A/J, can demonstrate phenotypic alterations consistent with development COPD after smoke exposure. Female A/J mice underwent 22-weeks of cigarette smoke exposure and developed alveolar enlargement and RV hypertrophy, findings reminiscent of corpulmonale in COPD patients. AcPGP was present in higher quantities in the BALF, RV and the PA compared to the aorta or LV. These mice were inoculated with *Lactobacillus* weekly by intratracheal route, during the period of smoke exposure.

Histology: At each time point, 5 mice per group were collected for histology. The presence and extent of arterial plexopathy were evaluated on parenchymal lung sections. The lungs were paraffin embedded, processed, and stained with either H&E stain, Masson's trichrome (for ECM staining), or remain unstained for immunohistochemistry (IHC). Morphometric analysis of Lm of the alveolar airspace was conducted with increased Lm as evidence of alveolar enlargement. Prior to sectioning and staining, hearts were weighed to assess for RV hypertrophy. This was done by removing the atria followed by removal of the right ventricular wall from the left ventricle plus the septum. Ventricles were blotted to remove any excess fluid and weighed.

Bronchoalveolar Lavage Fluid (BALF)/Blood analysis: At each time point, 5 mice per group were selected for BAL as we have previously reported (Cox et al. (2010) *PLOS One* 5: e8745). After centrifugation, the supernatant was assessed for ET-1, NO, myeloperoxidase (MPO) and specific cytokines (EGF, VEGF, IL-6, TNFα, CXCL1/KC, and IFNγ). Total and differential cell counts were done on cytospin preparations stained with DiffQuik. Following anesthesia with ketamine/xylazine, cardiac puncture were done in all mice to obtain blood and similar measurements were performed.

We claim:

1. A method of reducing a bronchopulmonary disease of a patient, said method comprising the step of administering to the patient in need thereof an effective dose of a pharmaceutical composition comprising a bacterial population consisting of a combination of *Lactobacillus* species consisting of *Lactobacillus plantarum*, *Lactobacillus acidophilus*, and *Lactobacillus rhamnosus*, wherein the combination of the *Lactobacillus* species reduces neutrophilic inflammation when delivered to a recipient subject.

2. The method of claim 1, wherein the bronchopulmonary disease is bronchopulmonary dysplasia, cystic fibrosis lung disease, or chronic obstructive pulmonary disease.

3. The method of claim 1, wherein at least one of the *Lactobacillus* species is not capable of proliferating in the recipient subject.

4. The method of claim 1, wherein at least one of the *Lactobacillus* species is viable and capable of proliferating in the recipient patient.

5. The method of claim 1, wherein the bacterial population is suspended in a pharmaceutically acceptable carrier.

6. The method of claim 1, wherein the pharmaceutical composition further comprises at least one therapeutic agent for reducing at least one symptom or pathological effect of the bronchopulmonary disease in the subject.

7. The method of claim 6, wherein the therapeutic agent is an anti-inflammatory agent or an anti-oxidant.

8. The method of claim 1, wherein the pharmaceutical composition is delivered to the patient by a nebulizer.

* * * * *